United States Patent
Elbaz et al.

(10) Patent No.: US 10,528,636 B2
(45) Date of Patent: Jan. 7, 2020

(54) METHODS FOR DENTAL DIAGNOSTICS

(71) Applicant: Align Technology, Inc., San Jose, CA (US)

(72) Inventors: Gilad Elbaz, Tel Aviv (IL); Erez Lampert, Rehovot (IL); Yossef Atiya, Maccabim (IL); Avi Kopelman, Palo Alto, CA (US); Ofer Saphier, Rehovot (IL); Maayan Moshe, Ra'anana (IL); Shai Ayal, Shoham (IL)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 15/672,248

(22) Filed: Aug. 8, 2017

(65) Prior Publication Data
US 2018/0028065 A1 Feb. 1, 2018

Related U.S. Application Data

(63) Continuation of application No. 15/662,234, filed on Jul. 27, 2017, now Pat. No. 10,123,706, and a
(Continued)

(51) Int. Cl.
*A61B 1/24* (2006.01)
*A61B 5/00* (2006.01)
(Continued)

(52) U.S. Cl.
CPC ............ *G06F 16/9535* (2019.01); *A61B 1/24* (2013.01); *A61B 5/0062* (2013.01);
(Continued)

(58) Field of Classification Search
None
See application file for complete search history.

(56) References Cited

U.S. PATENT DOCUMENTS

| 2,171,695 A | 9/1939 | Harper |
| 2,467,432 A | 4/1949 | Kesling |
| (Continued) | | |

FOREIGN PATENT DOCUMENTS

| AU | 517102 B | 11/1977 |
| AU | 3031677 A | 11/1977 |
| (Continued) | | |

OTHER PUBLICATIONS

US 8,553,966 B1, 10/2013, Alpern et al. (withdrawn)
(Continued)

*Primary Examiner* — James A Thompson
(74) *Attorney, Agent, or Firm* — Shay Glenn LLP

(57) ABSTRACT

Methods and apparatuses for generating a model of a subject's teeth. Described herein are intraoral scanning methods and apparatuses for generating a three-dimensional model of a subject's intraoral region (e.g., teeth) including both surface features and internal features. These methods and apparatuses may be used for identifying and evaluating lesions, caries and cracks in the teeth. Any of these methods and apparatuses may use minimum scattering coefficients and/or segmentation to form a volumetric model of the teeth.

20 Claims, 34 Drawing Sheets

Related U.S. Application Data continuation of application No. 15/662,250, filed on Jul. 27, 2017.

(60) Provisional application No. 62/367,607, filed on Jul. 27, 2016, provisional application No. 62/477,387, filed on Mar. 27, 2017, provisional application No. 62/517,467, filed on Jun. 9, 2017.

(51) Int. Cl.

| | | |
|---|---|---|
| *A61C 9/00* | (2006.01) | |
| *G06T 7/55* | (2017.01) | |
| *G06T 7/73* | (2017.01) | |
| *G06T 15/08* | (2011.01) | |
| *H04N 13/221* | (2018.01) | |
| *H04N 13/246* | (2018.01) | |
| *H04N 13/254* | (2018.01) | |
| *H04N 13/257* | (2018.01) | |
| *H04N 13/271* | (2018.01) | |
| *G06F 16/9535* | (2019.01) | |
| *G06T 17/00* | (2006.01) | |
| *G06Q 50/00* | (2012.01) | |

(52) U.S. Cl.
CPC .......... *A61B 5/0086* (2013.01); *A61B 5/0088* (2013.01); *A61B 5/7203* (2013.01); *A61B 5/7435* (2013.01); *A61C 9/0053* (2013.01); *G06Q 50/01* (2013.01); *G06T 7/55* (2017.01); *G06T 7/75* (2017.01); *G06T 15/08* (2013.01); *G06T 17/00* (2013.01); *H04N 13/221* (2018.05); *H04N 13/246* (2018.05); *H04N 13/254* (2018.05); *H04N 13/257* (2018.05); *H04N 13/271* (2018.05); *A61B 2560/0223* (2013.01); *G06T 2207/30036* (2013.01); *G06T 2207/30244* (2013.01); *G06T 2210/41* (2013.01)

(56) References Cited

U.S. PATENT DOCUMENTS

| | | |
|---|---|---|
| 2,531,222 A | 11/1950 | Kesling |
| 3,379,193 A | 4/1968 | Monsghan |
| 3,385,291 A | 5/1968 | Martin |
| 3,407,500 A | 10/1968 | Kesling |
| 3,478,742 A | 11/1969 | Bohlmann |
| 3,496,936 A | 2/1970 | Gores |
| 3,533,163 A | 10/1970 | Kirschenbaum |
| 3,556,093 A | 1/1971 | Quick |
| 3,600,808 A | 8/1971 | Reeve |
| 3,660,900 A | 5/1972 | Andrews |
| 3,683,502 A | 8/1972 | Wallshein |
| 3,738,005 A | 6/1973 | Cohen et al. |
| 3,860,803 A | 1/1975 | Levine |
| 3,885,310 A | 5/1975 | Northcutt |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,195,046 A | 3/1980 | Kesling |
| 4,253,828 A | 3/1981 | Coles et al. |
| 4,255,138 A | 3/1981 | Frohn |
| 4,324,546 A | 4/1982 | Heitlinger et al. |
| 4,324,547 A | 4/1982 | Arcan et al. |
| 4,348,178 A | 9/1982 | Kurz |
| 4,419,992 A | 12/1983 | Chorbajian |
| 4,433,956 A | 2/1984 | Witzig |
| 4,478,580 A | 10/1984 | Barrut |
| 4,500,294 A | 2/1985 | Lewis |
| 4,505,673 A | 3/1985 | Yoshii |
| 4,519,386 A | 5/1985 | Sullivan |
| 4,526,540 A | 7/1985 | Dellinger |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,629,424 A | 12/1986 | Lauks et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,755,139 A | 7/1988 | Abbatte et al. |
| 4,757,824 A | 7/1988 | Chaumet |
| 4,763,791 A | 8/1988 | Halverson et al. |
| 4,764,111 A | 8/1988 | Knierim |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,886,451 A | 12/1989 | Cetlin |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | van der Zel |
| 4,941,826 A | 7/1990 | Loran et al. |
| 4,952,928 A | 8/1990 | Carroll et al. |
| 4,964,770 A | 10/1990 | Steinbichler et al. |
| 4,975,052 A | 12/1990 | Spencer et al. |
| 4,983,334 A | 1/1991 | Adell |
| 4,997,369 A | 3/1991 | Shafir |
| 5,002,485 A | 3/1991 | Aagesen |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,037,295 A | 8/1991 | Bergersen |
| 5,055,039 A | 10/1991 | Abbatte et al. |
| 5,100,316 A | 3/1992 | Wildman |
| 5,103,838 A | 4/1992 | Yousif |
| 5,121,333 A | 6/1992 | Riley et al. |
| 5,123,425 A | 6/1992 | Shannon et al. |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,204,670 A | 4/1993 | Stinton |
| 5,242,304 A | 9/1993 | Truax et al. |
| 5,245,592 A | 9/1993 | Kuemmel et al. |
| 5,273,429 A | 12/1993 | Rekow et al. |
| 5,278,756 A | 1/1994 | Lemchen et al. |
| 5,306,144 A | 4/1994 | Hibst et al. |
| 5,328,362 A | 7/1994 | Watson et al. |
| 5,335,657 A | 8/1994 | Terry et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,372,502 A | 12/1994 | Massen et al. |
| D354,355 S | 1/1995 | Hilgers |
| 5,382,164 A | 1/1995 | Stern |
| 5,395,238 A | 3/1995 | Andreiko et al. |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |

(56) References Cited

U.S. PATENT DOCUMENTS

| | | |
|---|---|---|
| 5,499,633 A | 3/1996 | Fenton |
| 5,528,735 A | 6/1996 | Strasnick et al. |
| 5,533,895 A | 7/1996 | Andreiko et al. |
| 5,540,732 A | 7/1996 | Testerman |
| 5,542,842 A | 8/1996 | Andreiko et al. |
| 5,543,780 A | 8/1996 | McAuley et al. |
| 5,549,476 A | 8/1996 | Stern |
| 5,562,448 A | 10/1996 | Mushabac |
| 5,570,182 A | 10/1996 | Nathel et al. |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre |
| 5,621,648 A | 4/1997 | Crump |
| 5,626,537 A | 5/1997 | Danyo et al. |
| 5,645,420 A | 7/1997 | Bergersen |
| 5,645,421 A | 7/1997 | Slootsky |
| 5,651,671 A | 7/1997 | Seay et al. |
| 5,655,653 A | 8/1997 | Chester |
| 5,659,420 A | 8/1997 | Wakai et al. |
| 5,683,243 A | 11/1997 | Andreiko et al. |
| 5,683,244 A | 11/1997 | Truax |
| 5,691,539 A | 11/1997 | Pfeiffer |
| 5,692,894 A | 12/1997 | Schwartz et al. |
| 5,725,376 A | 3/1998 | Poirier |
| 5,725,378 A | 3/1998 | Wang |
| 5,730,151 A | 3/1998 | Summer et al. |
| 5,737,084 A | 4/1998 | Ishihara |
| 5,740,267 A | 4/1998 | Echerer et al. |
| 5,742,700 A | 4/1998 | Yoon et al. |
| 5,769,631 A | 6/1998 | Williams |
| 5,774,425 A | 6/1998 | Ivanov et al. |
| 5,790,242 A | 8/1998 | Stern et al. |
| 5,799,100 A | 8/1998 | Clarke et al. |
| 5,800,174 A | 9/1998 | Andersson |
| 5,816,800 A | 10/1998 | Brehm et al. |
| 5,818,587 A | 10/1998 | Devaraj et al. |
| 5,823,778 A | 10/1998 | Schmitt et al. |
| 5,848,115 A | 12/1998 | Little et al. |
| 5,857,853 A | 1/1999 | van Nifterick et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,904,479 A | 5/1999 | Staples |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 5,980,246 A | 11/1999 | Ramsay et al. |
| 5,989,023 A | 11/1999 | Summer et al. |
| 6,044,309 A | 3/2000 | Honda |
| 6,049,743 A | 4/2000 | Baba |
| 6,053,731 A | 4/2000 | Heckenberger |
| 6,068,482 A | 5/2000 | Snow |
| 6,099,303 A | 8/2000 | Gibbs et al. |
| 6,099,314 A | 8/2000 | Kopelman et al. |
| 6,123,544 A | 9/2000 | Cleary |
| 6,152,731 A | 11/2000 | Jordan et al. |
| 6,154,676 A | 11/2000 | Levine |
| 6,183,248 B1 | 2/2001 | Chishti et al. |
| 6,186,780 B1 | 2/2001 | Hibst et al. |
| 6,190,165 B1 | 2/2001 | Andreiko et al. |
| 6,200,133 B1 | 3/2001 | Kittelsen |
| 6,201,880 B1 | 3/2001 | Elbaum et al. |
| 6,212,435 B1 | 4/2001 | Lattner et al. |
| 6,217,334 B1 | 4/2001 | Hultgren |
| 6,230,142 B1 | 5/2001 | Benigno et al. |
| 6,231,338 B1 | 5/2001 | de Josselin de Jong et al. |
| 6,239,705 B1 | 5/2001 | Glen |
| 6,243,601 B1 | 6/2001 | Wist |
| 6,263,234 B1 | 7/2001 | Engelhardt et al. |
| 6,299,438 B1 | 10/2001 | Sahagian et al. |
| 6,309,215 B1 | 10/2001 | Phan et al. |
| 6,315,553 B1 | 11/2001 | Sachdeva et al. |
| 6,328,745 B1 | 12/2001 | Ascherman |
| 6,334,073 B1 | 12/2001 | Levine |
| 6,350,120 B1 | 2/2002 | Sachdeva et al. |
| 6,364,660 B1 | 4/2002 | Durbin et al. |
| 6,382,975 B1 | 5/2002 | Poirier |
| 6,402,510 B1 | 6/2002 | Williams |
| 6,402,707 B1 | 6/2002 | Ernst |
| 6,405,729 B1 | 6/2002 | Thornton |
| 6,413,086 B1 | 7/2002 | Womack |
| 6,436,058 B1 | 8/2002 | Krahner et al. |
| 6,450,167 B1 | 9/2002 | David et al. |
| 6,450,807 B1 | 9/2002 | Chishti et al. |
| 6,482,298 B1 | 11/2002 | Bhatnagar |
| 6,499,995 B1 | 12/2002 | Schwartz |
| 6,515,593 B1 | 2/2003 | Stark et al. |
| 6,516,805 B1 | 2/2003 | Thornton |
| 6,520,772 B2 | 2/2003 | Williams |
| 6,524,101 B1 | 2/2003 | Phan et al. |
| 6,540,707 B1 | 4/2003 | Stark et al. |
| 6,572,372 B1 | 6/2003 | Phan et al. |
| 6,573,998 B2 | 6/2003 | Cohen Sabban |
| 6,594,539 B1 | 7/2003 | Geng |
| 6,597,934 B1 | 7/2003 | de Jong et al. |
| 6,602,070 B2 | 8/2003 | Miller et al. |
| 6,611,783 B2 | 8/2003 | Kelly et al. |
| 6,613,001 B1 | 9/2003 | Dworkin |
| 6,616,579 B1 | 9/2003 | Reinbold et al. |
| 6,623,698 B2 | 9/2003 | Kuo |
| 6,624,752 B2 | 9/2003 | Klitsgaard et al. |
| 6,626,180 B1 | 9/2003 | Kittelsen et al. |
| 6,640,128 B2 | 10/2003 | Vilsmeier et al. |
| 6,697,164 B1 | 2/2004 | Babayoff et al. |
| 6,702,765 B2 | 3/2004 | Robbins et al. |
| 6,702,804 B1 | 3/2004 | Ritter et al. |
| 6,705,863 B2 | 3/2004 | Phan et al. |
| 6,729,876 B2 | 5/2004 | Chishti et al. |
| 6,749,414 B1 | 6/2004 | Hanson et al. |
| 6,830,450 B2 | 12/2004 | Knopp et al. |
| 6,832,912 B2 | 12/2004 | Mao |
| 6,885,464 B1 | 4/2005 | Pfeiffer et al. |
| 6,890,285 B2 | 5/2005 | Rahman et al. |
| 6,976,841 B1 | 12/2005 | Osterwalder |
| 7,036,514 B2 | 5/2006 | Heck |
| 7,106,233 B2 | 9/2006 | Schroeder et al. |
| 7,112,065 B2 | 9/2006 | Kopelman et al. |
| 7,121,825 B2 | 10/2006 | Chishti et al. |
| 7,138,640 B1 | 11/2006 | Delgado et al. |
| 7,142,312 B2 | 11/2006 | Quadling et al. |
| 7,166,063 B2 | 1/2007 | Rahman et al. |
| 7,184,150 B2 | 2/2007 | Quadling et al. |
| 7,192,273 B2 | 3/2007 | McSurdy |
| 7,220,124 B2 | 5/2007 | Taub et al. |
| 7,286,954 B2 | 10/2007 | Kopelman et al. |
| 7,292,759 B2 | 11/2007 | Boutoussov et al. |
| 7,302,842 B2 | 12/2007 | Biester et al. |
| 7,338,327 B2 | 3/2008 | Sticker et al. |
| D565,509 S | 4/2008 | Fechner et al. |
| 7,351,116 B2 | 4/2008 | Dold |
| 7,357,637 B2 | 4/2008 | Liechtung |
| 7,450,231 B2 | 11/2008 | Johs et al. |
| 7,458,810 B2 | 12/2008 | Bergersen |
| 7,460,230 B2 | 12/2008 | Johs et al. |
| 7,462,076 B2 | 12/2008 | Walter et al. |
| 7,463,929 B2 | 12/2008 | Simmons |
| 7,500,851 B2 | 3/2009 | Williams |
| D594,413 S | 6/2009 | Palka et al. |
| 7,544,103 B2 | 6/2009 | Walter et al. |
| 7,553,157 B2 | 6/2009 | Abolfathi et al. |
| 7,561,273 B2 | 7/2009 | Stautmeister et al. |
| 7,577,284 B2 | 8/2009 | Wong et al. |
| 7,596,253 B2 | 9/2009 | Wong et al. |
| 7,597,594 B2 | 10/2009 | Stadler et al. |
| 7,609,875 B2 | 10/2009 | Liu et al. |
| D603,796 S | 11/2009 | Sticker et al. |
| 7,616,319 B1 | 11/2009 | Woollam et al. |
| 7,626,705 B2 | 12/2009 | Altendorf |
| 7,632,216 B2 | 12/2009 | Rahman et al. |
| 7,633,625 B1 | 12/2009 | Woollam et al. |

(56) References Cited

U.S. PATENT DOCUMENTS

| | | |
|---|---|---|
| 7,637,262 B2 | 12/2009 | Bailey |
| 7,668,355 B2 | 2/2010 | Wong et al. |
| 7,670,179 B2 | 3/2010 | Müller |
| 7,695,327 B2 | 4/2010 | Bäuerle et al. |
| 7,698,068 B2 | 4/2010 | Babayoff |
| 7,724,378 B2 | 5/2010 | Babayoff |
| D618,619 S | 6/2010 | Walter |
| 7,731,508 B2 | 6/2010 | Borst |
| 7,735,217 B2 | 6/2010 | Borst |
| 7,780,460 B2 | 8/2010 | Walter |
| 7,787,132 B2 | 8/2010 | Körner et al. |
| 7,791,810 B2 | 9/2010 | Powell |
| 7,796,243 B2 | 9/2010 | Choo-Smith et al. |
| 7,806,727 B2 | 10/2010 | Dold et al. |
| 7,813,787 B2 | 10/2010 | de Josselin de Jong et al. |
| 7,824,180 B2 | 11/2010 | Abolfathi et al. |
| 7,828,601 B2 | 11/2010 | Pyczak |
| 7,845,969 B2 | 12/2010 | Stadler et al. |
| 7,854,609 B2 | 12/2010 | Chen et al. |
| 7,862,336 B2 | 1/2011 | Kopelman et al. |
| 7,872,760 B2 | 1/2011 | Ertl |
| 7,874,836 B2 | 1/2011 | McSurdy |
| 7,874,849 B2 | 1/2011 | Sticker et al. |
| 7,878,801 B2 | 2/2011 | Abolfathi et al. |
| 7,892,474 B2 | 2/2011 | Shkolnik et al. |
| 7,907,280 B2 | 3/2011 | Johs et al. |
| 7,929,151 B2 | 4/2011 | Liang et al. |
| 7,947,508 B2 | 5/2011 | Tricca et al. |
| 7,959,308 B2 | 6/2011 | Freeman et al. |
| 7,963,766 B2 | 6/2011 | Cronauer |
| 7,986,415 B2 | 7/2011 | Thiel et al. |
| 8,017,891 B2 | 9/2011 | Nevin |
| 8,026,916 B2 | 9/2011 | Wen |
| 8,027,709 B2 | 9/2011 | Arnone et al. |
| 8,038,444 B2 | 10/2011 | Kitching et al. |
| 8,054,556 B2 | 11/2011 | Chen et al. |
| 8,070,490 B1 | 12/2011 | Roetzer et al. |
| 8,077,949 B2 | 12/2011 | Liang et al. |
| 8,083,556 B2 | 12/2011 | Stadler et al. |
| D652,799 S | 1/2012 | Mueller |
| 8,118,592 B2 | 2/2012 | Tortorici |
| 8,126,025 B2 | 2/2012 | Takeda |
| 8,144,954 B2 | 3/2012 | Quadling et al. |
| 8,160,334 B2 | 4/2012 | Thiel et al. |
| 8,201,560 B2 | 6/2012 | Dembro |
| 8,215,312 B2 | 7/2012 | Garabadian et al. |
| 8,240,018 B2 | 8/2012 | Walter et al. |
| 8,279,450 B2 | 10/2012 | Oota et al. |
| 8,292,617 B2 | 10/2012 | Brandt et al. |
| 8,294,657 B2 | 10/2012 | Kim et al. |
| 8,296,952 B2 | 10/2012 | Greenberg |
| 8,297,286 B2 | 10/2012 | Smernoff |
| 8,306,608 B2 | 11/2012 | Mandelis et al. |
| 8,314,764 B2 | 11/2012 | Kim et al. |
| 8,332,015 B2 | 12/2012 | Ertl |
| 8,354,588 B2 | 1/2013 | Sticker et al. |
| 8,366,479 B2 | 2/2013 | Borst et al. |
| 8,465,280 B2 | 6/2013 | Sachdeva et al. |
| 8,477,320 B2 | 7/2013 | Stock et al. |
| 8,488,113 B2 | 7/2013 | Thiel et al. |
| 8,520,922 B2 | 8/2013 | Wang et al. |
| 8,520,925 B2 | 8/2013 | Duret et al. |
| 8,556,625 B2 | 10/2013 | Lovely |
| 8,570,530 B2 | 10/2013 | Liang |
| 8,573,224 B2 | 11/2013 | Thornton |
| 8,577,212 B2 | 11/2013 | Thiel |
| 8,650,586 B2 | 2/2014 | Lee et al. |
| 8,675,706 B2 | 3/2014 | Seurin et al. |
| 8,723,029 B2 | 5/2014 | Pyczak et al. |
| 8,743,923 B2 | 6/2014 | Geske et al. |
| 8,767,270 B2 | 7/2014 | Curry et al. |
| 8,768,016 B2 | 7/2014 | Pan et al. |
| 8,771,149 B2 | 7/2014 | Rahman et al. |
| 8,839,476 B2 | 9/2014 | Adachi |
| 8,870,566 B2 | 10/2014 | Bergersen |
| 8,878,905 B2 | 11/2014 | Fisker et al. |
| 8,899,976 B2 | 12/2014 | Chen et al. |
| 8,936,463 B2 | 1/2015 | Mason et al. |
| 8,948,482 B2 | 2/2015 | Levin |
| 8,956,058 B2 | 2/2015 | Rösch |
| 8,992,216 B2 | 3/2015 | Karazivan |
| 9,022,792 B2 | 5/2015 | Sticker et al. |
| 9,039,418 B1 | 5/2015 | Rubbert |
| 9,084,535 B2 | 7/2015 | Girkin et al. |
| 9,108,338 B2 | 8/2015 | Sirovskiy et al. |
| 9,144,512 B2 | 9/2015 | Wagner |
| 9,192,305 B2 | 11/2015 | Levin |
| 9,204,952 B2 | 12/2015 | Lampalzer |
| 9,242,118 B2 | 1/2016 | Brawn |
| 9,261,358 B2 | 2/2016 | Atiya et al. |
| 9,336,336 B2 | 5/2016 | Deichmann et al. |
| 9,351,810 B2 | 5/2016 | Moon |
| 9,375,300 B2 | 6/2016 | Matov et al. |
| 9,408,743 B1 | 8/2016 | Wagner |
| 9,433,476 B2 | 9/2016 | Khardekar et al. |
| 9,439,568 B2 | 9/2016 | Atiya et al. |
| 9,444,981 B2 | 9/2016 | Bellis et al. |
| 9,463,287 B1 | 10/2016 | Lorberbaum et al. |
| 9,500,635 B2 | 11/2016 | Islam |
| 9,506,808 B2 | 11/2016 | Jeon et al. |
| 9,510,918 B2 | 12/2016 | Sanchez |
| 9,545,331 B2 | 1/2017 | Ingemarsson-Matzen |
| 9,584,771 B2 | 2/2017 | Mandelis et al. |
| 9,675,430 B2 | 6/2017 | Verker et al. |
| 9,693,839 B2 | 7/2017 | Atiya et al. |
| 9,744,006 B2 | 8/2017 | Ross |
| 9,861,451 B1 | 1/2018 | Davis |
| 9,936,186 B2 | 4/2018 | Jesenko et al. |
| 10,159,541 B2 | 12/2018 | Bindayel |
| 2001/0038705 A1 | 11/2001 | Rubbert et al. |
| 2001/0041320 A1 | 11/2001 | Phan et al. |
| 2002/0010568 A1 | 1/2002 | Rubbert et al. |
| 2002/0015934 A1 | 2/2002 | Rubbert et al. |
| 2003/0009252 A1 | 1/2003 | Pavlovskaia et al. |
| 2003/0035061 A1 | 2/2003 | Iwaki et al. |
| 2003/0049581 A1 | 3/2003 | Deluke |
| 2003/0139834 A1 | 7/2003 | Nikolskiy et al. |
| 2003/0190575 A1 | 10/2003 | Hilliard |
| 2003/0207224 A1 | 11/2003 | Lotte |
| 2003/0224311 A1 | 12/2003 | Cronauer |
| 2004/0009449 A1 | 1/2004 | Mah et al. |
| 2004/0019262 A1 | 1/2004 | Perelgut |
| 2004/0058295 A1 | 3/2004 | Bergersen |
| 2004/0094165 A1 | 5/2004 | Cook |
| 2004/0158194 A1 | 8/2004 | Wolff et al. |
| 2004/0167646 A1 | 8/2004 | Jelonek et al. |
| 2005/0023356 A1 | 2/2005 | Wiklof et al. |
| 2005/0031196 A1 | 2/2005 | Moghaddam et al. |
| 2005/0037312 A1 | 2/2005 | Uchida |
| 2005/0048433 A1 | 3/2005 | Hilliard |
| 2005/0100333 A1 | 5/2005 | Kerschbaumer et al. |
| 2005/0181333 A1 | 8/2005 | Karazivan et al. |
| 2005/0186524 A1 | 8/2005 | Abolfathi et al. |
| 2005/0244781 A1 | 11/2005 | Abels et al. |
| 2006/0084024 A1 | 4/2006 | Farrell |
| 2006/0099546 A1 | 5/2006 | Bergersen |
| 2006/0154198 A1 | 7/2006 | Durbin et al. |
| 2006/0223032 A1* | 10/2006 | Fried .................. A61B 5/0088 433/215 |
| 2006/0223342 A1 | 10/2006 | Borst et al. |
| 2006/0234179 A1 | 10/2006 | Wen et al. |
| 2007/0046865 A1 | 3/2007 | Umeda et al. |
| 2007/0053048 A1 | 3/2007 | Kumar et al. |
| 2007/0087300 A1 | 4/2007 | Willison et al. |
| 2007/0106138 A1 | 5/2007 | Beiski et al. |
| 2007/0134615 A1* | 6/2007 | Lovely ................ A61B 5/0088 433/29 |
| 2007/0184402 A1 | 8/2007 | Boutoussov et al. |
| 2007/0231765 A1 | 10/2007 | Phan et al. |
| 2007/0238065 A1 | 10/2007 | Sherwood et al. |
| 2007/0263226 A1 | 11/2007 | Kurtz et al. |
| 2008/0045053 A1 | 2/2008 | Stadler et al. |
| 2008/0057461 A1 | 3/2008 | Cheng et al. |
| 2008/0062429 A1 | 3/2008 | Liang et al. |

(56) References Cited

U.S. PATENT DOCUMENTS

| | | |
|---|---|---|
| 2008/0090208 A1 | 4/2008 | Rubbert |
| 2008/0115791 A1 | 5/2008 | Heine |
| 2008/0118886 A1 | 5/2008 | Liang et al. |
| 2008/0169122 A1 | 7/2008 | Shiraishi et al. |
| 2008/0176448 A1 | 7/2008 | Muller et al. |
| 2008/0242144 A1 | 10/2008 | Dietz |
| 2009/0030347 A1 | 1/2009 | Cao |
| 2009/0040740 A1 | 2/2009 | Muller et al. |
| 2009/0061379 A1 | 3/2009 | Yamamoto et al. |
| 2009/0061381 A1 | 3/2009 | Durbin et al. |
| 2009/0075228 A1 | 3/2009 | Kaneko et al. |
| 2009/0087050 A1* | 4/2009 | Gandyra ............... G01B 11/03 382/128 |
| 2009/0105523 A1 | 4/2009 | Kassayan et al. |
| 2009/0130620 A1 | 5/2009 | Yazdi et al. |
| 2009/0210032 A1 | 8/2009 | Beiski et al. |
| 2009/0218514 A1 | 9/2009 | Klunder et al. |
| 2009/0246726 A1 | 10/2009 | Chelnokov et al. |
| 2009/0281433 A1 | 11/2009 | Saadat et al. |
| 2009/0286195 A1 | 11/2009 | Sears et al. |
| 2009/0298017 A1 | 12/2009 | Boerjes et al. |
| 2009/0305540 A1 | 12/2009 | Stadler et al. |
| 2009/0317757 A1 | 12/2009 | Lemchen |
| 2010/0019170 A1 | 1/2010 | Hart et al. |
| 2010/0045902 A1 | 2/2010 | Ikeda et al. |
| 2010/0145898 A1 | 6/2010 | Malfliet et al. |
| 2010/0152599 A1 | 6/2010 | DuHamel et al. |
| 2010/0165275 A1 | 7/2010 | Tsukamoto et al. |
| 2010/0167225 A1 | 7/2010 | Kuo |
| 2010/0231577 A1 | 9/2010 | Kim et al. |
| 2010/0312484 A1 | 12/2010 | DuHamel et al. |
| 2011/0007920 A1 | 1/2011 | Abolfathi et al. |
| 2011/0012901 A1 | 1/2011 | Kaplanyan |
| 2011/0045428 A1 | 2/2011 | Boltunov et al. |
| 2011/0065060 A1 | 3/2011 | Teixeira et al. |
| 2011/0081625 A1 | 4/2011 | Fuh |
| 2011/0102549 A1 | 5/2011 | Takahashi |
| 2011/0102566 A1 | 5/2011 | Zakian et al. |
| 2011/0136090 A1 | 6/2011 | Kazemi |
| 2011/0143300 A1 | 6/2011 | Villaalba |
| 2011/0143673 A1 | 6/2011 | Landesman et al. |
| 2011/0235045 A1 | 9/2011 | Koerner et al. |
| 2011/0269092 A1 | 11/2011 | Kuo et al. |
| 2011/0316994 A1 | 12/2011 | Lemchen |
| 2012/0064477 A1 | 3/2012 | Schmitt |
| 2012/0081786 A1 | 4/2012 | Mizuyama et al. |
| 2012/0086681 A1 | 4/2012 | Kim et al. |
| 2012/0129117 A1 | 5/2012 | McCance |
| 2012/0147912 A1 | 6/2012 | Moench et al. |
| 2012/0172678 A1 | 7/2012 | Logan et al. |
| 2012/0281293 A1 | 11/2012 | Gronenborn et al. |
| 2012/0295216 A1 | 11/2012 | Dykes et al. |
| 2012/0322025 A1 | 12/2012 | Ozawa et al. |
| 2013/0089828 A1 | 4/2013 | Borovinskih et al. |
| 2013/0095446 A1 | 4/2013 | Andreiko et al. |
| 2013/0103176 A1 | 4/2013 | Kopelman et al. |
| 2013/0110469 A1 | 5/2013 | Kopelman |
| 2013/0150689 A1 | 6/2013 | Shaw-Klein |
| 2013/0163627 A1 | 6/2013 | Seurin et al. |
| 2013/0201488 A1 | 8/2013 | Ishihara |
| 2013/0235165 A1 | 9/2013 | Gharib et al. |
| 2013/0252195 A1 | 9/2013 | Popat |
| 2013/0266326 A1 | 10/2013 | Joseph et al. |
| 2013/0280671 A1 | 10/2013 | Brawn et al. |
| 2013/0286174 A1 | 10/2013 | Urakabe |
| 2013/0293824 A1 | 11/2013 | Yoneyama et al. |
| 2013/0323664 A1 | 12/2013 | Parker |
| 2013/0323671 A1 | 12/2013 | Dillon et al. |
| 2013/0323674 A1* | 12/2013 | Hakomori ............ A61B 5/0088 433/29 |
| 2013/0337412 A1 | 12/2013 | Kwon |
| 2014/0061974 A1 | 3/2014 | Tyler |
| 2014/0081091 A1 | 3/2014 | Abolfathi et al. |
| 2014/0122027 A1 | 5/2014 | Andreiko et al. |
| 2014/0186794 A1 | 7/2014 | Deichmann et al. |
| 2014/0265034 A1 | 9/2014 | Dudley |
| 2014/0272774 A1* | 9/2014 | Dillon ................. A61C 9/0053 433/29 |
| 2014/0294273 A1 | 10/2014 | Jaisson |
| 2014/0313299 A1 | 10/2014 | Gebhardt et al. |
| 2014/0329194 A1 | 11/2014 | Sachdeva et al. |
| 2014/0342301 A1 | 11/2014 | Fleer et al. |
| 2014/0363778 A1 | 12/2014 | Parker |
| 2015/0002649 A1 | 1/2015 | Nowak et al. |
| 2015/0079531 A1 | 3/2015 | Heine |
| 2015/0097315 A1 | 4/2015 | DeSimone et al. |
| 2015/0097316 A1 | 4/2015 | DeSimone et al. |
| 2015/0102532 A1 | 4/2015 | DeSimone et al. |
| 2015/0140502 A1 | 5/2015 | Brawn et al. |
| 2015/0164335 A1 | 6/2015 | Van Der Poel et al. |
| 2015/0173856 A1 | 6/2015 | Iowe et al. |
| 2015/0230885 A1 | 8/2015 | Wucher |
| 2015/0238280 A1 | 8/2015 | Wu et al. |
| 2015/0238283 A1 | 8/2015 | Tanugula et al. |
| 2015/0306486 A1 | 10/2015 | Logan et al. |
| 2015/0320320 A1 | 11/2015 | Kopelman et al. |
| 2015/0325044 A1 | 11/2015 | Lebovitz |
| 2015/0338209 A1 | 11/2015 | Knüttel |
| 2015/0374469 A1 | 12/2015 | Konno et al. |
| 2016/0000332 A1 | 1/2016 | Atiya et al. |
| 2016/0003610 A1 | 1/2016 | Lampert et al. |
| 2016/0022185 A1 | 1/2016 | Agarwal et al. |
| 2016/0042509 A1* | 2/2016 | Andreiko ............ G06K 9/00201 382/128 |
| 2016/0051345 A1 | 2/2016 | Levin |
| 2016/0064898 A1 | 3/2016 | Atiya et al. |
| 2016/0067013 A1 | 3/2016 | Morton et al. |
| 2016/0081768 A1 | 3/2016 | Kopelman et al. |
| 2016/0081769 A1 | 3/2016 | Kimura et al. |
| 2016/0135924 A1 | 5/2016 | Choi et al. |
| 2016/0135925 A1 | 5/2016 | Mason et al. |
| 2016/0163115 A1 | 6/2016 | Furst |
| 2016/0217708 A1 | 7/2016 | Levin et al. |
| 2016/0220105 A1 | 8/2016 | Durent |
| 2016/0220200 A1 | 8/2016 | Sandholm et al. |
| 2016/0225151 A1* | 8/2016 | Cocco .................... A61B 6/145 |
| 2016/0228213 A1 | 8/2016 | Tod et al. |
| 2016/0242871 A1 | 8/2016 | Morton et al. |
| 2016/0246679 A1 | 8/2016 | Kahn |
| 2016/0287358 A1* | 10/2016 | Nowak ................. A61B 5/1076 |
| 2016/0296303 A1 | 10/2016 | Parker |
| 2016/0328843 A1 | 11/2016 | Graham et al. |
| 2016/0367188 A1 | 12/2016 | Malik et al. |
| 2017/0007365 A1 | 1/2017 | Kopelman et al. |
| 2017/0007366 A1 | 1/2017 | Kopelman et al. |
| 2017/0007367 A1 | 1/2017 | Li et al. |
| 2017/0049311 A1 | 2/2017 | Borovinskih et al. |
| 2017/0049326 A1* | 2/2017 | Alfano ................. A61B 5/0075 |
| 2017/0056131 A1 | 3/2017 | Alauddin et al. |
| 2017/0086943 A1 | 3/2017 | Mah |
| 2017/0100214 A1 | 4/2017 | Wen |
| 2017/0156821 A1 | 6/2017 | Kopelman et al. |
| 2017/0215739 A1 | 8/2017 | Miyasato |
| 2017/0265970 A1 | 9/2017 | Verker |
| 2017/0319054 A1* | 11/2017 | Miller ................. A61B 1/0684 |
| 2017/0325690 A1* | 11/2017 | Salah ................... A61B 5/0088 |
| 2017/0340411 A1 | 11/2017 | Akselrod |
| 2017/0367585 A1* | 12/2017 | Islam .................... G01J 3/453 |
| 2018/0000563 A1 | 1/2018 | Shanjani et al. |
| 2018/0000565 A1 | 1/2018 | Shanjani et al. |
| 2018/0028063 A1 | 2/2018 | Elbaz et al. |
| 2018/0028064 A1 | 2/2018 | Elbaz et al. |
| 2018/0055602 A1 | 3/2018 | Kopelman et al. |
| 2018/0071054 A1 | 3/2018 | Ha |
| 2018/0085059 A1 | 3/2018 | Lee |
| 2018/0280118 A1 | 10/2018 | Cramer |
| 2018/0284727 A1 | 10/2018 | Cramer et al. |
| 2019/0026599 A1 | 1/2019 | Salah et al. |

FOREIGN PATENT DOCUMENTS

| | | |
|---|---|---|
| AU | 5598894 A | 6/1994 |
| CA | 1121955 A1 | 4/1982 |
| CN | 1655732 A | 8/2005 |

(56) References Cited

FOREIGN PATENT DOCUMENTS

| | | |
|---|---|---|
| CN | 1655733 A | 8/2005 |
| CN | 102017658 A | 4/2011 |
| CN | 103889364 A | 6/2014 |
| CN | 105997274 A | 10/2016 |
| DE | 2749802 A1 | 5/1978 |
| DE | 69327661 T2 | 7/2000 |
| DE | 102005043627 A1 | 3/2007 |
| DE | 202010017014 U1 | 3/2011 |
| DE | 102011051443 A1 | 1/2013 |
| DE | 102014225457 A1 | 6/2016 |
| EP | 0428152 A1 | 5/1991 |
| EP | 490848 A2 | 6/1992 |
| EP | 541500 A1 | 5/1993 |
| EP | 714632 B1 | 5/1997 |
| EP | 774933 B1 | 12/2000 |
| EP | 731673 B1 | 5/2001 |
| EP | 1693021 A1 | 8/2006 |
| EP | 1941843 A2 | 7/2008 |
| EP | 2437027 A2 | 4/2012 |
| EP | 2447754 A1 | 5/2012 |
| EP | 1989764 B1 | 7/2012 |
| EP | 2332221 B1 | 11/2012 |
| EP | 2596553 B1 | 12/2013 |
| EP | 2612300 B1 | 2/2015 |
| EP | 2848229 A1 | 3/2015 |
| ES | 463897 A1 | 1/1980 |
| ES | 2455066 A1 | 4/2014 |
| FR | 2369828 A1 | 6/1978 |
| FR | 2930334 A1 | 10/2009 |
| GB | 1550777 A | 8/1979 |
| JP | 53-058191 A | 5/1978 |
| JP | 4028359 A | 1/1992 |
| JP | 08-508174 A | 9/1996 |
| JP | 2007260158 A | 10/2007 |
| JP | 2008523370 A | 7/2008 |
| JP | 04184427 B1 | 11/2008 |
| JP | 2009000412 A | 1/2009 |
| JP | 2009018173 A | 1/2009 |
| JP | 2009205330 A | 9/2009 |
| JP | 2011087733 A | 5/2011 |
| JP | 2013007645 A | 1/2013 |
| JP | 201735173 A | 2/2017 |
| KR | 10-1266966 B1 | 5/2013 |
| KR | 10-2016-041632 A | 4/2016 |
| KR | 10-2016-0071127 A | 6/2016 |
| WO | WO91/004713 A1 | 4/1991 |
| WO | WO94/010935 A1 | 5/1994 |
| WO | WO98/032394 A1 | 7/1998 |
| WO | WO98/044865 A1 | 10/1998 |
| WO | WO02/017776 A2 | 3/2002 |
| WO | WO02/062252 A1 | 8/2002 |
| WO | WO02/095475 A1 | 11/2002 |
| WO | WO03/003932 A2 | 1/2003 |
| WO | WO2006/096558 A2 | 9/2006 |
| WO | WO2006/133548 A1 | 12/2006 |
| WO | WO2009/085752 A2 | 7/2009 |
| WO | WO2009/089129 A1 | 7/2009 |
| WO | WO2009/146788 A1 | 12/2009 |
| WO | WO2009/146789 A1 | 12/2009 |
| WO | WO2010/123892 A2 | 10/2010 |
| WO | WO2012/007003 A1 | 1/2012 |
| WO | WO2012/064684 A2 | 5/2012 |
| WO | WO2012/074304 A2 | 6/2012 |
| WO | WO2012/078980 A2 | 6/2012 |
| WO | WO2012/140021 A2 | 10/2012 |
| WO | WO2013/058879 A2 | 4/2013 |
| WO | WO2014/068107 A1 | 5/2014 |
| WO | WO2014/091865 A1 | 6/2014 |
| WO | WO2015/015289 A2 | 2/2015 |
| WO | WO2015/063032 A1 | 5/2015 |
| WO | WO2015/112638 A1 | 7/2015 |
| WO | WO2015/176004 A1 | 11/2015 |
| WO | WO2016/004415 A1 | 1/2016 |
| WO | WO2016/042393 A1 | 3/2016 |
| WO | WO2016/061279 A1 | 4/2016 |
| WO | WO2016/084066 A1 | 6/2016 |
| WO | WO2016/099471 A1 | 6/2016 |
| WO | WO2016/113745 A1 | 7/2016 |
| WO | WO2016/116874 A1 | 7/2016 |
| WO | WO2016/200177 A1 | 12/2016 |
| WO | WO2017/006176 A1 | 1/2017 |
| WO | WO2017/182654 A1 | 10/2017 |
| WO | WO2018/057547 A1 | 3/2018 |
| WO | WO2018/085718 A2 | 5/2018 |

OTHER PUBLICATIONS

Doruk et al.; The role of the headgear timer in extraoral cooperation; European Journal of Orthodontics; 26; pp. 289-291; Jun. 1, 2004.

Friedrich et al; Measuring system for in vivo recording of force systems in orthodontic treatment-concept and analysis of accuracy; J. Biomech.; 32(1); pp. 81-85; (Abstract Only) Jan. 1999.

Grest, Daniel; Marker-Free Human Motion Capture in Dynamic Cluttered Environments from a Single View-Point, PhD Thesis; 171 pages; Dec. 2007.

Invisalign; You were made to move. There's never been a better time to straighten your teeth with the most advanced clear aligner in the world; Product webpage; 2 pages; retrieved from the internet (www.invisalign.com/) on Dec. 28, 2017.

Kumar et al.; Rapid maxillary expansion: A unique treatment modality in dentistry; J. Clin. Diagn. Res.; 5(4); pp. 906-911; Aug. 2011.

Nedelcu et al.; "Scanning Accuracy and Precision in 4 Intraoral Scanners: An In Vitro Comparison Based on 3-Dimensional Analysis"; J. Prosthet. Dent.; 112(6); pp. 1461-71; Dec. 2014.

Sahm et al.; "Micro-Electronic Monitoring of Functional Appliance Wear"; Eur J Orthod.; 12(3); pp. 297-301; Aug. 1990.

Sahm; Presentation of a wear timer for the clarification of scientific questions in orthodontic orthopedics; Fortschritte der Kieferorthopadie; 51 (4); pp. 243-247; (Translation Included) Jul. 19990.

Schafer et al.; "Quantifying patient adherence during active orthodontic treatment with removable appliances using microelectronic wear-time documentation"; Eur J Orthod.; 37(1)pp. 1-8; doi:10.1093/ejo/cju012; Jul. 3, 2014.

Thera Mon; "Microsensor"; "2 pages"; retrieved from the interent (www.english.thera-mon.com/the-product/transponder/index.html); on Sep. 19, 2016.

Wikipedia; Palatal expansion; 3 pages; retrieved from the internet (https://en.wikipedia.org/wiki/Palatal_expansion) on Mar. 5, 2018.

Wireless Sensor Networks Magazine; Embedded Teeth for Oral Activity Recognition; 2 pages; retrievedon Sep. 19, 2016 from the internet (www.wsnmagazine.com/embedded-teeth/); Jul. 29, 2013.

Witt et al.; The wear-timing measuring device in orthodontics-cui bono? Reflections on the state-of-the-art in wear-timing measurement and compliance research in orthodontics; Fortschr Kieferorthop.; 52(3); pp. 117-125; (Translation Included) Jun. 1991.

Carrier et al.; U.S. Appl. No. 15/803,718 entitled "Methods and apparatuses for dental images," filed Nov. 3, 2017.

Kuo; U.S. Appl. No. 15/829,504 entitled "Dental appliance features for speech enhancement," filed Dec. 1, 2017.

Atiya et al.; U.S. Appl. No. 15/859,010 entitled "Compact confocal dental scanning apparatus," filed Dec. 29, 2017.

Shanjani et al.; U.S. Appl. No. 15/831,159 entitled "Palatal expanders and methodS of expanding a palate," filed Dec. 4, 2017.

Wu et al.; U.S. Appl. No. 15/831,262 entitled "Methods and apparatuses for customizing a rapid palatal expander," filed Dec. 4, 2017.

Grove et al.; U.S. Appl. No. 15/726,243 entitled "Interproximal reduction templates," filed Oct. 5, 2017.

Yamada et al.; Simulation of fan-beam type optical computed-tomography imaging of strongly scattering and weakly absorbing media; Applied Optics; 32(25); pp. 4808-4814; Sep. 1, 1993.

Bandodkar et al.; All-printed magnetically self-healing electrochemical devices; Science Advances; 2(11); 11 pages; e1601465; Nov. 2016.

(56) References Cited

OTHER PUBLICATIONS

Bandodkar et al.; Self-healing inks for autonomous repair of printable electrochemical devices; Advanced Electronic Materials; 1(12); 5 pages; 1500289; Dec. 2015.

Bandodkar et al.; Wearable biofuel cells: a review; Electroanalysis; 28(6); pp. 1188-1200; Jun. 2016.

Bandodkar et al.; Wearable chemical sensors: present challenges and future prospects; Acs Sensors; 1(5); pp. 464-482; May 11, 2016.

Imani et al.; A wearable chemical-electrophysiological hybrid biosensing system for real-time health and fitness monitoring; Nature Communications; 7; 11650. doi 1038/ncomms11650; 7 pages; May 23, 2016.

Jia et al.; Epidermal biofuel cells: energy harvesting from human perspiration; Angewandle Chemie International Edition; 52(28); pp. 7233-7236; Jul. 8, 2013.

Jia et al.; Wearable textile biofuel cells for powering electronics; Journal of Materials Chemistry A; 2(43); pp. 18184-18189; Oct. 14, 2014.

Jeerapan et al.; Stretchable biofuel cells as wearable textile-based self-powered sensors; Journal of Materials Chemistry A; 4(47); pp. 18342-18353; Dec. 21, 2016.

Kim et al.; Advanced materials for printed wearable electrochemical devices: A review; Advanced Electronic Materials; 3(1); 15 pages; 1600260; Jan. 2017.

Kim et al.; Noninvasive alcohol monitoring using a wearable tatto-based iontophoretic-biosensing system; Acs Sensors; 1(8); pp. 1011-1019; Jul. 22, 2016.

Kim et al.; Non-invasive mouthguard biosensor for continuous salivary monitoring of metabolites; Analyst; 139(7); pp. 1632-1636; Apr. 7, 2014.

Kim et al.; A wearable fingernail chemical sensing platform: pH sensing at your fingertips; Talanta; 150; pp. 622-628; Apr. 2016.

Kim et al.; Wearable salivary uric acid mouthguard biosensor with integrated wireless electronics; Biosensors and Bioelectronics; 74; pp. 1061-1068; 19 pages; (Author Manuscript); Dec. 2015.

Kumar et al.; All-printed, stretchable Zn—Ag2o rechargeable battery via, hyperelastic binder for self-powering wearable electronics; Advanced Energy Materials; 7(8); 8 pages; 1602096; Apr. 2017.

Kumar et al.; Biomarkers in orthodontic tooth movement; Journal of Pharmacy Bioallied Sciences; 7(Suppl 2); pp. S325-S330; 12 pages; (Author Manuscript); Aug. 2015.

Parrilla et al.; A textile-based stretchable multi-ion potentiometric sensor; Advanced Healthcare Materials; 5(9); pp. 996-1001; May 2016.

Windmiller et al.; Wearable electrochemical sensors and biosensors: a review; Electroanalysis; 25(1); pp. 29-46; Jan. 2013.

Zhou et al.; Bio-logic analysis of injury biomarker patterns in human serum samples; Talanta; 83(3); pp. 955-959; Jan. 15, 2011.

Zhou et al.; Biofuel cells for self-powered electrochemical biosensing and logic biosensing: A review; Electroanalysis; 24(2); pp. 197-209; Feb. 2012.

Kopelman et al.; U.S. Appl. No. 16/152,281 entitled "Intraoral appliances for sampling soft-tissue," filed Oct. 4, 2018.

Morton et al.; U.S. Appl. No. 16/177,067 entitled "Dental appliance having selective occlusal loading and controlled intercuspation," filed Oct. 31, 2018.

Akopov et al.; U.S. Appl. No. 16/178,491 entitled "Automatic treatment planning," filed Nov. 1, 2018.

Elbaz et al.; U.S. Appl. No. 16/198,488 entitled "Intraoral scanner with dental diagnostics capabilities," filed Nov. 21, 2018.

Elbaz et al.; U.S. Appl. No. 16/188,262 entitled "Intraoral scanner with dental diagnostics capabilities," filed Nov. 12, 2018.

AADR. American Association for Dental Research; Summary of Activities; Los Angeles, CA; p. 195; Mar. 20-23,(year of pub. sufficiently earlier than effective US filing date and any foreign priority date) 1980.

Alcaniz et aL; An Advanced System for the Simulation and Planning of Orthodontic Treatments; Karl Heinz Hohne and Ron Kikinis (eds.); Visualization in Biomedical Computing, 4th Intl. Conf, VBC '96, Hamburg, Germany; Springer-Verlag; pp. 511-520; Sep. 22-25, 1996.

Alexander et al.; The DigiGraph Work Station Part 2 Clinical Management; J. Clin. Orthod.; pp. 402-407; (Author Manuscript); Jul. 1990.

Align Technology; Align technology announces new teen solution with introduction of invisalign teen with mandibular advancement; 2 pages; retrieved from the internet (http://investor.aligntech.com/static-files/eb4fa6bb-3e62-404f-b74d-32059366a01b); Mar. 6, 2017.

Allesee Orthodontic Appliance: Important Tip About Wearing the Red White & Blue Active Clear Retainer System; Allesee Orthodontic Appliances-Pro Lab; 1 page; (year of pub. sufficiently earlier than effective US filing date and any foreign priority date); 1998.

Allesee Orthodontic Appliances: DuraClearTM; Product information; 1 page; (year of pub. sufficiently earlier than effective US filing date and any foreign priority date) 1997.

Allesee Orthodontic Appliances; The Choice Is Clear: Red, White & Blue . . . The Simple, Affordable, No-Braces Treatment; ( product information for doctors); retrieved from the internet (http://ormco.com/aoa/appliancesservices/RWB/doctorhtml); 5 pages on May 19, 2003.

Allesee Orthodontic Appliances; The Choice Is Clear: Red, White & Blue . . . The Simple, Affordable, No-Braces Treatment; (product information), 6 pages; (year of pub. sufficiently earlier than effective US filing date and any foreign priority date) 2003.

Allesee Orthodontic Appliances; The Choice is Clear: Red, White & Blue . . . The Simple, Affordable, No-Braces Treatment;(Patient Information); retrieved from the internet (http://ormco.com/aoa/appliancesservices/RWB/patients.html); 2 pages on May 19, 2003.

Allesee Orthodontic Appliances; The Red, White & Blue Way to Improve Your Smile; (information for patients), 2 pages; (year of pub. sufficiently earlier than effective US filing date and any foreign priority date) 1992.

Allesee Orthodontic Appliances; You may be a candidate for this invisible no-braces treatment; product information for patients; 2 pages; (year of pub. sufficiently earlier than effective US filing date and any foreign priority date) 2002.

Altschuler et al.; Analysis of 3-D Data for Comparative 3-D Serial Growth Pattern Studies of Oral-Facial Structures; AADR Abstracts, Program and Abstracts of Papers, 57th General Session, IADR Annual Session, Mar. 29, 1979-Apr. 1, 1979, New Orleans Marriot; Journal of Dental Research; vol. 58, Special Issue A, p. 221; Jan. 1979.

Altschuler et al.; Laser Electro-Optic System for Rapid Three-Dimensional (3D) Topographic Mapping of Surfaces; Optical Engineering; 20(6); pp. 953-961; Dec. 1981.

Altschuler et al.; Measuring Surfaces Space-Coded by a Laser-Projected Dot Matrix; SPIE Imaging q Applications for Automated Industrial Inspection and Assembly; vol. 182; pp. 187-191; Oct. 10, 1979.

Altschuler; 3D Mapping of Maxillo-Facial Prosthesis; AADR Abstract #607; 2 pages total, (year of pub. sufficiently earlier than effective US filing date and any foreign priority date) 1980.

Alves et al.; New trends in food allergens detection: toward biosensing strategies; Critical Reviews in Food Science and Nutrition; 56(14); pp. 2304-2319; doi: 10.1080/10408398.2013.831026; Oct. 2016.

Andersson et al.; Clinical Results with Titanium Crowns Fabricated with Machine Duplication and Spark Erosion; Acta Odontologica Scandinavica; 47(5); pp. 279-286; Oct. 1989.

Andrews, The Six Keys to Optimal Occlusion Straight Wire, Chapter 3, L.A. Wells; pp. 13-24; (year of pub. sufficiently earlier than effective US filing date and any foreign priority date) 1989.

Barone et al.; Creation of 3D multi-body orthodontic models by using independent imaging sensors; Sensors; 13(2); pp. 2033-2050; Feb. 5, 2013.

Bartels et al.; An Introduction to Splines for Use in Computer Graphics and Geometric Modeling; Morgan Kaufmann Publishers; pp. 422-425 Jan. 1, 1987.

(56) References Cited

OTHER PUBLICATIONS

Baumrind et al, "Mapping the Skull in 3-D," reprinted from J. Calif. Dent. Assoc, 48(2), 11 pages; (year of pub. sufficiently earlier than effective US filing date and any foreign priority date) Fall Issue 1972.
Baumrind et al.; A Stereophotogrammetric System for the Detection of Prosthesis Loosening in Total Hip Arthroplasty; NATO Symposium on Applications of Human Biostereometrics; SPIE; vol. 166; pp. 112-123; Jul. 9-13, 1978.
Baumrind; A System for Cranio facial Mapping Through the Integration of Data from Stereo X-Ray Films and Stereo Photographs; an invited paper submitted to the 1975 American Society of Photogram Symposium on Close-Range Photogram Systems; University of Illinois; pp. 142-166; Aug. 26-30, 1975.
Baumrind; Integrated Three-Dimensional Craniofacial Mapping: Background, Principles, and Perspectives; Seminars in Orthodontics; 7(4); pp. 223-232; Dec. 2001.
Begole et al.; A Computer System for the Analysis of Dental Casts; The Angle Orthodontist; 51(3); pp. 252-258; Jul. 1981.
Bernard et al; Computerized Diagnosis in Orthodontics for Epidemiological Studies: A ProgressReport; (Abstract Only), J. Dental Res. Special Issue, vol. 67, p. 169, paper presented at International Association for Dental Research 66th General Session, Montreal Canada; Mar. 9-13, 1988.
Bhatia et al.; A Computer-Aided Design for Orthognathic Surgery; British Journal of Oral and Maxillofacial Surgery; 22(4); pp. 237-253; Aug. 1, 1984.
Biggerstaff et al.; Computerized Analysis of Occlusion in the Postcanine Dentition; American Journal of Orthodontics; 61(3); pp. 245-254; Mar. 1972.
Biggerstaff; Computerized Diagnostic Setups and Simulations; Angle Orthodontist; 40(1); pp. 28-36; Jan. 1970.
Biostar Operation & Training Manual. Great Lakes Orthodontics, Ltd. 199 Fire Tower Drive,Tonawanda, New York. 14150-5890, 20 pages; (year of pub. sufficiently earlier than effective US filing date and any foreign priority date) 1990.
Blu et al.; Linear interpolation revitalized; IEEE Transactions on Image Processing; 13(5); pp. 710-719; May 2004.
Bourke, Coordinate System Transformation; 1 page; retrived from the internet (http://astronomy.swin.edu.au/˜ pbourke/prolection/coords) on Nov. 5, 2004; Jun. 1996.
Boyd et al.; Three Dimensional Diagnosis and Orthodontic Treatment of Complex Malocclusions With the Invisalipn Appliance; Seminars in Orthodontics; 7(4); pp. 274-293; Dec. 2001.
Brandestini et al.; Computer Machined Ceramic Inlays: In Vitro Marginal Adaptation; J. Dent. Res. Special Issue; (Abstract 305); vol. 64; p. 208; (year of pub. sufficiently earlier than effective US filing date and any foreign priority date) 1985.
Brook et al.; An Image Analysis System for the Determination of Tooth Dimensions from Study Casts: Comparison with Manual Measurements of Mesio-distal Diameter; Journal of Dental Research; 65(3); pp. 428-431; Mar. 1986.
Burstone et al.; Precision Adjustment of the Transpalatal Lingual Arch: Computer Arch Form Predetermination; American Journal of Orthodontics; 79(2);pp. 115-133; Feb. 1981.
Burstone; Dr. Charles J. Burstone on the Uses of the Computer in Orthodontic Practice (Part 1); Journal of Clinical Orthodontics; 13(7); pp. 442-453; (interview); Jul. 1979.
Burstone; Dr. Charles J. Burstone on the Uses of the Computer in Orthodontic Practice (Part 2); journal of Clinical Orthodontics; 13(8); pp. 539-551 (interview); Aug. 1979.
Cardinal Industrial Finishes; Powder Coatings; 6 pages; retrieved from the internet (http://www.cardinalpaint.com) on Aug. 25, 2000.
Carnaghan, An Alternative to Holograms for the Portrayal of Human Teeth; 4th Int'l. Conf. on Holographic Systems, Components and Applications; pp. 228-231; Sep. 15, 1993.
Chaconas et al,; The DigiGraph Work Station, Part 1, Basic Concepts; Journal of Clinical Orthodontics; 24(6); pp. 360-367; (Author Manuscript); Jun. 1990.
Chafetz et al.; Subsidence of the Femoral Prosthesis, a Stereophotogrammetric Evaluation; Clinical Orthopaedics and Related Research; No. 201; pp. 60-67; Dec. 1985.
Chiappone; Constructing the Gnathologic Setup and Positioner; Journal of Clinical Orthodontics; 14(2); pp. 121-133; Feb. 1980.
Chishti et al.; U.S. Appl. No. 60/050,342 entitled "Procedure for moving teeth using a seires of retainers," filed Jun. 20, 1997.
CSI Computerized Scanning and Imaging Facility; What is a maximum/minimum intensity projection (MIP/MinIP); 1 page; retrived from the Internet (http://csi.whoi.edu/content/what-maximumminimum-intensity-projection-mipminip); Jan. 4, 2010.
Cottingham; Gnathologic Clear Plastic Positioner; American Journal of Orthodontics; 55(1); pp. 23-31; Jan. 1969.
Crawford; CAD/CAM in the Dental Office: Does It Work?; Canadian Dental Journal; 57(2); pp. 121-123 Feb. 1991.
Crawford; Computers in Dentistry: Part 1: CAD/CAM: The Computer Moves Chairside, Part 2: F. Duret ' A Man With a Vision, Part 3: The Computer Gives New Vision—Literally, Part 4: Bytes 'N Bites the Computer Moves From the Front Desk to the Operatory; Canadian Dental Journal; 54(9); pp. 661-666 Sep. 1988.
Crooks; CAD/CAM Comes to USC; USC Dentistry; pp. 14-17; (year of pub. sufficiently earlier than effective US filing date and any foreign priority date) Spring 1990.
Cureton; Correcting Malaligned Mandibular Incisors with Removable Retainers; Journal of Clinical Orthodontics; 30(7); pp. 390-395; Jul. 1996.
Curry et al.; Integrated Three-Dimensional Craniofacial Mapping at the Craniofacial Research InstrumentationLaboratory/University of the Pacific; Seminars in Orthodontics; 7(4); pp. 258-265; Dec. 2001.
Cutting et al.; Three-Dimensional Computer-Assisted Design of Craniofacial Surgical Procedures: Optimization and Interaction with Cephalometric and CT-Based Models; Plastic and Reconstructive Surgery; 77(6); pp. 877-885; Jun. 1986.
DCS Dental AG; The CAD/CAM 'DCS Titan System' for Production of Crowns/Bridges; DSC Production; pp. 1-7; Jan. 1992.
Defranco et al.; Three-Dimensional Large Displacement Analysis of Orthodontic Appliances; Journal of Biomechanics; 9(12); pp. 793-801; Jan. 1976.
Dental Institute University of Zurich Switzerland; Program for International Symposium on Computer Restorations: State of the Art of the CEREC-Method; 2 pages; May 1991.
Dentrac Corporation; Dentrac document; pp. 4-13; (year of pub. sufficiently earlier than effective US filing date and any foreign priority date) 1992.
Dent-X; Dentsim . . . Dent-x's virtual reality 3-D training simulator . . . A revolution in dental education; 6 pages; retrieved from the internet (http://www.dent-x.com/DentSim.htm); on Sep. 24, 1998.
Di Muzio et al.; Minimum intensity projection (MinIP); 6 pages; retrieved from the internet (https://radiopaedia.org/articles/minimum-intensity-projection-minip) on Sep. 6, 2018.
Doyle; Digital Dentistry; Computer Graphics World; pp. 50-52 andp. 54; Oct. 2000.
Dummer et al.; Computed Radiography Imaging Based on High-Density 670 nm VCSEL Arrays; International Society for Optics and Photonics; vol. 7557; p. 75570H; 7 pages; (Author Manuscript); Feb. 24, 2010.
Duret et al.; CAD/CAM Imaging in Dentistry; Current Opinion in Dentistry; 1(2); pp. 150-154; Apr. 1991.
Duret et al; CAD-CAM in Dentistry; Journal of the American Dental Association; 117(6); pp. 715-720; Nov. 1988.
Duret; The Dental CAD/CAM, General Description of the Project; Hennson International Product Brochure, 18 pages; Jan. 1986.
Duret; Vers Une Prosthese Informatisee; Tonus; 75(15); pp. 55-57; (English translation attached); 23 pages; Nov. 15, 1985.
Economides; The Microcomputer in the Orthodontic Office; Journal of Clinical Orthodontics; 13(11); pp. 767-772; Nov. 1979.
Ellias et al.; Proteomic analysis of saliva identifies potential biomarkers for orthodontic tooth movement; The Scientific World Journal; vol. 2012; Article ID 647240; dio:10.1100/2012/647240; 7 pages; (year of pub. sufficiently earlier than effective US filing date and any foreign priority date) 2012.

(56) References Cited

OTHER PUBLICATIONS

Elsasser; Some Observations on the History and Uses of the Kesling Positioner; American Journal of Orthodontics; 36(5); pp. 368-374; May 1, 1950.

English translation of Japanese Laid-Open Publication No. 63-11148 to inventor T. Ozukuri (Laid-Open on Jan. 18, 1998) pp. 1-7.

Faber et al.; Computerized Interactive Orthodontic Treatment Planning; American Journal of Orthodontics; 73(1); pp. 36-46; Jan. 1978.

Felton et al.; A Computerized Analysis of the Shape and Stability of Mandibular Arch Form; American Journal of Orthodontics and Dentofacial Orthopedics; 92(6); pp. 478-483; Dec. 1987.

Florez-Moreno; Time-related changes in salivary levels of the osteotropic factors sRANKL and OPG through orthodontic tooth movement; American Journal of Orthodontics and Dentofacial Orthopedics; 143(1); pp. 92-100; Jan. 2013.

Friede et al.; Accuracy of Cephalometric Prediction in Orthognathic Surgery; Journal of Oral and Maxillofacial Surgery; 45(9); pp. 754-760; Sep. 1987.

Futterling et al.; Automated Finite Element Modeling of a Human Mandible with Dental Implants; JS WSCG '98—Conference Program; 8 pages; retrieved from the Internet (https://dspace5.zcu.cz/bitstream/11025/15851/1/Strasser_98.pdf); on Aug. 21, 2018.

Gao et al.; 3-D element Generation for Multi-Connected Complex Dental and Mandibular Structure; IEEE Proceedings International Workshop in Medical Imaging and Augmented Reality; pp. 267-271; Jun. 12, 2001.

GIM-ALLDENT Deutschland, "Das DUX System: Die Technik," 3 pages; (English Translation Included); (year of pub. sufficiently earlier than effective US filing date and any foreign priority date); 2002.

Gottleib et al.; JCO Interviews Dr. James A. McNamura, Jr., on the Frankel Appliance: Part 2: Clinical 1-1 Management; Journal of Clinical Orthodontics; 16(6); pp. 390-407; retrieved from the internet (http://www.jco-online.com/archive/print_article.asp?Year=1982&Month=06&ArticleNum+); 21 pages; Jun. 1982.

Grayson; New Methods for Three Dimensional Analysis of Craniofacial Deformity, Symposium: Computerized Facial Imaging in Oral and Maxillofacial Surgery; American Association of Oral and Maxillofacial Surgeons; 48(8) suppl 1; pp. 5-6; Sep. 13, 1990.

Guess et al.; Computer Treatment Estimates in Orthodontics and Orthognathic Surgery; Journal of Clinical Orthodontics; 23(4); pp. 262-268; 11 pages; (Author Manuscript); Apr. 1989.

Heaven et al.; Computer-Based Image Analysis of Artificial Root Surface Caries; Abstracts of Papers #2094; Journal of Dental Research; 70:528; (Abstract Only); Apr. 17-21, 1991.

Highbeam Research; Simulating stress put on jaw. (ANSYS Inc.'s finite element analysis software); 2 pages; retrieved from the Internet (http://static.highbeam.eom/t/toolingampproduction/november011996/simulatingstressputonfa..); on Nov. 5, 2004.

Hikage; Integrated Orthodontic Management System for Virtual Three-Dimensional Computer Graphic Simulation and Optical Video Image Database for Diagnosis and Treatment Planning; Journal of Japan KA Orthodontic Society; 46(2); pp. 248-269; 56 pages; (English Translation Included); Feb. 1987.

Hoffmann et al.; Role of Cephalometry for Planning of Jaw Orthopedics and Jaw Surgery Procedures; Informatbnen, pp. 375-396; (English Abstract Included); Mar. 1991.

Hojjatie et al.; Three-Dimensional Finite Element Analysis of Glass-Ceramic Dental Crowns; Journal of Biomechanics; 23(11); pp. 1157-1166; Jan. 1990.

Huckins; CAD-CAM Generated Mandibular Model Prototype from MRI Data; AAOMS, p. 96; (Abstract Only); (year of pub. sufficiently earlier than effective US filing date and any foreign priority date) 1999.

JCO Interviews; Craig Andreiko, DDS, MS on the Elan and Orthos Systems; Interview by Dr. Larry W. White; Journal of Clinical Orthodontics; 28(8); pp. 459-468; 14 pages; (Author Manuscript); Aug. 1994.

JCO Interviews; Dr. Homer W. Phillips on Computers in Orthodontic Practice, Part 2; Journal of Clinical Orthodontics; 17(12); pp. 819-831; 19 pages; (Author Manuscript); Dec. 1983.

Jerrold; The Problem, Electronic Data Transmission and the Law; American Journal of Orthodontics and Dentofacial Orthopedics; 113(4); pp. 478-479; 5 pages; (Author Manuscript); Apr. 1998.

Jones et al.; An Assessment of the Fit of a Parabolic Curve to Pre- and Post-Treatment Dental Arches; British Journal of Orthodontics; 16(2); pp. 85-93; May 1989.

Kamada et.al.; Case Reports on Tooth Positioners Using LTV Vinyl Silicone Rubber; J. Nihon University School of Dentistry; 26(1); pp. 11-29; (year of pub. sufficiently earlier than effective US filing date and any foreign priority date) 1984.

Kamada et.al.; Construction of Tooth Positioners with LTV Vinyl Silicone Rubber and Some Case KJ Reports; J. Nihon University School of Dentistry; 24(1); pp. 1-27; (year of pub. sufficiently earlier than effective US filing date and any foreign priority date) 1982.

Kanazawa et al.; Three-Dimensional Measurements of the Occlusal Surfaces of Upper Molars in a Dutch Population; Journal of Dental Research; 63(11); pp. 1298-1301; Nov. 1984.

Kesling et al.; The Philosophy of the Tooth Positioning Appliance; American Journal of Orthodontics and Oral surgery; 31(6); pp. 297-304; Jun. 1945.

Kesling; Coordinating the Predetermined Pattern and Tooth Positioner with Conventional Treatment; American Journal of Orthodontics and Oral Surgery; 32(5); pp. 285-293; May 1946.

Kleeman et al.; The Speed Positioner; J. Clin. Orthod.; 30(12); pp. 673-680; Dec. 1996.

Kochanek; Interpolating Splines with Local Tension, Continuity and Bias Control; Computer Graphics; 18(3); pp. 33-41; Jan. 1, 1984.

Kunii et al.; Articulation Simulation for an Intelligent Dental Care System; Displays; 15(3); pp. 181-188; Jul. 1994.

Kuroda et al.; Three-Dimensional Dental Cast Analyzing System Using Laser Scanning; American Journal of Orthodontics and Dentofacial Orthopedics; 110(4); pp. 365-369; Oct. 1996.

Laurendeau et al.; A Computer-Vision Technique for the Acquisition and Processing of 3-D Profiles of 7 Dental Imprints: An Application in Orthodontics; IEEE Transactions on Medical Imaging; 10(3); pp. 453-461; Sep. 1991.

Leinfelder et al.; A New Method for Generating Ceramic Restorations: a CAD-CAM System; Journal of the American Dental Association; 118(6); pp. 703-707; Jun. 1989.

Manetti et al.; Computer-Aided Cefalometry and New Mechanics in Orthodontics; Fortschr Kieferorthop; 44; pp. 370-376; 8 pages; (English Article Summary Included); (year of pub. sufficiently earlier than effective US filing date and any foreign priority date) 1983.

McCann; Inside the ADA; J. Amer. Dent. Assoc, 118:286-294; Mar. 1989.

McNamara et al.; Invisible Retainers; J. Clin Orthod.; pp. 570-578; 11 pages; (Author Manuscript); Aug. 1985.

McNamara et al.; Orthodontic and Orthopedic Treatment in the Mixed Dentition; Needham Press; pp. 347-353; Jan. 1993.

Moermann et al, Computer Machined Adhesive Porcelain Inlays: Margin Adaptation after Fatigue Stress; IADR Abstract 339; J. Dent. Res.; 66(a):763; (Abstract Only); (year of pub. sufficiently earlier than effective US filing date and any foreign priority date) 1987.

Moles; Correcting Mild Malalignments—As Easy as One, Two, Three; AOA/Pro Corner; 11(2); 2 pages; (year of pub. sufficiently earlier than effective US filing date and any foreign priority date) 2002.

Mormann et al.; Marginale Adaptation von adhasuven Porzellaninlays in vitro; Separatdruck aus:Schweiz. Mschr. Zahnmed.; 95; pp. 1118-1129; 8 pages; (Machine Translated English Abstract); (year of pub. sufficiently earlier than effective US filing date and any foreign priority date); 1985.

Nahoum; The Vacuum Formed Dental Contour Appliance; N. Y. State Dent. J.; 30(9); pp. 385-390; Nov. 1964.

Nash; CEREC CAD/CAM Inlays: Aesthetics and Durability in a Single Appointment; Dentistry Today; 9(8); pp. 20, 22-23 and 54; Oct. 1990.

(56) References Cited

OTHER PUBLICATIONS

Nishiyama et al.; A New Construction of Tooth Repositioner by LTV Vinyl Silicone Rubber; The Journal of Nihon University School of Dentistry; 19(2); pp. 93-102 (year of pub. sufficiently earlier than effective US filing date and any foreign priority date) 1977.
Ogawa et al.; Mapping, profiling and clustering of pressure pain threshold (PPT) in edentulous oral muscosa; Journal of Dentistry; 32(3); pp. 219-228; Mar. 2004.
Ogimoto et al.; Pressure-pain threshold determination in the oral mucosa; Journal of Oral Rehabilitation; 29(7); pp. 620-626; Jul. 2002.
Paul et al.; Digital Documentation of Individual Human Jaw and Tooth Forms for Applications in Orthodontics; Oral Surgery and Forensic Medicine Proc. of the 24th Annual Conf. of the IEEE Industrial Electronics Society (IECON '98); vol. 4; pp. 2415-2418; Sep. 4, 1998.
Pinkham; Foolish Concept Propels Technology; Dentist, 3 pages, Jan./Feb. 1989.
Pinkham; Inventor's CAD/CAM May Transform Dentistry; Dentist; pp. 1 and 35, Sep. 1990.
Ponitz; Invisible retainers; Am. J. Orthod.; 59(3); pp. 266-272; Mar. 1971.
Procera Research Projects; Procera Research Projects 1993 ' Abstract Collection; 23 pages; (year of pub. sufficiently earlier than effective US filing date and any foreign priority date) 1993.
Proffit et al.; The first stage of comprehensive treatment alignment and leveling; Contemporary Orthodontics, 3rd Ed.; Chapter 16; Mosby Inc.; pp. 534-537; (year of pub. sufficiently earlier than effective US filing date and any foreign priority date) 2000.
Proffit et al.; The first stage of comprehensive treatment: alignment and leveling; Contemporary Orthodontics; (Second Ed.); Chapter 15, MosbyYear Book; St. Louis, Missouri; pp. 470-533 Oct. 1993.
Raintree Essix & ARS Materials, Inc., Raintree Essix, Technical Magazine Table of contents and Essix Appliances, 7 pages; retrieved from the internet (http://www.essix.com/magazine/defaulthtml) on Aug. 13, 1997.
Redmond et al.; Clinical Implications of Digital Orthodontics; American Journal of Orthodontics and Dentofacial Orthopedics; 117(2); pp. 240-242; Feb. 2000.
Rekow et al.; CAD/CAM for Dental Restorations—Some of the Curious Challenges; IEEE Transactions on Biomedical Engineering; 38(4); pp. 314-318; Apr. 1991.
Rekow et al.; Comparison of Three Data Acquisition Techniques for 3-D Tooth Surface Mapping; Annual International Conference of the IEEE Engineering in Medicine and Biology Society; 13(1); pp. 344-345 (year of pub. sufficiently earlier than effective US filing date and any foreign priority date) 1991.
Rekow; A Review of the Developments in Dental CAD/CAM Systems; Current Opinion in Dentistry; 2; pp. 25-33; Jun. 1992.
Rekow; CAD/CAM in Dentistry: A Historical Perspective and View of the Future; Journal Canadian Dental Association; 58(4); pp. 283, 287-288; Apr. 1992.
Rekow; Computer-Aided Design and Manufacturing in Dentistry: A Review of the State of the Art; Journal of Prosthetic Dentistry; 58(4); pp. 512-516; Dec. 1987.
Rekow; Dental CAD-CAM Systems: What is the State of the Art?; The Journal of the American Dental Association; 122(12); pp. 43-48; Dec. 1991.
Rekow; Feasibility of an Automated System for Production of Dental Restorations, Ph.D. Thesis; Univ. of Minnesota, 250 pages, Nov. 1988.
Richmond et al.; The Development of the PAR Index (Peer Assessment Rating): Reliability and Validity.; The European Journal of Orthodontics; 14(2); pp. 125-139; Apr. 1992.
Richmond et al.; The Development of a 3D Cast Analysis System; British Journal of Orthodontics; 13(1); pp. 53-54; Jan. 1986.
Richmond; Recording the Dental Cast in Three Dimensions; American Journal of Orthodontics and Dentofacial Orthopedics; 92(3); pp. 199-206; Sep. 1987.

Rudge; Dental Arch Analysis: Arch Form, a Review of the Literature; The European Journal of Orthodontics; 3(4); pp. 279-284; Jan. 1981.
Sakuda et al.; Integrated Information-Processing System in Clinical Orthodontics: An Approach with Use of a Computer Network System; American Journal of Orthodontics and Dentofacial Orthopedics; 101(3); pp. 210-220; 20 pages; (Author Manuscript) Mar. 1992.
Schellhas et al.; Three-Dimensional Computed Tomography in Maxillofacial Surgical Planning; Archives of Otolaryngology—Head and Neck Surgery; 114(4); pp. 438-442; Apr. 1988.
Schroeder et al; Eds. The Visual Toolkit, Prentice Hall PTR, New Jersey; Chapters 6, 8 & 9, (pp. 153-210,309-354, and 355-428; (year of pub. sufficiently earlier than effective US filing date and any foreign priority date) 1998.
Shilliday; Minimizing finishing problems with the mini-positioner; American Journal of Orthodontics; 59(6); pp. 596-599; Jun. 1971.
Shimada et al.; Application of optical coherence tomography (OCT) for diagnosis of caries, cracks, and defects of restorations; Current Oral Health Reports; 2(2); pp. 73-80; Jun. 2015.
Siemens; CEREC—Computer-Reconstruction, High Tech in der Zahnmedizin; 15 pagesl; (Includes Machine Translation); (year of pub. sufficiently earlier than effective US filing date and any foreign priority date); 2004.
Sinclair; The Readers' Corner; Journal of Clinical Orthodontics; 26(6); pp. 369-372; 5 pages; retrived from the internet (http://www.jco-online.com/archive/print_article.asp?Year=1992&Month=06&ArticleNum=); Jun. 1992.
Sirona Dental Systems GmbH, CEREC 3D, Manuel utiiisateur, Version 2.0X (in French); 114 pages; (English translation of table of contents included); (year of pub. sufficiently earlier than effective US filing date and any foreign priority date); 2003.
Stoll et al.; Computer-aided Technologies in Dentistry; Dtsch Zahna'rztl Z 45, pp. 314-322; (English Abstract Included); (year of pub. sufficiently earlier than effective US filing date and any foreign priority date) 1990.
Sturman; Interactive Keyframe Animation of 3-D Articulated Models; Proceedings Graphics Interface '84; vol. 86; pp. 35-40; May-Jun. 1984.
The American Heritage, Stedman's Medical Dictionary; Gingiva; 3 pages; retrieved from the interent (http://reference.com/search/search?q=gingiva) on Nov. 5, 2004.
The Dental Company Sirona: Cerc omnicam and cerec bluecam brochure: The first choice in every case; 8 pages; (year of pub. sufficiently earlier than effective US filing date and any foreign priority date) 2014.
Thorlabs; Pellin broca prisms; 1 page; retrieved from the internet (www.thorlabs.com); Nov. 30, 2012.
Tiziani et al.; Confocal principle for macro and microscopic surface and defect analysis; Optical Engineering; 39(1); pp. 32-39; Jan. 1, 2000.
Truax; Truax Clasp-Less(TM) Appliance System; The Functional Orthodontist; 9(5); pp. 22-24, 26-8; Sep.-Oct. 1992.
TRU-TATN Orthodontic & Dental Supplies, Product Brochure, Rochester, Minnesota 55902, 16 pages; (year of pub. sufficiently earlier than effective US filing date and any foreign priority date) 1996.
U.S. Department of Commerce, National Technical Information Service, Holodontography: An Introduction to Dental Laser Holography; School of Aerospace Medicine Brooks AFB Tex; Mar. 1973, 40 pages; Mar. 1973.
U.S. Department of Commerce, National Technical Information Service; Automated Crown Replication Using Solid Photography SM; Solid Photography Inc., Melville NY,; 20 pages; Oct. 1977.
Vadapalli; Minimum intensity projection (MinIP) is a data visualization; 7 pages; retrieved from the internet (https://prezi.com/tdmttnmv2knw/minimum-intensity-projection-minip-is-a-data-visualization/) on Sep. 6, 2018.
Van Der Linden et al.; Three-Dimensional Analysis of Dental Casts by Means of the Optocom; Journal of Dental Research; 51(4); p. 1100; Jul.-Aug. 1972.

(56) References Cited

OTHER PUBLICATIONS

Van Der Linden; A New Method to Determine Tooth Positions and Dental Arch Dimensions; Journal of Dental Research; 51(4); p. 1104; Jul.-Aug. 1972.
Van Der Zel; Ceramic-Fused-to-Metal Restorations with a New CAD/CAM System; Quintessence International; 24(A); pp. 769-778; (year of pub. sufficiently earlier than effective US filing date and any foreign priority date); 1993.
Van Hilsen et al.; Comparing potential early caries assessment methods for teledentistry; BMC Oral Health; 13(16); doi: 10.1186/1472-6831-13-16; 9 pages; Mar. 2013.
Varady et al.; Reverse Engineering of Geometric Models'An Introduction; Computer-Aided Design; 29(4); pp. 255-268; 20 pages; (Author Manuscript); Apr. 1997.
Verstreken et al.; An Image-Guided Planning System for Endosseous Oral Implants; IEEE Transactions on Medical Imaging; 17(5); pp. 842-852; Oct. 1998.
Warunek et al.; Physical and Mechanical Properties of Elastomers in Orthodonic Positioners; American Journal of Orthodontics and Dentofacial Orthopedics; 95(5); pp. 388-400; 21 pages; (Author Manuscript); May 1989.
Warunek.etal.; Clinical Use of Silicone Elastomer Applicances; JCO; 23(10); pp. 694-700; Oct. 1989.
Watson et al.; Pressures recorded at to denture base-mucosal surface interface in complete denture wearers; Journal of Oral Rehabilitation 14(6); pp. 575-589; Nov. 1987.
Wells; Application of the Positioner Appliance in Orthodontic Treatment; American Journal of Orthodontics; 58(4); pp. 351-366; Oct. 1970.
Williams; Dentistry and CAD/CAM: Another French Revolution; J. Dent. Practice Admin.; 4(1); pp. 2-5 Jan./Mar. 1987.
Williams; The Switzerland and Minnesota Developments in CAD/CAM; Journal of Dental Practice Administration; 4(2); pp. 50-55; Apr./Jun. 1987.
Wishan; New Advances in Personal Computer Applications for Cephalometric Analysis, Growth Prediction, Surgical Treatment Planning and Imaging Processing; Symposium: Computerized Facial Imaging in Oral and Maxilofacial Surgery; p. 5; Presented on Sep. 13, 1990.
Wolf; Three-dimensional structure determination of semi-transparent objects from holographic data; Optics Communications; 1(4); pp. 153-156; Sep. 1969.
WSCG'98—Conference Program, The Sixth International Conference in Central Europe on Computer Graphics and Visualization '98; pp. 1-7; retrieved from the Internet on Nov. 5, 2004, (http://wscg.zcu.cz/wscg98/wscg98.htm); Feb. 9-13, 1998.
Xia et al.; Three-Dimensional Virtual-Reality Surgical Planning and Soft-Tissue Prediction for Orthognathic Surgery; IEEE Transactions on Information Technology in Biomedicine; 5(2); pp. 97-107; Jun. 2001.
Yamamoto et al.; Optical Measurement of Dental Cast Profile and Application to Analysis of Three-Dimensional Tooth Movement in Orthodontics; Front. Med. Biol. Eng., 1(2); pp. 119-130; (year of pub. sufficiently earlier than effective US filing date and any foreign priority date); 1988.
Yamamoto et al.; Three-Dimensional Measurement of Dental Cast Profiles and Its Applications to Orthodontics; Conf. Proc. IEEE Eng. Med. Biol. Soc.; 12(5); pp. 2052-2053; Nov. 1990.
Yamany et al.; A System for Human Jaw Modeling Using Intra-Oral Images; Proc. of the 20th Annual Conf. of the IEEE Engineering in Medicine and Biology Society; vol. 2; pp. 563-566; Oct. 1998.
Yoshii; Research on a New Orthodontic Appliance: The Dynamic Positioner (D.P.); 111. The General Concept of the D.P. Method and Its Therapeutic Effect, Part 1, Dental and Functional Reversed Occlusion Case Reports; Nippon Dental Review; 457; pp. 146-164; 43 pages; (Author Manuscript); Nov. 1980.
Yoshii; Research on a New Orthodontic Appliance: the Dynamic Positioner (D.P.); I. The D.P. Concept and Implementation of Transparent Silicone Resin (Orthocon); Nippon Dental Review; 452; pp. 61-74; 32 pages; (Author Manuscript); Jun. 1980.
Yoshii; Research on a New Orthodontic Appliance: The Dynamic Positioner (D.P.); II. The D.P. Manufacturing Procedure and Clinical Applications; Nippon Dental Review; 454; pp. 107-130; 48 pages; (Author Manuscript); Aug. 1980.
Yoshii; Research on a New Orthodontic Appliance: The Dynamic Positioner (D.P.); III—The General Concept of the D.P. Method and Its Therapeutic Effect, Part 2. Skeletal Reversed Occlusion Case Reports; Nippon Dental Review; 458; pp. 112-129; 40 pages; (Author Manuscript); Dec. 1980.
Riley et al.; U.S. Appl. No. 16/003,841 entitled Palatal expander with skeletal anchorage devices, filed Jun. 8, 2018.
Shanjani et al.; U.S. Appl. No. 16/019,037 entitled "Biosensor performance indicator for intraoral appliances," filed Jun. 26, 2018.
Sato et al.; U.S. Appl. No. 16/041,606 entitled "Palatal contour anchorage," filed Jul. 20, 2018.
Xue et al.; U.S. Appl. No. 16/010,087 entitled "Automatic detection of tooth type and eruption status," filed Jun. 15, 2018.
Sato et al.; U.S. Appl. No. 16/048,054 entitled "Optical coherence tomography for orthodontic aligners," filed Jul. 27, 2018.
Miller et al.; U.S. Appl. No. 16/038,088 entitled "Method and apparatuses for interactive ordering of dental aligners," filed Jul. 17, 2018.
Moalem et al.; U.S. Appl. No. 16/046,897 entitled Tooth shading, transparency and glazing, filed Jul. 26, 2018.
Nyukhtikov et al.; U.S. Appl. No. 15/998,883 entitled "Buccal corridor assessment and computation," filed Aug. 15, 2018.
Arakawa et al; Mouthguard biosensor with telemetry system for monitoring of saliva glucose: A novel cavitas sensor; Biosensors and Bioelectronics; 84; pp. 106-111; Oct. 2016.
O'Leary et al.; U.S. Appl. No. 16/195,701 entitled "Orthodontic retainers," filed Nov. 19, 2018.
Shanjani et al., U.S. Appl. No. 16/206,894 entitled "Sensors for monitoring oral appliances," filed Nov. 28, 2019.
Shanjani et al., U.S. Appl. No. 16/231,906 entitled "Augmented reality enhancements for dental practitioners." filed Dec. 24, 2018.
Kopleman et al., U.S. Appl. No. 16/220,381 entitled "Closed loop adaptive orthodontic treatment methods and apparatuses," filed Dec. 14, 2018.
Sabina et al., U.S. Appl. No. 16/258,516 entitled "Diagnostic Introral Scanning" filed Jan. 25, 2019.
Video of DICOM to Surgical Guides; Can be viewed at <URL:https://youtu.be/47KtOmCEFQk; Published Apr. 4, 2016.
DentalWings; Intraoral scanner; 7 pages; retrieved from the internet (https://web.archive.org/web/20160422114335/http://www.dentalwings.com/products/intraoral-scanner/); available as of Apr. 4, 2016.
DentalWings; I series dental impression scanner; 8 pages; retrieved from the internet (https://web.archive.org/web/20160502145908/http://www.dentalwings.com/products/scan-and-design-systems/iseries/) ; available as of May 2, 2016.
Sobral De Agular et al.; The gingival crevicular fluid as a source of biomarkers to enhance efficiency of orthodontic and functional treatment of growing patients; Bio. Med. Research International; vol. 2017; 7 pages; Article ID 3257235; (year of pub. sufficiently earlier than effective US filing date and any foreign priority date) 2017.
3 Shape Trios 3; Insane speed-scanning with 3shape trios 3 intracral canner; (Screenshot); 2 pages; retrieved from the internet at You Tube (https//www.youtube.com/watch?v=X5CviUZ5DpQ&feature=youtu.be; available as of Sep. 18, 2015.

\* cited by examiner

180° configuration

90° configuration

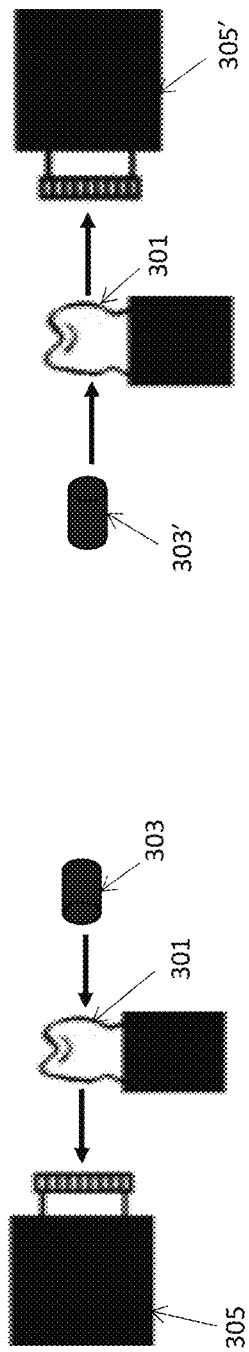
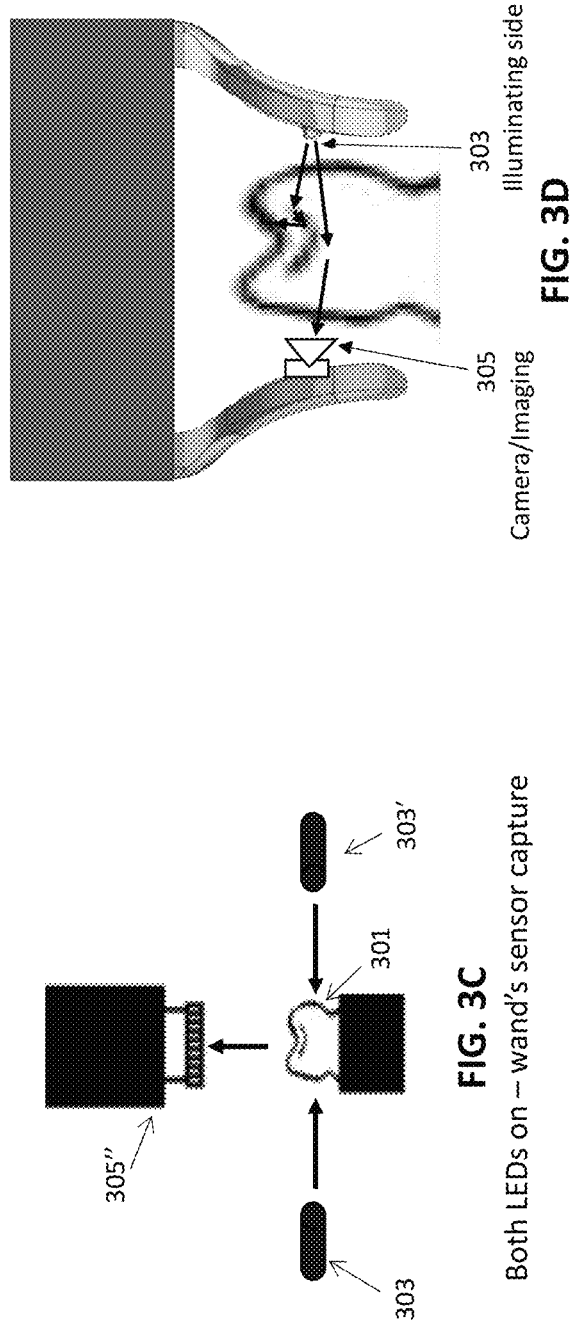

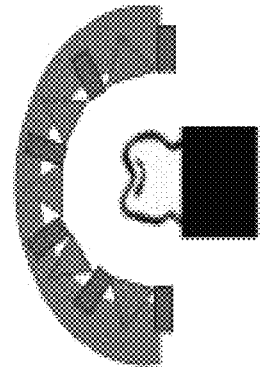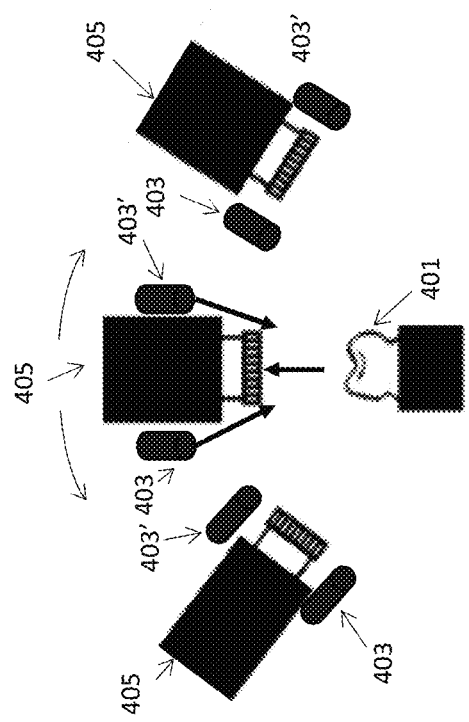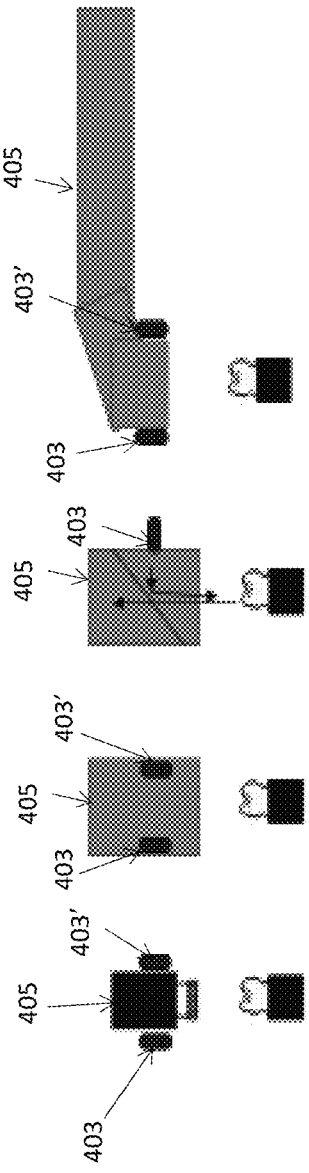

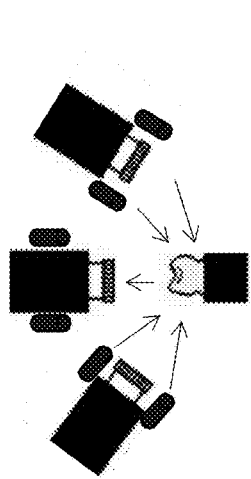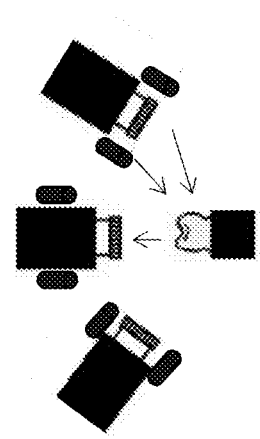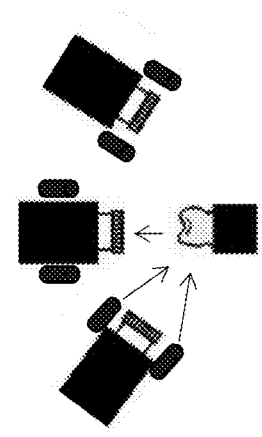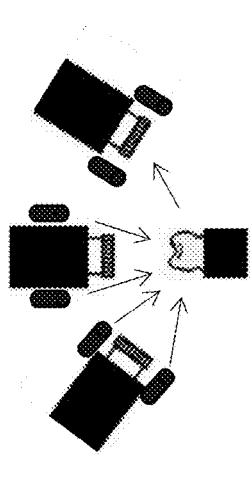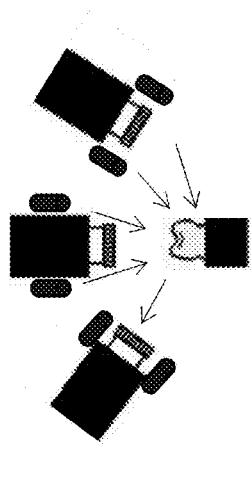
FIG. 5A FIG. 5B FIG. 5C FIG. 5D FIG. 5E FIG. 5F FIG. 5G FIG. 5H FIG. 5I

Bottom View

Front View

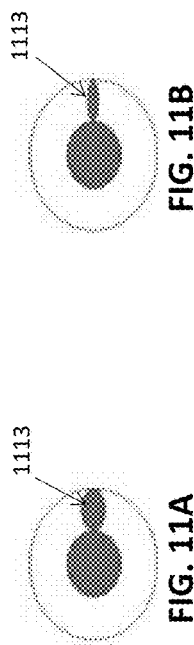
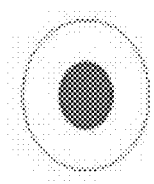
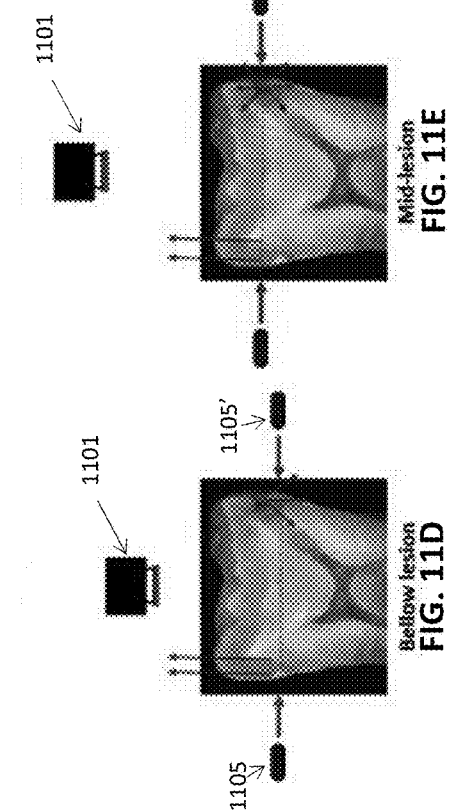
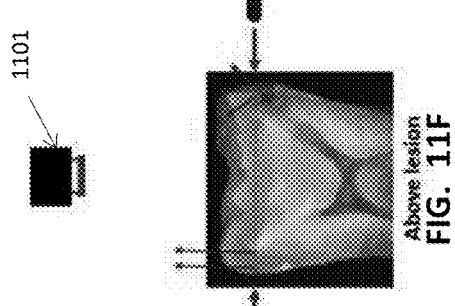
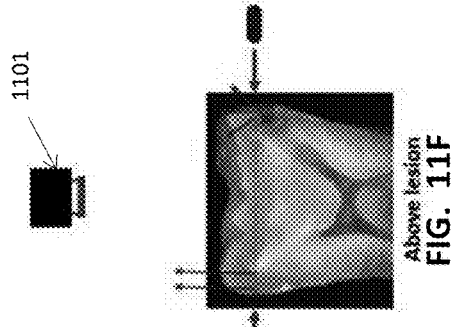
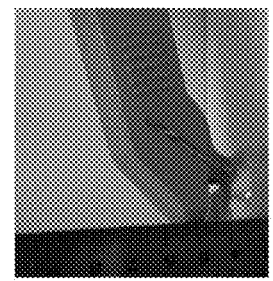
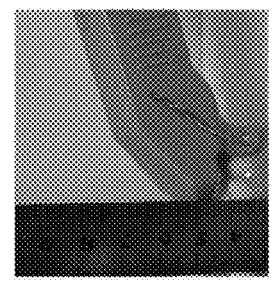
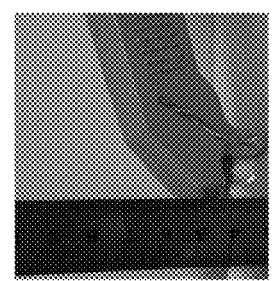
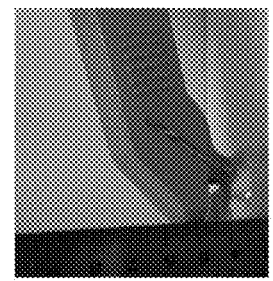

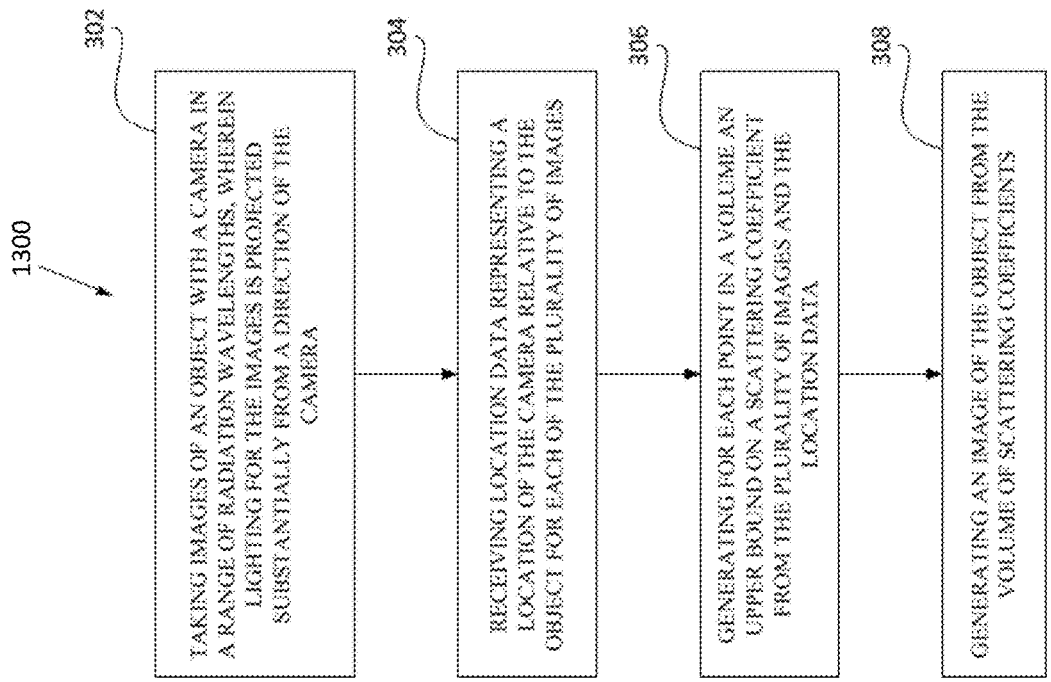

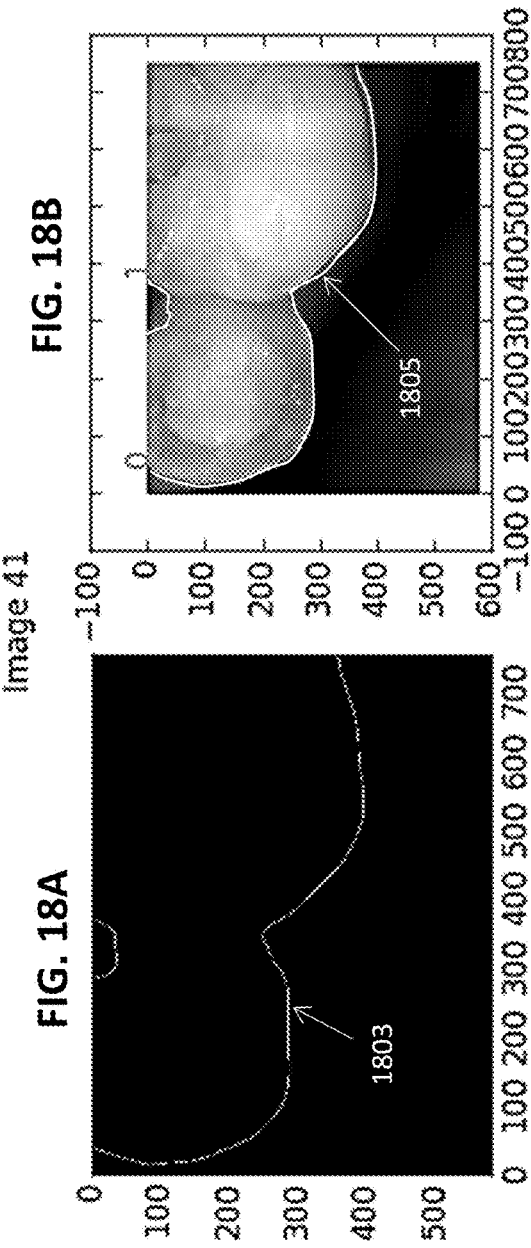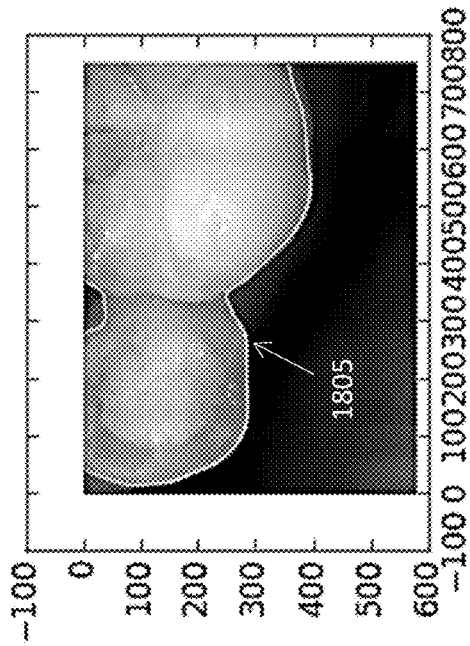
FIG. 18A
FIG. 18B
FIG. 18C

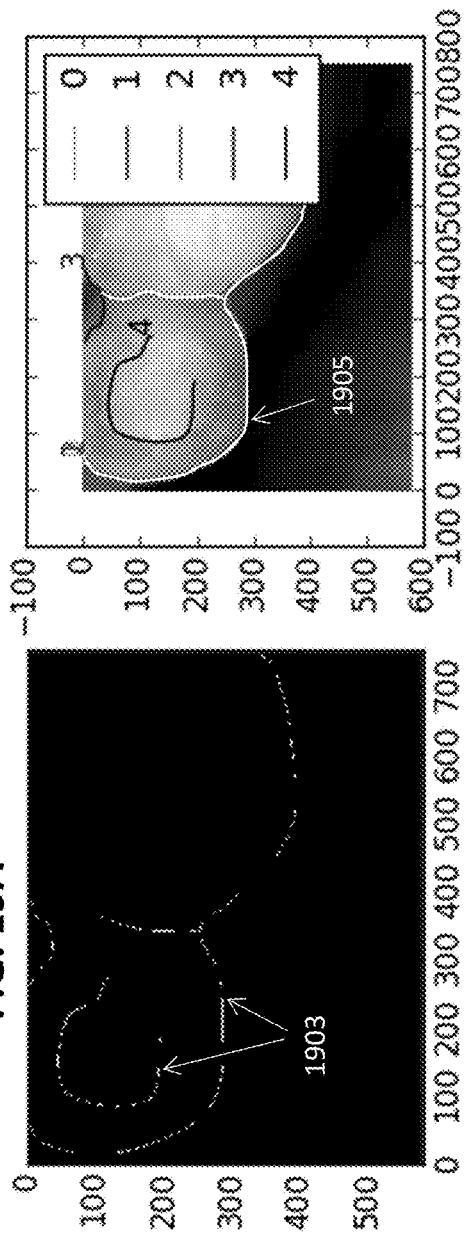

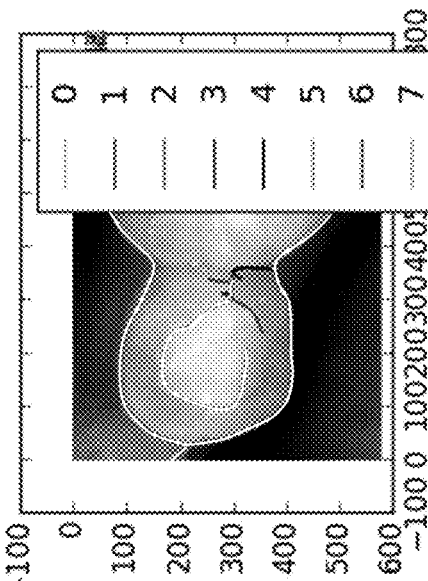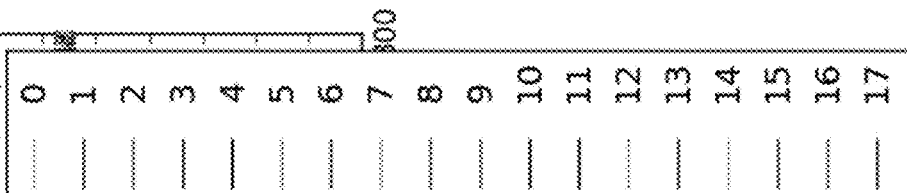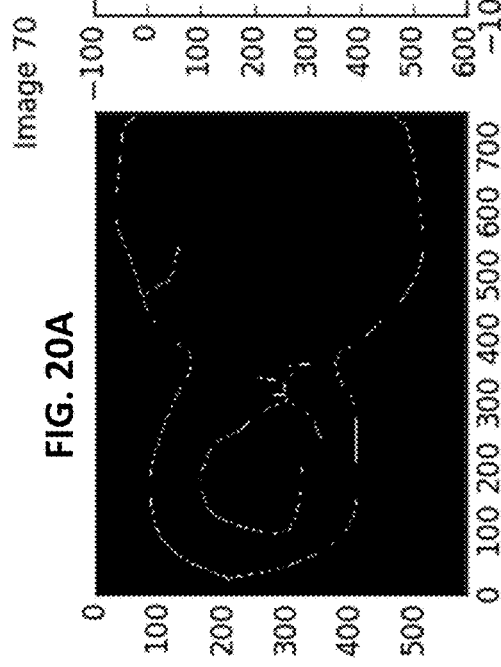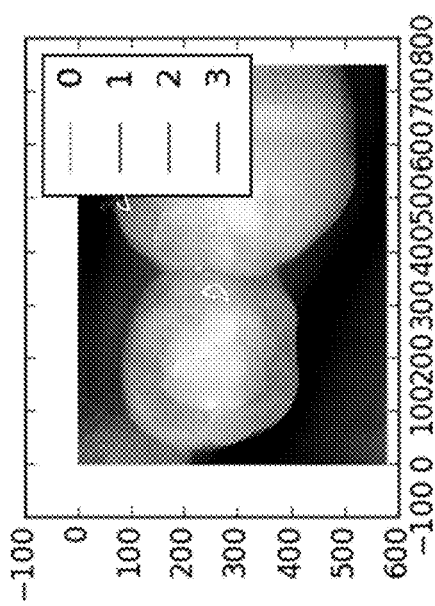
FIG. 20A
FIG. 20B
FIG. 20C

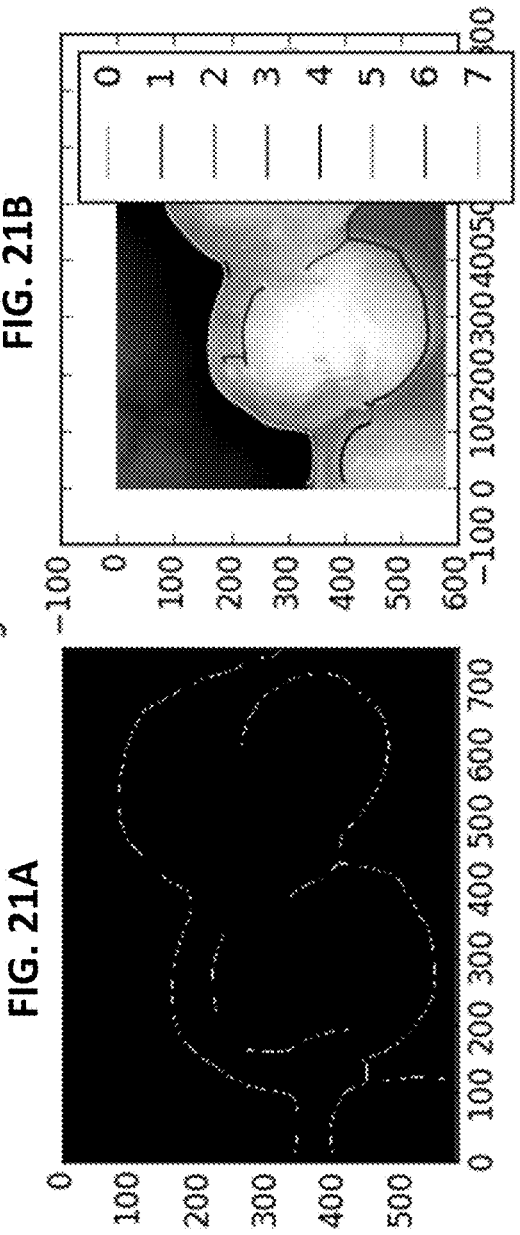
FIG. 21A
FIG. 21B
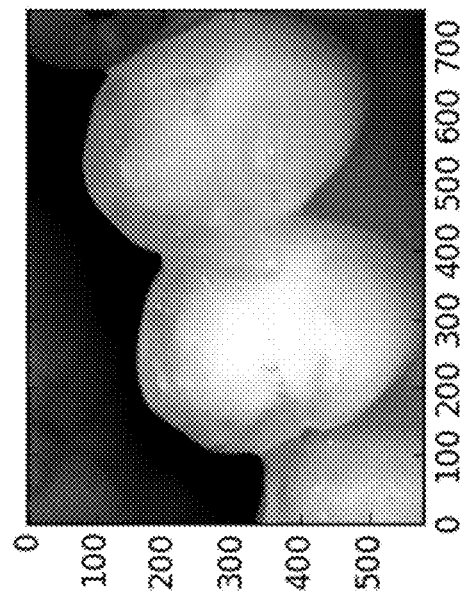
FIG. 21C

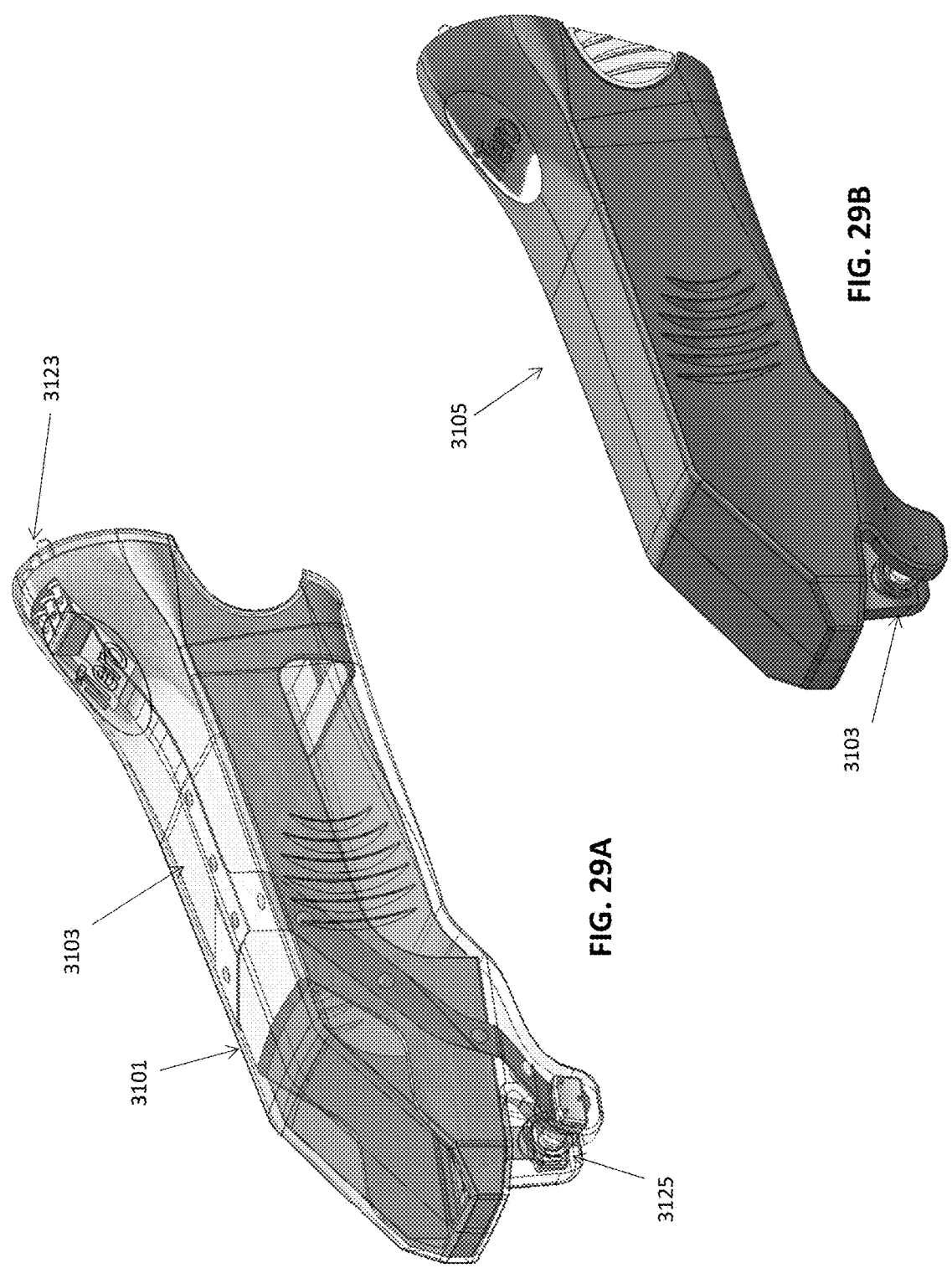

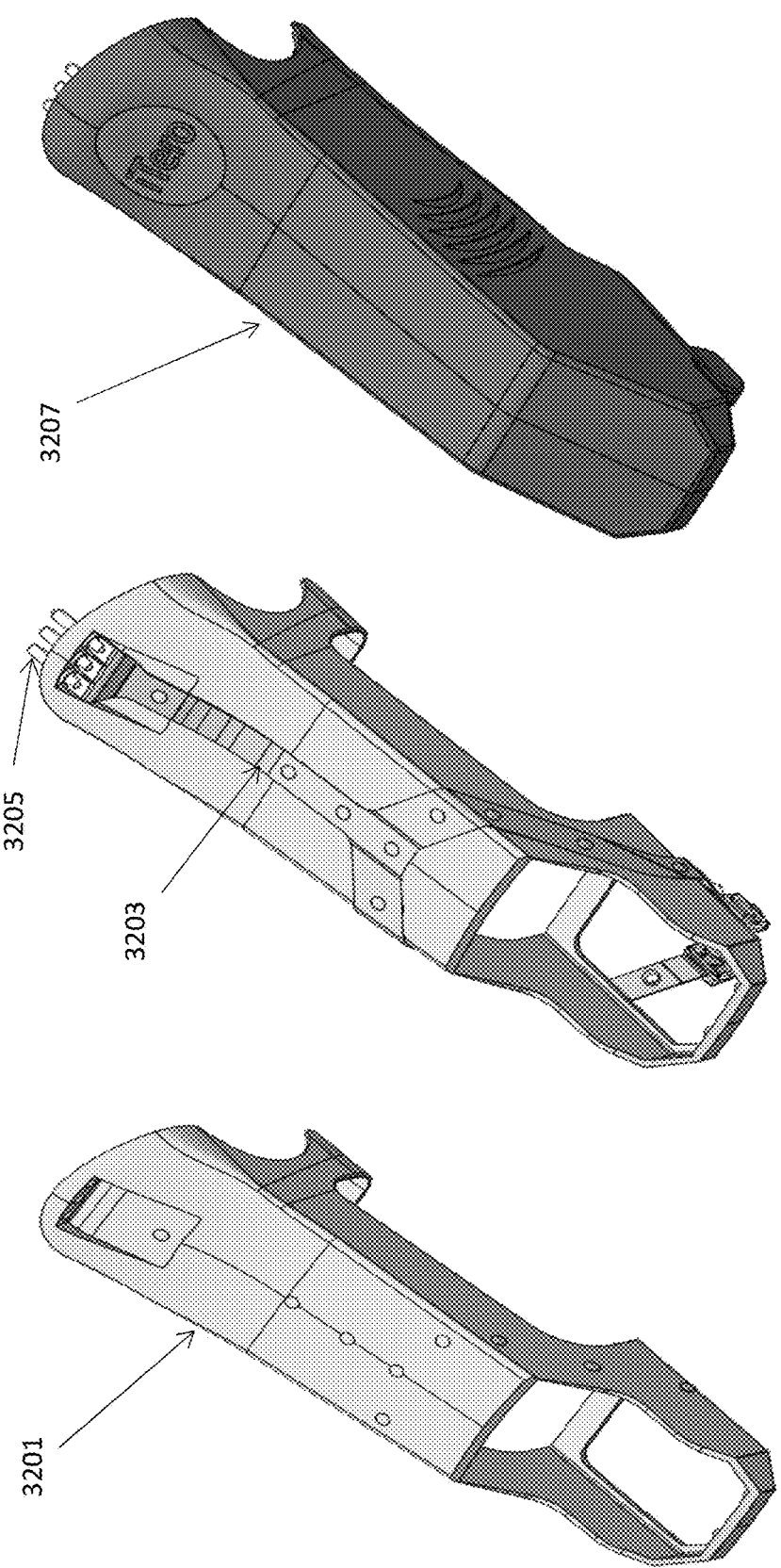

METHODS FOR DENTAL DIAGNOSTICS

CROSS REFERENCE TO RELATED APPLICATIONS

This patent application claims priority as a continuation of U.S. patent application Ser. No. 15/662,234, filed Jul. 27, 2017 and titled "INTRAORAL SCANNER WITH DENTAL DIAGNOSTICS CAPABILITIES," which claims priority to each of: U.S. provisional patent application No. 62/367,607, titled "INTRAORAL SCANNER WITH DENTAL DIAGNOSTICS CAPABILITIES," and filed on Jul. 27, 2016; U.S. provisional patent application No. 62/477,387, titled "INTRAORAL SCANNER WITH DENTAL DIAGNOSTICS CAPABILITIES," filed on Mar. 27, 2017; and U.S. provisional patent application No. 62/517,467, titled "MINIMAL VALUE LIFTING TO FORM A VOLUMETRIC MODEL OF AN OBJECT," filed on Jun. 9, 2017. Each of these patent applications is herein incorporated by reference in its entirety.

This patent application also claims priority as a continuation of U.S. patent application Ser. No. 15/662,250, filed Jul. 27, 2017 and titled "METHODS AND APPARATUSES FOR FORMING A THREE-DIMENSIONAL VOLUMETRIC MODEL OF A SUBJECT'S TEETH", which claims priority to each of: U.S. provisional patent application No. 62/367,607, titled "INTRAORAL SCANNER WITH DENTAL DIAGNOSTICS CAPABILITIES," and filed on Jul. 27, 2016; U.S. provisional patent application No. 62/477,387, titled "INTRAORAL SCANNER WITH DENTAL DIAGNOSTICS CAPABILITIES," filed on Mar. 27, 2017; and U.S. provisional patent application No. 62/517,467, titled "MINIMAL VALUE LIFTING TO FORM A VOLUMETRIC MODEL OF AN OBJECT," filed on Jun. 9, 2017. Each of these patent applications is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The methods and apparatuses described herein may relate to optical scanners, and particularly for generating three-dimensional representations of objects. In particular, described herein are methods and apparatuses that may be useful in scanning, including 3D scanning, and analyzing the intraoral cavity for diagnosis, treatment, longitudinal tracking, tooth measurement, and detection of dental caries and cracks. These methods and apparatuses may generate volumetric models of the internal structure of the teeth, and/or may include color scanning.

BACKGROUND

Many dental and orthodontic procedures can benefit from accurate three-dimensional (3D) descriptions of a patient's dentation and intraoral cavity. In particular, it would be helpful to provide a three-dimensional description of both the surface, and internal structures of the teeth, including the enamel and dentin, as well as caries and the general internal composition of the tooth volume. Although purely surface representations of the 3D surfaces of teeth have proven extremely useful in the design and fabrication of dental prostheses (e.g., crowns or bridges), and treatment plans, the ability to image internal structures including the development of caries and cracks in the enamel and underlying dentin, would be tremendously useful, particularly in conjunction with a surface topographical mapping.

Historically, ionizing radiation (e.g., X-rays) have been used to image into the teeth. For example, X-Ray bitewing radiograms are often used to provide non-quantitative images into the teeth. However, in addition to the risk of ionizing radiation, such images are typically limited in their ability to show features and may involve a lengthy and expensive procedure to take. Other techniques, such as cone beam computed tomography (CBCT) may provide tomographic images, but still require ionizing radiation.

Thus, it would be beneficial to provide methods and apparatuses, including devices and systems, such as intraoral scanning systems, that may be used to model a subject's tooth or teeth and include both external (surface) and internal (within the enamel and dentin) structures and composition using non-ionizing radiation. The model of the subject's teeth may be a 3D volumetric model or a panoramic image. In particular, it would be helpful to provide methods and apparatuses that may use a single apparatus to provide this capability. There is a need for improved methods and systems for scanning an intraoral cavity of a patient, and/or for automating the identification and analysis of dental caries.

SUMMARY OF THE DISCLOSURE

In general, described herein are methods and apparatuses (e.g., devices and systems) for scanning both external and/or internal structures of teeth. These methods and apparatuses may generate a model of a subject's teeth that includes both surface topography and internal features (e.g., dentin, dental fillings, cracks and/or caries). Any of these apparatuses may include intraoral scanners for scanning into or around a subject's oral cavity and that are equipped with a light source or light sources that can illuminate in two or more spectral ranges: a surface-feature illuminating spectral range (e.g., visible light) and a penetrative spectral range (e.g. IR range, and particularly "near-IR," including but not limited to 850 nm). The scanning apparatus may also include one or more sensors for detecting the emitted light and one or more processors for controlling operation of the scanning and for analyzing the received light from both the first spectral range and the second spectral range to generate a model of the subject's teeth including the surface of the teeth and features within the teeth, including within the enamel and dentin. The generated mode may be a 3D volumetric model or a panoramic image.

As used herein, a volumetric model may include a virtual representation of an object in three dimensions in which internal regions (structures, etc.) are arranged within the volume in three physical dimensions in proportion and relative relation to the other internal and surface features of the object which is being modeled. For example, a volumetric representation of a tooth may include the outer surface as well as internal structures within the tooth (beneath the tooth surface) proportionately arranged relative to the tooth, so that a section through the volumetric model would substantially correspond to a section through the tooth, showing position and size of internal structures; a volumetric model may be section from any (e.g., arbitrary) direction and correspond to equivalent sections through the object being modeled. A volumetric model may be electronic or physical. A physical volumetric model may be formed, e.g., by 3D printing, or the like. The volumetric models described herein may extend into the volume completely (e.g., through the entire volume, e.g., the volume of the teeth) or partially (e.g., into the volume being modeled for some minimum depth, e.g., 2 mm, 3 mm, 4 mm, 5 mm, 6 mm, 7 mm, 8 mm, 9 mm, 10 mm, 12 mm, etc.).

The methods described herein typically include methods for generating a model of a subject's teeth typically generating a 3D model or rending of the teeth that include both surface and internal features. Non-ionizing methods of imaging and/or detecting internal structures may be used, such as taking images using a penetrating wavelength to view structures within the teeth by illuminating them using one or more penetrative spectral ranges (wavelengths), including using trans-illumination (e.g., illuminating from one side and capturing light from the opposite side after passing through the object), and/or small-angle penetration imaging (e.g., reflective imaging, capturing light that has been reflected/scattered from internal structures when illuminating with a penetrating wavelength). In particular, multiple penetration images may be taken from the same relative position. Although traditional penetration imaging techniques (e.g., trans-illumination) may be used, in which the angle between the light emitter illumination direction and the detector (e.g., camera) view angle is 90 degrees or 180 degrees, also described herein are methods and apparatuses in which the angle is much smaller (e.g., between 0 degrees and 25 degrees, between 0 degrees and 20 degrees, between 0 degrees and 15 degrees, between 0 degrees and 10 degrees, etc.). Smaller angles (e.g., 0-15°) may be particularly beneficial because the illumination (light source) and sensing (detector(s), e.g., camera(s), etc.) may be closer to each other, and may provide a scanning wand for the intraoral scanner that can be more easily positioned and moved around a subject's teeth. These small-angle penetration images and imaging techniques may also be referred to herein as reflective illumination and/or imaging, or as reflective/scattering imaging. In general penetrating imaging may refer to any appropriate type of penetrating imaging unless otherwise specified, including trans-illumination, small-angle penetration imaging, etc. However, small small angles may also result in direct reflection from the surface of the object (e.g., teeth), which may obscure internal structures.

The methods and apparatuses described here are particularly effective in combining a 3D surface model of the tooth or teeth with the imaged internal features such as lesions (caries, cracks, etc.) that may be detected by the use of penetration imaging by using an intraoral scanner that is adapted for separate but concurrent (or nearly-concurrent) detection of both the surface and internal features. Combining surface scanning and the penetration imaging may be performed by alternating or switching between these different modalities in a manner that allows the use of the same coordinate system for the two. Alternatively, both surface and penetrative scanning may be simultaneously viewed, for example, by selectively filtering the wavelengths imaged to separate the IR (near-IR) light from the visible light. The 3D surface data may therefore provide important reference and angle information for the internal structures, and may allow the interpretation and analysis of the penetrating images that may otherwise be difficult or impossible to interpret.

For example, described herein are methods for generating a model of a subject's teeth including the steps of: capturing three-dimensional (3D) surface model data of at least a portion of a subject's tooth using an intraoral scanner; taking a plurality of images into the tooth using a penetrative wavelength with the intraoral scanner; and forming a 3D model of the tooth including internal structure using the 3D surface model data and the plurality of images.

A method for generating a model of a subject's teeth may include: capturing three-dimensional (3D) surface model data of at least a portion of a subject's tooth with an intraoral scanner operating in a first imaging modality, wherein the 3D surface model data has a first coordinate system; taking a plurality of images into the tooth with the intraoral scanner operating in a second imaging modality using a penetrative wavelength, wherein the plurality of images reference the first coordinate system; and forming a 3D model of the tooth including internal structures using the 3D surface model data and the plurality of images. In general, the capturing the first wavelength does not necessarily capture images, but may directly capture a 3D surface scan. The second penetrating modalities may be captured as images processed as described herein.

In general, capturing the 3D surface model data may include determining a 3D surface topology using any appropriate method. For example, determining a 3D surface topology may include using confocal focusing. Capturing the 3D surface model data may comprise using on or more of: confocal scanning, stereo vision or structured light triangulation.

Any of the methods and apparatuses described herein may be used to model, image and/or render a 3D image of a single tooth or region of a tooth, multiple teeth, teeth and gums, or other intraoral structures, particularly from within a subject's mouth.

In general, the methods and apparatuses for performing them described herein include 3D color intraoral scanning/scanners. For example, the methods may include capturing color intraoral 3D data.

As will be described in greater detail below, the method and apparatuses may control the switching between collecting surface data and collecting penetration imaging (penetrative) data. For example, any of these methods may include taking images using the penetrative wavelength as the 3D surface model data is being captured, e.g., by switching between the first imaging modality and the second (penetrative) imaging modality.

The same sensor or a different sensor may be used to collect the surface and internal feature data. For example, taking the plurality of images may comprise using a same sensor on the intraoral scanner to capture 3D surface model data and the plurality of images using the penetrative wavelength. Alternatively, a separate sensor or sensors may be used. For example, taking the plurality of images may comprise using a different sensor on the intraoral scanner to capture 3D surface model data and the plurality of images using the penetrative wavelength.

As mentioned, taking images of the tooth using the penetrative wavelength (or penetrative spectral range) may include taking penetration images at any angle between the illumination source and the sensor (e.g., detector or camera). In particular, internal feature (e.g., reflective imaging) data may be imaged using a small angle configuration, in which one or preferably more penetration images are taken at different orientations relative to the tooth/teeth. For example, taking the plurality of images may comprise illuminating the tooth at an angle of between 0° and 15° relative to a sensor (e.g., detector, camera, etc.) receiving the illumination from the tooth, reflecting off of the internal composition of the tooth/teeth. Taking the plurality of images (e.g., penetration images such as these small-angle penetration images) generally includes taking one or more (e.g., a plurality, including two or more, three or more, etc.) penetration images at different angles of the intraoral scanner relative to the tooth over the same region of the tooth. Thus, the same internal region of the tooth will appear in multiple different scans from different angles.

In general, any number of sensors may be included on the intraoral scanner, e.g., the wand of the intraoral scanner. Any appropriate sensor for detecting and recording the appropriate spectral range(s) (e.g., of light) may be used. Sensors may be referred to and may include detectors, cameras, and the like. For example, taking a plurality of images may comprise using a plurality of sensors on the intraoral scanner to capture the plurality of images using the penetrative wavelength.

The illumination used to take a penetration image is generally penetrative, so that it may at least partially penetrate and pass through the enamel and dentin of the teeth. Penetrative wavelengths of light may include generally infrared (and particularly near infrared) light. For example, light in the range of 700 to 1090 nm (e.g., 850 nm) may be used. Other wavelengths and ranges of wavelengths may be used, including wavelengths shorter than the visible spectrum. Thus, taking the plurality of images may comprise illuminating the tooth with infrared light. Taking the plurality of images (e.g., penetration images) may include illuminating the tooth with one or more of white light (including but not limited to white light trans-illumination), UV/Blue fluorescence and red light fluorescence.

The illumination used to take a penetration image can be considered semi-penetrative in the sense that internal tooth regions (e.g., points or voxels) may be visible from only a few camera positions and orientations; the point may be obstructed by other structures in some images which include the volume point in their field of view. In that sense, images that include the volume point in their field of view may not image this volume point. Thus, the methods and apparatuses described herein may take into account the high masking of volume points, unlike other penetrative scanning techniques such as CT, which uses X-ray imaging in which no masking occurs.

In general, any appropriate technique may be used to form the 3D models of the tooth including the (combined) surface and internal structures from the penetration imaging. These 3D models may be referred to as combined 3D surface/volume models, 3D volumetric surface models, or simply "3D models," or the like. As mentioned, both the surface data and the penetration imaging data may generally be in the same coordinate system. The two may be combined by using the common coordinate system. In some variations the surface data may be expressed as a surface model and the internal features added to this model. In some variations the data may be reconstructed into a three-dimensional model concurrently (after adding together). One or both datasets may be separately modified (e.g., filtered, subtracted, etc.). For example, forming the 3D model of the tooth including internal structures may comprise combing the 3D surface model data with an internal structure data (including volumetric data). Forming the 3D model of the tooth including internal structures may comprise combining the plurality of penetration images, wherein the plurality of penetration images may be taken from different angles using the intraoral scanner.

In any of the methods and apparatuses configured to perform these methods described herein, the data may be analyzed automatically or manually by the system. In particular, the method and apparatuses described herein may include examining internal features and/or identifying features of interest, including crack and caries. Features may be recognized based on feature-recognition criterion (e.g., dark or light regions in the penetration images), pattern-recognition, machine learning, or the like. Features may be marked, including coloring, labeling or the like. Feature may be marked directly in the 3D model, on the penetration image, or in a data structure that references (e.g., shares a coordinate system with) the 3D model of the tooth formed by the methods and apparatuses described herein.

Also described herein are apparatuses configured to perform any of the methods described. For example, described herein are intraoral scanning systems for generating a model of a subject's teeth that include: a hand-held wand having at least one sensor and a plurality of light sources, wherein the light sources are configured to emit light at a first spectral range and a second spectral range, wherein the second spectral range is penetrative; and one or more processors operably connected to the hand-held wand, the one or more processors configured to: generate a three-dimensional (3D) surface model of at least a portion of a subject's tooth using light from a first spectral range; and generate a 3D model of the subject's tooth including internal structures based on the 3D surface model and on a plurality of images taken at the second spectral range showing internal structures.

An intraoral scanning system for generating a model of a subject's teeth may include: a hand-held wand having at least one sensor and a plurality of light sources, wherein the light sources are configured to emit light at a first spectral range and a second spectral range, further wherein the second spectral range is penetrative; and one or more processors operably connected to the hand-held wand, the one or more processors configured to: determine surface information by using light in the first spectral range sensed by the hand-held wand, using a first coordinate system; generate a three-dimensional (3D) surface model of at least a portion of a subject's tooth using the surface information; take a plurality of images in the second spectral range, wherein the images reference the first coordinate system; and generate a 3D model of the subject's tooth including internal structures based on the 3D surface model and the a plurality of images.

Also described herein are methods of generating a model of a subject's teeth that include both surface and internal structures in which the same intraoral scanner is cycled between different modalities such as between surface scanning and penetration; additional modalities (e.g., laser florescence, etc.) may also alternatively be included. In general, although the examples described herein focus on the combination of surface and penetration, other internal scanning techniques (e.g., laser florescence) may be used instead or in addition to the internal feature imaging described herein.

For example, described herein are methods of generating a model of a subject's teeth including both surface and internal structures including the steps of: using a hand-held intraoral scanner to scan a portion of a subject's tooth using a first modality to capture three-dimensional (3D) surface model data of the tooth; using the hand-held intraoral scanner to scan the portion of the subject's tooth using a second modality to image into the tooth using a penetrative wavelength to capture internal data of the tooth; cycling between the first modality and the second modality, wherein cycling rapidly switches between the first modality and the second modality so that images using the penetrative wavelength share a coordinate system with the 3D surface model data captured in the first modality.

Any of the methods described herein may include automatically adjusting the duration of time spent scanning in first modality, the duration of time spent in the second modality, or the duration of time spent in the first and the second modality when cycling between the first modality and the second modality. For example, any of these methods may include automatically adjusting a duration of time spent scanning in first modality, the duration of time spent in the second modality, or the duration of time spent in the first and the second modality when cycling between the first modality and the second modality based on the captured 3D surface model data, the internal data, or both the 3D surface model data and the internal data. Thus, a method of generating a model of a subject's teeth may include: using a hand-held intraoral scanner to scan a portion of a subject's tooth using a first modality to capture three-dimensional (3D) surface model data of the tooth; using the hand-held intraoral scanner to scan the portion of the subject's tooth using a second modality to image into the tooth using a penetrative wavelength to capture internal data of the tooth; cycling between the first modality and the second modality using a scanning scheme wherein cycling rapidly switches between the first modality and the second modality so that the internal data uses the same coordinate system as the 3D surface model data captured in the first modality; and adjusting the scanning scheme based on the captured 3D surface model data, the internal data, or both the 3D surface model data and the internal data.

The scanning scheme adjustment may comprise adjusting based on determination of the quality of the captured 3D surface model data. Adjusting the scanning scheme may comprise automatically adjusting the scanning scheme, and/or adjusting a duration of scanning in the first modality and/or adjusting a duration of scanning in the second modality.

Any of these methods may include combining the 3D surface model data and the internal data of the tooth to form a 3D model of the tooth.

As mentioned above, capturing the 3D surface model data may include determining a 3D surface topology using confocal focusing/confocal scanning, stereo vision or structured light triangulation.

In general, cycling may comprise cycling between the first modality, the second modality, and a third modality, wherein cycling rapidly switches between the first modality, the second modality and the third modality so that images using the penetrative wavelength share a coordinate system with the 3D surface model captured in the first modality. The third modality may be another penetrative modality or a non-penetrative modality (e.g., color, a visual image the subject's tooth, etc.).

Using the hand-held intraoral scanner to scan the portion of the subject's tooth using the second modality may include illuminating the tooth at an angle of between 0° and 15° relative to a direction of view of the sensor receiving the illumination (e.g., small angle illumination). The step of using the hand-held intraoral scanner to scan the portion of the subject's tooth using the second modality may include taking a plurality of penetration images at a plurality of different angles between an illumination source and a sensor and/or at a plurality of different positions or angles relative to the tooth so that the same internal region of the tooth is imaged from different angles relative to the tooth.

As mentioned, any appropriate penetrative wavelength may be used, including infrared (e.g., near infrared). For example using the hand-held intraoral scanner to scan the portion of the subject's tooth using the second modality may comprise illuminating with one or more of: white light trans-illumination, UV/Blue fluorescence, and red light fluorescence.

Also described herein are intraoral scanning systems for generating a model of a subject's teeth that are configured to cycle between scanning modes. For example, described herein are intraoral scanning systems comprising: a hand-held intraoral wand having at least one sensor and a plurality of light sources, wherein the light sources are configured to emit light at a first spectral range and at a second spectral range, further wherein the second spectral range is penetrative; and one or more processors operably connected to the hand-held intraoral wand, the one or more processors configured to cause the wand to cycle between a first mode and a second mode, wherein in the first mode the wand emits light at the first spectral range for a first duration and the one or more processors receives three dimensional (3D) surface data in response, and wherein in the second mode the wand emits light at the second spectral range for a second duration and the one or more processors receives image data in response.

An intraoral scanning system for generating a model of a subject's teeth may include: a hand-held intraoral wand having at least one sensor and a plurality of light sources, wherein the light sources are configured to emit light at a first spectral range and at a second spectral range, further wherein the second spectral range is penetrative; and one or more processors operably connected to the wand, the one or more processors configured to cause the wand to cycle between a first mode and a second mode, wherein in the first mode the wand emits light at the first spectral range for a first duration and the one or more processors receives three dimensional (3D) surface data in response, and wherein in the second mode the wand emits light at the second spectral range for a second duration and the one or more processors receives image data in response; wherein the one or more processors is configured to adjusting the first duration and the second duration based on the received 3D surface data, the received image data, or both the 3D surface data and the image data. In any of the apparatuses described herein, one mode may be the surface scanning (3D surface), which may be, for example, at 680 nm. Another mode may be a penetrative scan, using, e.g., near-IR light (e.g., 850 nm). Another mode may be color imaging, using white light (e.g., approximately 400 to 600 nm).

Penetration imaging methods for visualizing internal structures using a hand-held intraoral scanner are also described. Thus, any of the general methods and apparatuses described herein may be configured specifically for using penetration imaging data to model a tooth or teeth to detect internal features such as crack and caries. For example, a method of imaging through a tooth to detect cracks and caries may include: taking a plurality of penetration images through the tooth at different orientations using a hand-held intraoral scanner in a first position, wherein the intraoral scanner is emitting light at a penetrative wavelength; determining surface location information using the intraoral scanner at the first position; and generating a three-dimensional (3D) model of the tooth using the plurality of penetration images and the surface location information.

Generating a 3D model of the tooth may comprise repeating the steps of taking the plurality of penetration images and generating the 3D model for a plurality of different locations.

Taking the plurality of penetration images through the tooth at different orientations may include taking penetration images in which each penetration image is taken using either or both of: a different illumination source or combination of illumination sources on the intraoral scanner emitting the penetrative wavelength or a different image sensor on the intraoral scanner taking the image.

In some variations taking the plurality of penetration images may comprise taking three or more penetration images.

Taking the plurality of penetration images through the tooth surface at different orientations may comprises taking penetration images using small angle illumination/viewing, for example, wherein, for each penetration image, an angle between emitted light and light received by an image sensor is between 0 and 15 degrees. For example, a method of imaging through a tooth to detect cracks and caries may include: scanning a tooth from multiple positions, wherein scanning comprises repeating, for each position: taking a plurality of penetration images through the tooth at different orientations using an intraoral scanner, wherein the intraoral scanner is emitting light at a penetrative wavelength and wherein, for each penetration image, an angle between emitted light and light received by an image sensor is between 0 and 15 degrees, and determining surface location information using the intraoral scanner; and generating a three-dimensional (3D) model of the tooth using the penetration images and the surface location information.

As mentioned above, in addition to the apparatuses (e.g., scanning apparatuses, tooth modeling apparatuses, etc.) and methods of scanning, modeling and operating a scanning and/or modeling apparatus, also described herein are methods of reconstructing volumetric structures using images generated from one or more penetrative wavelengths.

For example, described herein are methods of reconstructing a volumetric structure from an object including semi-transparent strongly scattering regions (e.g., a tooth) for a range of radiation wavelengths. The method may include illuminating the object with a light source that is emitting (e.g., exclusively or primarily radiating) a penetrating wavelength, taking a plurality of images of the object with a camera sensitive to the penetrating wavelength (e.g., recording in the range of radiation wavelengths), receiving location data representing a location of the camera relative to the object for each of the plurality of images, generating for each point in a volume an upper bound on a scattering coefficient from the plurality of images and the location data, and generating an image of the object from the upper bound of scattering coefficients for each point. The penetrating wavelength of light applied to the object may be emitted from substantially the same direction as the camera. The image or images generated may illustrate features within the volume of the object, and the image may also include (or be modified to include) the outer boundary of the object, as well as the internal structure(s).

As used herein, a tooth may be described as an object including semi-transparent strongly scattering region or regions; in general, teeth may also include strong scattering regions (such as dentine), and lightly scattering, highly transparent regions (such as the enamel) at near-IR wavelengths. Teeth may also include regions having intermedia or mixed scattering properties, such as caries. The methods and apparatuses for performing volumetric scans described herein are well suited for mapping these different regions in the tooth/teeth.

A method of reconstructing a volumetric structure from an object including semi-transparent strongly scattering regions for a range of radiation wavelengths may include: taking a plurality of images of the object with a camera in the range of radiation wavelengths, wherein lighting for the plurality of images is projected substantially from a direction of the camera, receiving location data representing a location of the camera relative to the object for each of the plurality of images, generating for each point in a volume an upper bound on a scattering coefficient from the plurality of images and the location data, and generating an image of the object from the upper bound of scattering coefficients for each point.

The range of radiation wavelengths may be infrared or near infrared wavelength(s).

Any of these methods may also include receiving surface data representing an exterior surface of the object, wherein the generating step is performed for each point in the volume within the exterior surface of the object.

The object may comprise a tooth, having an exterior enamel surface and an interior dentin surface. Teeth are just one type of object including semi-transparent strongly scattering regions; other examples may include other both tissues (including soft and/or hard tissues), e.g., bone, etc. These objects including semi-transparent strongly scattering regions may include regions that are typically semi-transparent and strongly scattering for the penetrative wavelengths (e.g., the infrared or near infrared wavelengths), as described herein.

The location data may generally include position and orientation data of the camera at the time of capturing each of the plurality of images. For example, the location data may comprise three numerical coordinates in a three-dimensional space, and pitch, yaw, and roll of the camera.

Generating for each point in the volume the upper bound on scattering coefficients may comprise projecting each point of a 3D grid of points corresponding to the volume of the object onto each of the plurality images using a first calibration, producing a list of intensity values for each projected point, converting each intensity value on the list of intensity values to a scattering coefficient according to a volume response, and storing a minimum scattering coefficient value for each grid point from the list of scattering coefficient values.

For example, the first calibration may comprise a fixed pattern noise calibration to calibrate for sensor issues and image ghosts of the camera. The first calibration may comprise a camera calibration that determines a transformation for the camera that projects known points in space to points on an image.

Also described herein are methods of reconstructing a volumetric structure from a tooth, semi-transparent in a range of radiation wavelengths, the method comprising receiving, in a processor, a representation of a surface of the tooth in a first coordinate system, receiving, in the processor, a plurality of images of the tooth in the range of radiation wavelengths, the plurality of images taken with lighting projected substantially from a direction of a camera, receiving, in the processor, location data representing a location of the camera for each of the plurality of images, projecting each point of a grid of points corresponding to a volume within the surface of the tooth onto each of the plurality images using a first calibration, producing a list of intensity values for each projected point, converting each intensity value on the list of intensity values to a scattering coefficient according to a volume response, and storing a minimum scattering coefficient for each point into a list of minimum scattering coefficients.

Any of these methods may further comprise producing an image from the list of minimum scattering coefficients.

The location data may comprise position and orientation data of the camera (or cameras) at the time of capturing each of the plurality of images.

The first calibration may comprise a fixed pattern noise calibration to calibrate for sensor issues and image ghosts of the camera. In some embodiments, the first calibration may comprise a camera calibration that determines a transformation for the camera that projects known points in space to points on an image.

The method may further comprise receiving surface data representing an exterior surface of the object, wherein the projecting step is performed for each point inside the volume within the exterior surface of the object.

The grid of points may comprise a cubic grid.

Any of the methods described herein may be embodied as software, firmware and/or hardware. For example, any of these methods may be configured as non-transitory computing device readable medium having instructions stored thereon for performing the method.

For example, a non-transitory computing device readable medium having instructions stored thereon for reconstructing a volumetric structure from a tooth that is semi-transparent in a range of radiation wavelengths is described. The instructions may be executable by a processor to cause a computing device to receive a representation of a surface of the tooth in a first coordinate system, receive a plurality of images of the tooth in the range of radiation wavelengths, the plurality of images taken with lighting projected substantially from a direction of a camera, receive location data representing a location of the camera for each of the plurality of images, project each point of a grid of points corresponding to a volume of the tooth onto each of the plurality of images using a first calibration, produce a list of intensity values for each projected point, convert each intensity value on the list of intensity values to a scattering coefficient according to a volume response, and store a minimum scattering coefficient for each point into a list of minimum scattering coefficients, and produce an image from the list of minimum scattering coefficients.

The location data may comprise position and orientation data of the camera at the time of capturing each of the plurality of near-infrared images. The location data may comprise three numerical coordinates in a three-dimensional space, and pitch, yaw, and roll of the camera.

The first calibration may comprise a fixed pattern noise calibration to calibrate for sensor issues and image ghosts of the camera. The first calibration may comprise a camera calibration that determines a transformation for the camera that projects known points in space to points on an image.

The grid of points may be inside the tooth; as mentioned, the grid of points may comprise a cubic grid.

Alternatively or additionally to the use of scattering coefficients, any appropriate method of forming the internal structures of the patient's teeth using the penetrative wavelength images. For example, any of the apparatuses (e.g., systems, devices, software, etc.) and methods described herein may use the two-dimensional penetrative images along with position and/or orientation information about the scanner relative to the object being imaged (e.g., the teeth) to segment the 2D penetrative images to form a three-dimensional model of the teeth including an internal structure from within the teeth. As described, a penetrative image may refer to an images taken with a near-IR and/or IR wavelength), penetrating into the object. The position and/or orientation of the scanner may be a proxy for the position and/or orientation of the camera taking the images which is one the scanner (e.g., on a handheld wand).

For example, described herein are methods of modeling a subject's teeth, comprising: capturing, with an intraoral scanner, a plurality of images of an interior of the subject's teeth and a position and orientation of the intraoral scanner specific to each image of the plurality of images; segmenting the plurality of images to form an internal structure corresponding to a structure within the subject's teeth; using the position and orientation of the plurality of images to project the internal structure onto a three-dimensional model of the subject's teeth; and displaying the three-dimensional model of the subject's teeth including the internal structure.

In any of these methods and apparatuses, the 3D surface model may be concurrently captured using a non-penetrative wavelength (e.g., surface scan) while capturing the penetrative images. For example, capturing may comprise capturing surface images of the subject's teeth while capturing the plurality of images of the interior of the subject's teeth. The method may also include forming the three dimensional model of the subject's teeth from the captured surface images. For example, forming the three dimensional model of the subject's teeth may comprise determining a three-dimensional surface topology using confocal focusing. Capturing the surface images of the subject's teeth may comprise using confocal scanning, stereo vision or structured light triangulation.

In general, the same device (e.g., scanner) may model and/or display the 3D representation of the teeth, including the internal structures, alternatively or additionally a separate processor (e.g., remote to the scanner) may be used. Any of these methods may also include storing and/or transmitting plurality of penetrative images and the position and orientation of the intraoral scanner while capturing the plurality of two-dimensional images, including transmitting to a remote processor for performing the segmentation and later steps.

In any of the methods and apparatuses described herein, the 3D model including the internal structure(s) may be displayed while the scanner is operating. This may advantageously allow the user to see, in real-time or near real-time the internal structure(s) in the subject's teeth. Thus, any of these methods may include displaying the three-dimensional model as the images are captured.

Segmenting the plurality of images may comprise applying edge detection to the plurality of images to identify closed boundaries within the plurality of images. Segmenting the plurality of images may comprise forming a volumetric density map from the plurality of images to identify the internal structure. Segmenting the volumetric density map may include segmenting by identifying one or more iso-surfaces within the volumetric density map to identify the internal features. Any of these methods may include segmenting the volumetric density map to identify the internal feature (e.g., cracks, caries, dental fillings, dentin, etc.).

For example, an intraoral scanning apparatus configured to generate a model of a subject's teeth may include: an intraoral scanner having a plurality of light sources and a position and orientation sensor, wherein the light sources are configured to emit light at a first spectral range and at a second spectral range, further wherein the second spectral range is penetrative; and a processor operably connected to the intraoral scanner, the one or more processors configured to cause the scanner to capture a plurality of images and position and orientation of the intraoral scanner corresponding to each of the plurality of images when the intraoral scanner is emitting light at the second spectral range; wherein the processor is further configured to segment the plurality of images to form an internal structures corresponding to a structure within the subject's teeth, and to display or transmit a three-dimensional model of the subject's teeth including the internal structure.

The processors may be configured to segment the plurality of images by applying edge detection to the plurality of images to identify closed boundaries within the plurality of images. The processor may be configured to segment the plurality of images by forming a pixel density map from the plurality of images to identify the internal structure. The processor may be configured to identify closed segments within the pixel density map to identify the internal structure.

Also described herein are non-transitory computing device readable medium having instructions stored thereon that are executable by a processor to cause an intraoral scanning apparatus to: capture a plurality of images using a penetrative wavelength of light and a position and orientation of the intraoral scanner specific to each image of the plurality of images; segment the plurality of images to form an internal structure corresponding to a structure within a subject's teeth; use the position and orientation of the intraoral scanner specific to each image to project the internal structure onto a three-dimensional model of the subject's teeth; and display the three-dimensional model of the subject's teeth including the internal structure.

The non-transitory computing device readable medium having instructions may be further configured to cause the intraoral scanning apparatus to segment the plurality of images by applying edge detection to the plurality of images to identify closed boundaries within the plurality of images. The non-transitory computing device readable medium having instructions may be further configured to cause the intraoral scanning apparatus to segment the plurality of images by forming a pixel density map from the plurality of images to form the internal structure. The non-transitory computing device readable medium having instructions may be further configured to cause the intraoral scanning apparatus to segment the plurality of images by identifying closed segments within the pixel density map to form the internal structure.

Also described herein are non-transitory computing device readable medium having instructions stored thereon that are executable by a processor to cause a computing device to: receive, from a scanner, three-dimensional surface model data of a subject's teeth; receive, from the scanner, a plurality of images of an interior of the subject's teeth and position and orientation of the intraoral scanner specific to each image of the plurality of images; segment the plurality of images to form an internal structure of the subject's teeth; project the internal structure of the subject's teeth onto the three-dimensional surface model; and display the three-dimensional surface model showing the internal structure.

For example, described herein are methods for generating a three-dimensional (3D) volumetric model of a subject's teeth using an intraoral scanner, the method comprising: capturing 3D surface model data of at least a portion of the subject's teeth using an intraoral scanner as the intraoral scanner is moved over the teeth; taking a plurality of images into the teeth using a near-infrared (near-IR) wavelength with the intraoral scanner as the intraoral scanner is moved over the teeth so that multiple images of a same internal region of the teeth are imaged; determining, for each of the plurality of images into the teeth, a position of the intraoral scanner relative to the subject's teeth using the 3D surface model data; and forming the 3D volumetric model of the subject's teeth including internal features using the plurality of images and the position of the intraoral scanner relative to the subject's teeth.

A method for generating a three-dimensional (3D) volumetric model of a subject's teeth using an intraoral scanner may include: capturing 3D surface model data of at least a portion of the subject's teeth using an intraoral scanner as the intraoral scanner is moved over the teeth; taking a plurality of images into the teeth using a near-infrared (near-IR) wavelength as the intraoral scanner is moved over the teeth by emitting a near-IR light from the intraoral scanner in a first polarization, and detecting, in an image sensor in the intraoral scanner, the near-IR light returning to the intraoral scanner, wherein the near-IR light returning to the intraoral scanner is filtered to remove specular reflection by filtering near-IR light in the first polarization from the near-IR light returning to the intraoral scanner before it reaches the image sensor; determining, for each of the plurality of images into the teeth, a position of the intraoral scanner relative to the subject's teeth when each of the plurality of images is captured, using the 3D surface model data; and forming the 3D volumetric model of the subject's teeth including internal features using the plurality of images and the position of the intraoral scanner relative to the subject's teeth.

In any of these methods and apparatuses, the near-IR light returning to the intraoral scanner may be filtered to remove specular reflection by filtering all or nearly all of the near-IR light in the first polarization from the near-IR light returning to the intraoral scanner before it reaches the image sensor.

Also described herein are intraoral scanners scan both surface and internal structures. For example, an intraoral scanning system for generating a three-dimensional (3D) volumetric model of a subject's teeth may include: a hand-held wand having at least one image sensor and a plurality of light sources, wherein the light sources are configured to emit light at a first spectral range and a second spectral range, wherein the second spectral range is within near-infrared (near-IR) range of wavelengths; and one or more processors operably connected to the hand-held wand, the one or more processors configured to: capture 3D surface model data of at least a portion of the subject's teeth as the intraoral scanner is moved over the teeth; take a plurality of images into the teeth using light in the second spectral range as the intraoral scanner is moved over the teeth so that multiple images of a same internal region of the teeth are imaged; determine, for each of the plurality of images into the teeth, a position of the hand-held wand relative to the subject's teeth using the 3D surface model data; and form the 3D volumetric model of the subject's teeth including internal features using the plurality of images and the position of the intraoral scanner relative to the subject's teeth.

An intraoral scanning system for generating a three-dimensional (3D) volumetric model of a subject's teeth may include: a hand-held wand having at least one image sensor and a plurality of light sources, wherein the light sources are configured to emit light at a first spectral range and a second spectral range, wherein the second spectral range is within near-infrared (near-IR) range of wavelengths; a filter in front of the image sensor configured to filter light in the second spectral range and the first polarization; and one or more processors operably connected to the hand-held wand, the one or more processors configured to: capture 3D surface model data of at least a portion of the subject's teeth as the intraoral scanner is moved over the teeth; take a plurality of images into the teeth using light in the second spectral as the intraoral scanner is moved over the teeth by emitting a near-IR light from the intraoral scanner in a first polarization, and detecting, in an image sensor in the intraoral scanner, the near-IR light returning to the intraoral scanner, wherein the near-IR light returning to the intraoral scanner is filtered to remove specular reflection by filtering near-IR light in the first polarization from the near-IR light returning to the intraoral scanner before it reaches the image sensor; determine, for each of the plurality of images into the teeth, a position of the hand-held wand relative to the subject's teeth using the 3D surface model data; and form the 3D volumetric model of the subject's teeth including internal features using the plurality of images and the position of the intraoral scanner relative to the subject's teeth.

Also described herein are methods of imaging cracks and caries in teeth. For example, described herein are methods of imaging into a subject's teeth to detect cracks and caries using an intraoral scanner, the method comprising: scanning the intraoral scanner over the subject's teeth; taking a plurality of near-infrared (near-IR) images into the subject's teeth at different orientations using the intraoral scanner emitting both a near-IR wavelength and a non-penetrative wavelength; determining a position of the intraoral scanner relative to the subject's teeth for each location of an image from the plurality of near-IR images using the non-penetrative wavelength; and generating a three-dimensional (3D) volumetric model of the subject's teeth using the plurality of near-IR images and the position of the intraoral scanner relative to the subject's teeth for each near-IR image of the plurality of near-IR images.

Any of these methods may include analyzing the volumetric model to identify a crack or caries (or other internal regions of the teeth).

For example, a method of imaging through a subject's teeth to detect cracks and caries may include: scanning the subject's teeth from multiple positions, wherein scanning comprises repeating, for each position: taking a plurality of near-infrared (near-IR) images into the teeth at different orientations using an intraoral scanner, wherein the intraoral scanner is emitting light at a near-IR wavelength in a first polarization and wherein, for each near-IR image, an angle between emitted light and light received by an image sensor is between 0 and 15 degrees, further wherein received near-IR light is filtered to block near-IR light in the first polarization, and determining a position of the intraoral scanner relative to the subject's teeth for each location of an image from the plurality of near-IR images using; and generating a three-dimensional (3D) volumetric model of the tooth using the penetration images and the surface location information.

Also described herein are methods of using scattering coefficients to generate internal images of tooth based on penetrating images and camera sensor location. For example, a method of forming a three-dimensional (3D) volumetric model of a subject's teeth may include: taking a plurality of near-infrared (near-IR) images of the subject's teeth with a camera sensor, wherein the near-IR lighting for the plurality of near-IR images is projected substantially from a direction of the camera sensor; receiving location data representing a location of the camera relative to the subject's teeth for each of the plurality of near-IR images; generating, for each point in a volume, an upper bound on a scattering coefficient from the plurality of near-IR images and the location data; combining the upper bound of scattering coefficients for each point in a volume to form a 3D volumetric model of the subject's teeth; and outputting the 3D volumetric model of the subject's teeth.

Any of these methods may include forming an iso-surface from the 3D volumetric model of the subject's teeth. The iso-surface may be formed by selecting a threshold or range of values of the scattering coefficients. Sub-ranges may correspond to different internal regions (e.g., structures). For example, outputting may comprise forming an iso-surface corresponding to an interior dentin surface from the 3D volumetric model of the subject's teeth.

A method of reconstructing a volumetric structure from a tooth, wherein the tooth is semi-transparent in a range of radiation wavelengths, may include: receiving, in a processor, a representation of a surface of the tooth in a first coordinate system; receiving, in the processor, a plurality of images of the tooth taken by a camera in the range of radiation wavelengths, the plurality of images taken with lighting projected substantially from a direction of the camera; receiving, in the processor, location data representing a location of the camera for each of the plurality of images; projecting each point of a grid of points corresponding to a volume within the surface of the tooth onto each of the plurality images using a first calibration; producing a list of intensity values for each projected point; converting each intensity value on the list of intensity values to a scattering coefficient according to a volume response; and storing a minimum scattering coefficient for each point into a list of minimum scattering coefficients.

Any of these methods may be embodied in an apparatus, including software, hardware and/or firmware for performing the method. For example, described herein are non-transitory computing device readable medium having instructions stored thereon for reconstructing a volumetric structure from a tooth that is semi-transparent in a range of radiation wavelengths, wherein the instructions are executable by a processor to cause a computing device to: receive a representation of a surface of the tooth in a first coordinate system; receive a plurality of images of the tooth taken by a camera in the range of radiation wavelengths, the plurality of images taken with lighting projected substantially from a direction of the camera; receive location data representing a location of the camera for each of the plurality of images; project each point of a grid of points corresponding to a volume of the tooth onto each of the plurality of images using a first calibration; produce a list of intensity values for each projected point; convert each intensity value on the list of intensity values to a scattering coefficient according to a volume response; and store a minimum scattering coefficient for each point from the scattering coefficients; and output an image produced from the list of minimum scattering coefficients.

Also described herein are methods of forming the internal structures using segmentation. For example, a method of modeling a subject's teeth, may include: capturing, with an intraoral scanner, a plurality of images of an interior of the subject's teeth and a position and orientation of the intraoral scanner specific to each image of the plurality of images; segmenting the plurality of images to form an internal structure corresponding to a structure within the subject's teeth; using the position and orientation of the plurality of images to project the internal structure onto a three-dimensional model of the subject's teeth; and displaying the three-dimensional model of the subject's teeth including the internal structure.

Also described herein are intraoral scanning apparatus configured to generate a model of a subject's teeth, the apparatus comprising: an intraoral scanner having a plurality of light sources and a position and orientation sensor, wherein the light sources are configured to emit light at a first spectral range and at a second spectral range, further wherein the second spectral range is penetrative; and a processor operably connected to the intraoral scanner, the one or more processors configured to cause the scanner to capture a plurality of images and position and orientation of the intraoral scanner corresponding to each of the plurality of images when the intraoral scanner is emitting light at the second spectral range; wherein the processor is further configured to segment the plurality of images to form an internal structures corresponding to a structure within the subject's teeth, and to display or transmit a three-dimensional model of the subject's teeth including the internal structure.

Also described herein are non-transitory computing device readable medium having instructions stored thereon that are executable by a processor to cause an intraoral scanning apparatus to: capture a plurality of images using a penetrative wavelength of light and a position and orientation of the intraoral scanner specific to each image of the plurality of images; segment the plurality of images to form an internal structure corresponding to a structure within a subject's teeth; use the position and orientation of the intraoral scanner specific to each image to project the internal structure onto a three-dimensional model of the subject's teeth; and display the three-dimensional model of the subject's teeth including the internal structure.

Also described herein are methods for forming 3D volumes (including volumetric volumes) of teeth. For example, described herein are methods comprising: receiving data associated with an intraoral scan of a subject; determining, from the received data, at least a portion of a volume of a first internal feature of a tooth of the subject; determining, from the received data, at least a portion of a volume of a second internal feature of the tooth of the subject, the first internal feature differing from the second internal feature; mapping the portion of the volume of the first internal feature with the portion of the volume of the second internal feature; outputting a 3D volume of the portion of the volume of the first internal feature with the portion of the volume of the second internal feature.

The received data may comprise data from tooth surface penetrating intraoral scan of the subject. The received data may further comprise data from a tooth surface intraoral scan of the subject.

The method may also include determining, from the received data, a surface of the tooth of the subject; mapping the surface of the tooth with the portion of the volume of the first internal feature and the portion of the volume of the second internal feature; and outputting the 3D volume with the surface of the tooth with the portion of the volume of the first internal feature and the portion of the volume of the second internal feature.

The received data may further comprise data from a tooth surface color intraoral scan of the subject.

The method may also comprise, determining, from the received data, a color of the surface of the tooth of the subject; mapping the color of the surface of the tooth to the surface of the tooth; and outputting the 3D volume with the surface of the tooth and the color of the surface of the tooth.

The first internal feature of the tooth may comprise a dentin of the tooth and the second internal feature of the tooth comprises an enamel of the tooth. The intraoral scan may comprise a second intraoral scan of the subject; and wherein the method further comprises receiving data associated with a prior intraoral scan of the subject; determining from the received data associated with the prior intraoral scan of the subject, at least a portion of a volume of the enamel or the dentin; and determining a volume change of the enamel or the dentin by comparing the portion of the volume of the enamel or the dentin determined from the received data associated with the second intraoral scan and the portion of the volume of the enamel or the dentin determined from the received data associated with the prior intraoral scan; and outputting the determined volume change.

The method may also include detecting a dental caries of the tooth by comparing the second internal feature and the first internal feature and outputting a signal to the user associated with the detected dental caries. Comparing the second internal feature and the second internal feature may comprise analyzing whether the volume of the second internal feature extends from a surface of the volume of the first internal feature. Analyzing may comprise determining whether the volume of the second internal feature extends from the surface of the volume of the first internal feature and to a portion of the second internal feature associated with the dentin.

The method may also include calculating a volume of the second internal feature that extends from the surface of the volume of the first internal feature and outputting a signal associated with the calculated volume.

Also described are method comprising: receiving data associated with an intraoral scan of a subject; determining, from the received data, a volume of a dental caries of a tooth of the subject; quantifying the volume of the dental caries of the tooth of the subject; and outputting a signal associated with the quantified volume of the dental caries of the tooth of the subject.

The method may also include determining, from the received data, a volume of an enamel of the tooth of the subject; mapping the volume of the enamel to the volume of the dental caries; and outputting a 3D volume of the mapped volumes of the enamel and the dental caries to a user. For example, determining, from the received data, a volume of a dentin of the tooth of the subject; mapping the volume of the dentin to the volume of the enamel and the volume of the dental caries; and outputting the 3D volume of the mapped volumes of the enamel and the dental caries with the volume of the dentin.

The intraoral scan of the subject may comprise a second intraoral scan of the subject and wherein the method further comprises receiving data associated with a prior intraoral scan of the subject; determining, from the received data associated with the prior intraoral scan of the subject, a prior volume of the dental caries of the tooth of the subject; outputting a signal associated with a difference in volume between the volume of the dental caries and the prior volume of the dental caries. The method may also comprise outputting a 3D model of the volume of the dental caries of the tooth of the subject.

Also described herein are trans-illumination adapter sleeve device for an intraoral scanner, the device comprising: a sleeve body configured to fit over a wand of an intraoral scanner, the sleeve body comprising a light-passing region at a distal end of the sleeve body configured to allow near-infrared (near-IR) light to pass through the sleeve; a first wing region extending from the distal end of the sleeve body adjacent to the light-passing region; and a near-IR light source configured to emit near-IR light from the first wing region. The near-IR light source may be configured to emit near-IR light transverse to the light-passing region.

The device may also include a second wing region extending from the distal end of the sleeve body adjacent to the light-passing region having a second near-IR light source configured to emit near-IR light from the second wing region. The device may also include an electrical contact on a proximal end of the sleeve body configured to apply electrical energy to the near-IR light source. The device may also include a flexible circuit coupling the electrical contact to the near-IR light source. Any of these devices may include a camera sensor operably connected to a second wing extending from the distal end of the sleeve body adjacent to the light-passing region.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 3A, 3B and 3C illustrate exemplary penetration with small angle illumination imaging orientations using an intraoral scanner wand such as the one shown in FIGS. 2C and 2D.

FIG. 3D shows another example (similar to what is shown in FIG. 3A) of illuminating with light (e.g., near-IR) on the right side and imaging from the left side (this orientation may be flipped) to get 180° trans-illumination. Higher and lower scattering is shown by the arrows.

FIG. 4A illustrates an example of a penetration imaging (e.g., small-angle penetration imaging) configuration of sensors and light (illumination) sources in which the viewing vector between the sensors and light sources is between 0° and 15° at different positions around a tooth; these different positions represent different positions taken at different times, e.g., by moving the wand/scanner around the tooth so that penetrative images may be taken at different angles relative to the tooth.

FIGS. 4B-4F illustrate other variations of penetrative imaging similar to that shown in FIG. 4A, for imaging from a tooth. FIG. 4B shows an example of a multi-camera, multi-light source scanner. FIGS. 4C-4F show alternative small-angle configurations.

FIGS. 5A-5I illustrate nine alternative penetration imaging orientations that may be used as part of an intraoral scanner such as the ones shown in FIGS. 1A-1B. In FIGS. 5A-5C the central sensor is active, and either the right (FIG. 5B) or the left (FIG. 5A) or both (FIG. 5C) light sources are illuminating the tooth. Similarly, in FIGS. 5D-5E the right sensor is active, while in FIGS. 5G-5I the left sensor is active.

In FIG. 8, the y-axis indicates the lens position of the 3D confocal scanner (scan amplitude). The durations of each of the scans (e.g., the scanning time for each mode) may be fixed, it it may be adjustable. For example the duration of the penetrative scan (d) may be dynamically adjusted (e.g., increased or decreased) during scanning base on the quality of the images received, the completeness of the 3D reconstruction of internal structures, etc. Similarly, the duration of the surface scan may be dynamically adjusted during scanning based on the quality of the image(s) being scanned (e.g., the prior images and/or the current image, etc.), the completeness of the 3D surface model for the region being scanned, etc.

FIGS. 11A-11C shows projected images looking down through the top of the tooth using a penetrative wavelength (e.g., near-IR).

FIGS. 11D-11F illustrate the movement of the light source relative to the tooth in the z direction, using a penetrative wavelength.

FIGS. 11G-11I show the position of the scanner, such as those illustrated above, scanning the tooth in the z-direction. Note that FIGS. 11A, 11D and 11G correspond to a first depth position, FIGS. 11B, 11E and 11H correspond to a second (higher up the tooth) depth position, and FIGS. 11C, 11F and 11I correspond to a third (even higher up) depth.

FIG. 12 illustrates an example of a configuration of penetration light sources (e.g., penetrative spectral range light) and cameras that may be used as part of an intraoral scanner wand.

FIG. 13 shows a flowchart that describes one method for reconstructing a volumetric structure from an object including semi-transparent strongly scattering regions for a range of radiation wavelengths.

FIGS. 18A-18C illustrate one method of automatic segmentation of a near-IR image. FIG. 18A illustrates edge detection from a penetrative scan through the teeth, taken with an intraoral scanner in the near-IR wavelength (e.g., 850 nm). FIGS. 18B and 18C shows segmentation based on the edge detection of FIG. 18A plotted on the penetrative scan.

FIGS. 19A-19C show further segmentation of the near-IR image of FIGS. 18A-18C. FIG. 19A shows edge detection from the near-IR image taken of a subject's teeth shown in FIG. 19C. FIG. 19B shows segmentation of the image of FIG. 19C, in which the segments (5 segments) are drawn on the near-IR image shown in FIG. 19C.

FIGS. 20A-20C illustrate segmentation of a near-IR image of a patient's teeth. FIG. 20A is a figure showing edge detection of a near-IR image. FIG. 20B illustrates segmentation of the near-IR image, showing 18 (overlapping) segments. FIG. 20C illustrates further segmentation of the near-IR image shown in FIG. 20B.

FIGS. 21A-21C illustrate segmentation of a near-IR image of a patient's teeth. FIG. 21A shows edge detection of the near-IR image of FIG. 21C. FIG. 21B illustrates edge detection of the near-IR image shown in FIG. 21C.

FIG. 22A is a figure showing edge detection of a near-IR image. FIG. 22B illustrates segmentation of the near-IR image, showing 8 (overlapping) segments. FIG. 22C illustrates further segmentation of the near-IR image shown in FIG. 22B.

FIG. 23A shows edge detection of the near-IR image of FIG. 23C. FIG. 23B illustrates edge detection of the near-IR image shown in FIG. 23C.

FIG. 29A shows a partially transparent perspective view of a removable/disposable cover configured as a trans-illumination sleeve with electrical couplings. FIG. 29B is a perspective view of the sleeve of FIG. 29A, shown solid. This sleeve is configured for use with a wand portion of an intraoral scanner; the sleeve is configured to adapt the wand to include trans-illumination with a penetrative (e.g., near-IR) wavelength.

FIGS. 30A-30C illustrate one example of a trans-illumination sleeve with electrical couplings. FIG. 30A shows an example of a supporting frame of the sleeve; FIG. 30B shows the support frame with a flex circuit and connectors coupled to the supporting frame. FIG. 30C shows the fully assembled sleeve of FIGS. 30A-30B.

DETAILED DESCRIPTION

Figures 1A, 1B:
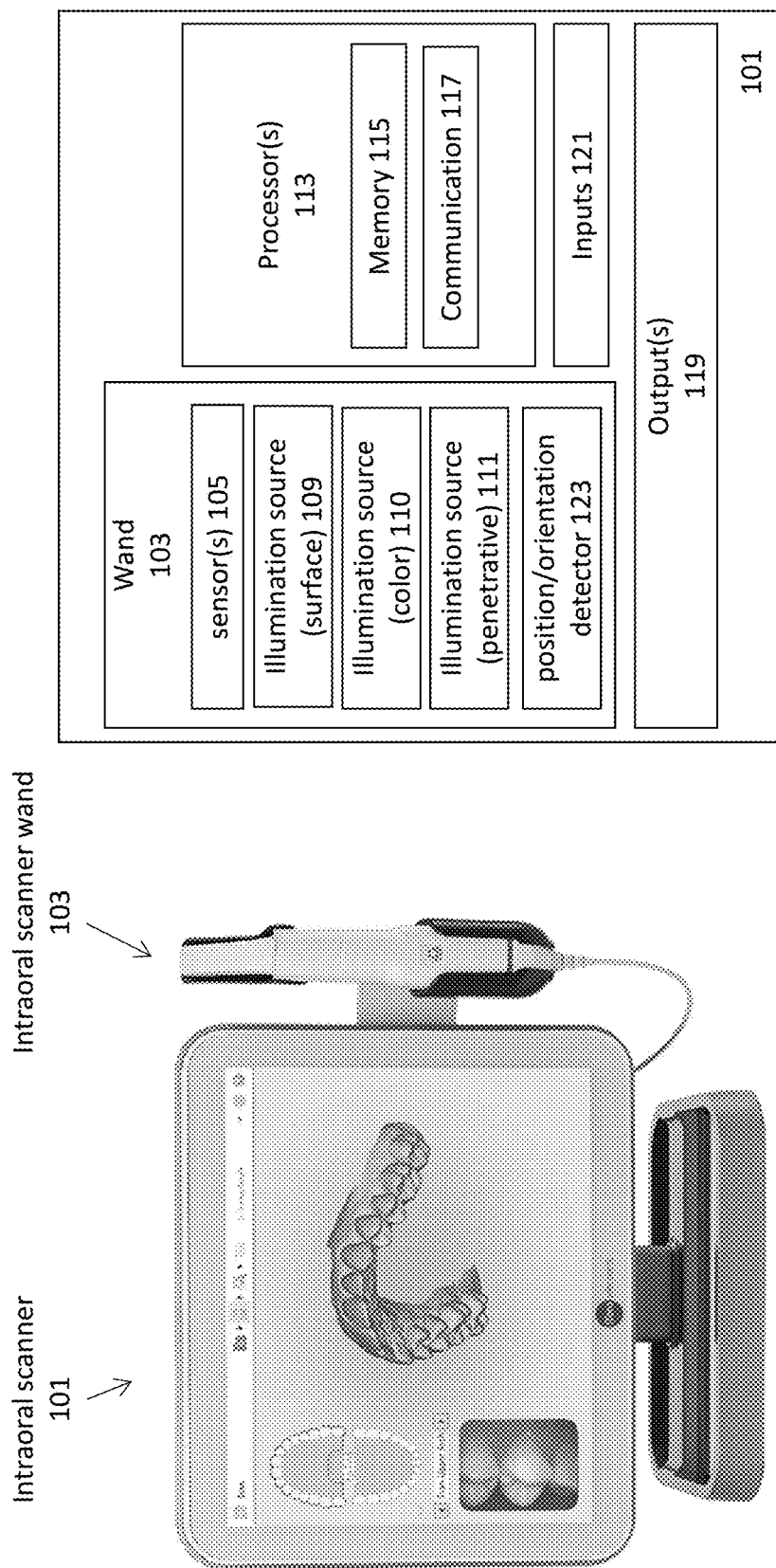
FIG. 1A illustrates one example of a 3D (color) intraoral scanner that may be adapted for used as described herein to generate a model of subject's teeth having both surface and internal features.
FIG. 1B schematically illustrates an example of an intraoral scanner configured to generate a model of subject's teeth having both surface and internal features.

Described herein are intraoral scanners for generating a three-dimensional (3D) model of a subject's intraoral region (e.g., tooth or teeth, gums, jaw, etc.) which may include internal features of the teeth and may also include a model of the surface, and methods of using such scanners. For example, FIG. 1A illustrates one example of an intraoral scanner 101 that may be configured or adapted as described herein to generate 3D models having both surface and internal features. As shown schematically in FIG. 1B, an exemplary intraoral scanner may include a wand 103 that can be hand-held by an operator (e.g., dentist, dental hygienist, technician, etc.) and moved over a subject's tooth or teeth to scan both surface and internal structures. The wand may include one or more sensors 105 (e.g., cameras such as CMOS, CCDs, detectors, etc.) and one or more light sources 109, 110, 111. In FIG. 1B, three light sources are shown: a first light source 109 configured to emit light in a first spectral range for detection of surface features (e.g., visible light, monochromatic visible light, etc.; this light does not have to be visible light), a second color light source (e.g., white light between 400-700 nm, e.g., approximately 400-600 nm), and a third light source 111 configured to emit light in a second spectral range for detection of internal features within the tooth (e.g., by trans-illumination, small-angle penetration imaging, laser florescence, etc., which may generically be referred to as penetration imaging, e.g., in the near-IR). Although separate illumination sources are shown in FIG. 1B, in some variations a selectable light source may be used. The light source may be any appropriate light source, including LED, fiber optic, etc. The wand 103 may include one or more controls (buttons, switching, dials, touchscreens, etc.) to aid in control (e.g., turning the wand on/of, etc.); alternatively or additionally, one or more controls, not shown, may be present on other parts of the intraoral scanner, such as a foot petal, keyboard, console, touchscreen, etc.

In general, any appropriate light source may be used, in particular, light sources matched to the mode being detected. For example, any of these apparatuses may include a visible light source or other (including non-visible) light source for surface detection (e.g., at or around 680 nm, or other appropriate wavelengths). A color light source, typically a visible light source (e.g., "white light" source of light) for color imaging may also be included. In addition a penetrating light source for penetration imaging (e.g., infrared, such as specifically near infrared light source) may be included as well.

The intraoral scanner 101 may also include one or more processors, including linked processors or remote processors, for both controlling the wand 103 operation, including coordinating the scanning and in reviewing and processing the scanning and generation of the 3D model including surface and internal features. As shown in FIG. 1B the one or more processors 113 may include or may be coupled with a memory 115 for storing scanned data (surface data, internal feature data, etc.). Communications circuitry 117, including wireless or wired communications circuitry may also be included for communicating with components of the system (including the wand) or external components, including external processors. For example the system may be configured to send and receive scans or 3D models. One or more additional outputs 119 may also be included for outputting or presenting information, including display screens, printers, etc. As mentioned, inputs 121 (buttons, touchscreens, etc.) may be included and the apparatus may allow or request user input for controlling scanning and other operations.

Any of the apparatuses and methods described herein may be used to scan for and/or identify internal structures such as cracks, caries (decay) and lesions in the enamel and/or dentin. Thus, any of the apparatuses described herein may be configured to perform scans that may be used to detect internal structures using a penetrative wavelength or spectral range of penetrative wavelengths. Also described herein are methods for detecting cracks, caries and/or lesions or other internal feature such as dental fillings, etc. A variety of penetrative scanning techniques (penetration imaging) may be used or incorporated into the apparatus, including but not limited to trans-illumination and small-angle penetration imaging, both of which detect the passage of penetrative wavelengths of light from or through the tissue (e.g., from or through a tooth or teeth).

Figure 2A:
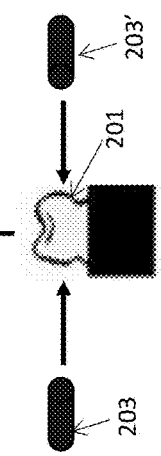
FIG. 2A illustrates trans-illumination imaging through a tooth at 180°.
Figure 2B:
FIG. 2B illustrates trans-illumination imaging through a tooth at 90°.

Trans-illumination is one technique that may be used for seeing internal features of teeth. Traditionally, there are 2 basic configurations for trans-illumination through the teeth. FIGS. 2A and 2B illustrate these: a 180° configuration and a 90° configuration. Both configurations may be used for visualizing inside the teeth, and mainly through the enamel. As shown in FIG. 2A, in the 180° configuration, a penetrative wavelength (including a spectral range of one or more penetrative wavelengths) is emitted from a light source 203 and passed from one side of the tooth 201, and a sensor 205 (e.g., camera) on the opposite side detects the light that has passed through the tooth without being scattered or absorbed. Similarly, in FIG. 2B, the tooth 201 is illuminated by light from light sources (203, 203') on either side of the tooth 201, and the camera 205, which is oriented 90° relative to both light sources, detect light at the right angle to the light source. Typically, trans-illumination has been limited to the use of a single projection type, in order to give an image capture inside the tooth (similar to the use of an x-ray). Described herein are methods and apparatuses for visualization of the enamel-dentin area using a penetrative wavelength (such as between 700 to 1300 nm, 700 to 1090 nm, etc., e.g., 850 nm) and acquiring a plurality of projections or orientations from a single position of the scanner relative to the tooth/teeth and/or for a plurality of angles of the sensor relative to the teeth; in particular three or more orientations or projections may be taken for each internal region being imaged. Taking multiple (e.g., 3 or more) projections may provide better imaging, as it may produce multiple (e.g., 3 or more) images through the tooth from a particular location of the wand relative to the tooth/teeth. The use of one or more 180° projection may be useful as the light travels a shorter distance and is less scattered, however the combination of multiple different projections (orientations) from the same location (e.g., at approximately the same scanning time, within a few milliseconds of each other) may permit the system to build a volumetric model of the enamel-dentin area.

Figure 2C:
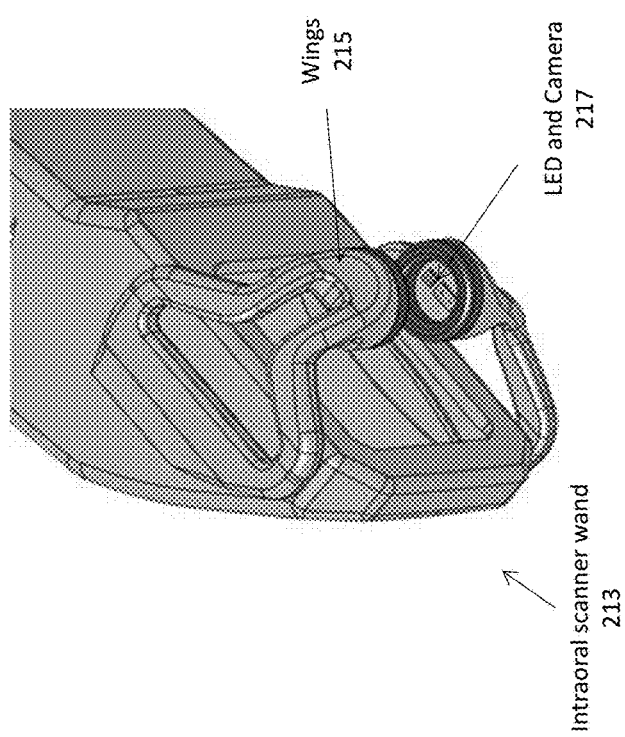
FIGS. 2C and 2D show side and top perspective views, respectively, of an example of a distal end of a wand of an intraoral scanner configured to provide trans-illumination imaging through a tooth at 90° and 180°.
Figure 2D:
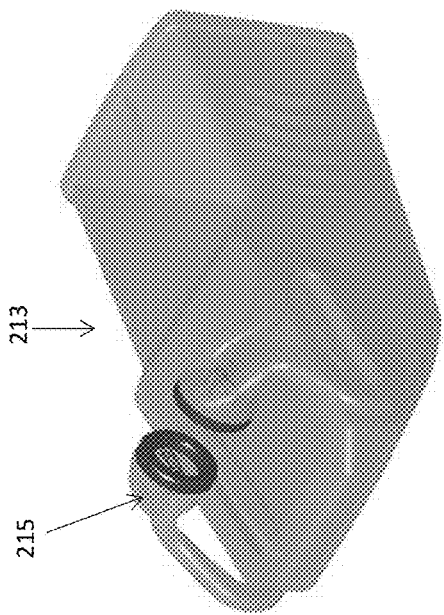

In variations using 90 and/or 180° configuration projections, the intraoral scanner may be adapted to provide trans-illumination imaging in this configuration. For example, FIGS. 2C and 2D illustrate one example of a distal end of a wand of an intraoral scanner adapted to collect trans-illumination images at 90 and 180°, in which the wand 213 includes a pair of projections or wings 215 each housing a light source (LED) and camera combination 217. In FIGS. 2C and 2D, both wings and the base of the wand may include light sources and sensors (cameras) so that at least three trans-illumination images may be taken from a single position of the wand relative to the teeth, as shown in FIGS. 3A-3C. In FIG. 3A a first orientation is shown, in which the right LED 303 is on, illuminating through the tooth for detection/capture (180°) by the camera 305 on the left. FIG. 3D is similar to FIG. 3A, showing light applied from the right side passing into the tooth (arrows) and either passing through to the camera sensor 305 (also referred to herein as an image sensor, camera, or just "sensor"), or scattered from an internal region. The orientation of the camera sensor and illumination source may be switched. In FIG. 3B the left LED 303' is on, illuminating through the tooth for detection/capture (180°) by the camera 305' on the right. In FIG. 3C, both of the LEDs 303, 303' are on, illuminating from both right and left sides, and a camera 305" located 90° off of the axis of the LEDs captures the trans-illumination image.

In general, the trans-illumination imaging data such as that described above can be combined with, and collected concurrently with, 3D surface data (e.g., 3D surface model data) of the teeth, allowing an additional layer of data on internal structures such as caries and cracks. Further, the use of multiple projections (taken from multiple orientations) as described may enable reconstruction of volumetric models internal structures of the teeth enamel, showing features that would not otherwise be visible.

Although the 90° and 180° configurations of trans-illumination of the teeth may be useful, it may be particularly beneficial to provide penetration imaging configurations in which the angle between the emitted and received rays (vectors) is much smaller, e.g., between 0° and 30°, between 0° and 25°, between 0° and 20°, between 0° and 15°, between 0° and 10°, etc. In particular, angles between 0° and 15° (or between >0° and 15°) may be useful.

Trans-illumination in the 180° configuration and 90° configuration may constrain the movement of the intraoral scanner wand around the teeth due to their camera to light source angle constraint (as shown in FIGS. 2C and 2D). Thus, also described herein are methods and apparatuses for penetration imaging/visualization, e.g., of the enamel-dentin area, using a small angle, including between 0° and 15°. In one example, a light source (LED) emitting a penetrative spectral range (e.g., 850 nm) is used having a viewing vector at a small angle of 0°-15° relative to the camera view angle. As mentioned, this penetration imaging may be combined with concurrent 3D surface modeling of the teeth. The relative positions of the light source(s) and cameras(s) are typically known, and one or more penetration images may be taken at each position of the wand. Because of the small angle of the viewing vectors that may be used by the wand, the intraoral scanning wand may be configured with just a slight curve, allowing it to fit and be easily maneuvered around the intraoral cavity, unlike wands configured to measure 90° and 180° trans-illumination, which may use a device geometry including side wings to hold the LEDs and sensor(s) so that the wand can wrap around the tooth for the imaging (e.g., see FIG. 2C). The use of small-angle reflectance imaging may enable scanning in buccal and lingual directions, whereas the 90 degree (trans-illumination) scanning as described herein may be limited to scanning in the occlusal direction.

The use of a small angle for penetration imaging may include imaging into the tooth using the wand in a way that enables unconstraint movement around the tooth, and may enable capturing the internal structure data while also scanning for 3D (surface) model data, without requiring a dedicated structure and/or mode of operation. However, the use of small angles between the emitting light and the detector(s) may also be complicated by direct reflections. For example, direct reflection may occur in regions on the surface of the tooth in which the angle between the illumination and the imaging angles are approximately equal (e.g., in the cone of light and imaging NA). These direct reflections may be problematic if they saturate the sensor, or if they show surface information but obscure deeper structure information. To overcome these problems, the apparatus and methods of using them described herein may capture and use multiple illumination orientations taken from the same position. As used herein, in the context of a hand-held wand, taking multiple images from the same position may effectively mean taking multiple images at approximately the same time, so that a significant amount of movement has not occurred. For example, the images may be taken within a few milliseconds (less than 500 msec, less than 400 msec, less than 300 msec, less than 200 msec, less than 100 msec, less than 50 msec, etc.) of each other, and/or correcting for small movements.

Alternatively or additionally, the apparatuses and/or methods may reduce or eliminate the problems arising from saturation with direct reflection by using only the non-saturated pixels. In some variations, the surface information may be subtracted from the penetration images as part of the process. For example, visible light images ("viewfinder images") or surface imaging may be used to remove direct surface reflections.

In general, the apparatuses (e.g., systems) described herein may know the position of the wand at all times based on the surface scan, even when taking images at different (even small angle) angles. Thus, when performing surface and penetrating scans concurrently or nearly concurrently (e.g., within 600 ms, 500 ms, 400 ms, etc. of each other), including interleaving these scans with other scanning types, the position of the wand may be known relative to the object(s) being scanned. Based on this information, the apparatus may estimate which part(s) of the multiple images or signals is/are arriving from the surface and what is/are arriving from deeper structures.

FIG. 4A illustrates an example of a configuration of penetrative light sources 403, 403' (e.g., penetrative spectral range light sources) and camera(s) 405 that may be used as part of an intraoral scanner wand, shown in different positions around the target object (tooth 401). In FIG. 4A, three camera positions are shown, and each in each position the camera is flanked by the pair of LEDs (e.g., 403 and 403') for emitting light in the penetrative spectral range (penetrative wavelength). Alternatively a single light source (e.g., LED) may be used instead of a pair. Different images using the penetrative modality may be taken at different wand positions relative to the teeth. Alternatively, the wand may be configured with multiple imaging sensors (cameras) and multiple light sources, allowing multiple penetration images may be taken at approximately the same time, e.g., by turning on multiple sensors when illuminating from one or more LED orientations (e.g., FIGS. 5G and 5E, etc.). In FIGS. 5A-5I, at least nine different orientations of penetration images may be taken, as shown. Alternatively or additionally, multiple orientations may be taken sequentially, including within a very short time period (e.g., within <500 ms, 400 ms, <300 ms, etc.).

FIGS. 4B-4F illustrate other emitters and detectors for use with of any of the penetrating wavelengths that may be used to take images into the object having semi-transparent strongly scattering regions (e.g., teeth). These images typically collect reflective mode (e.g., light at a penetrative wavelength that has passed into the tooth, and been scattered/reflected from internal structures so that it can be collected by the detector. In FIG. 4B a combination of classic (e.g., 90°, 180°) trans-illumination and small-angle illumination angles are included. In FIGS. 4C-4F the angle of the ray of light emitted and collected is very small (e.g., around 0°) and can be collected by placing the emitter 403, 403' and detector 405 assembly (e.g., CMOS, CCD, etc.) adjacent to each other, as shown in FIG. 4C, combined with each other, as shown in FIG. 4D, or simply sharing a common or near-common beam path, as shown in FIGS. 4E and 4F, which may use reflection or waveguides to direct emitted and/or received light, including the use of beam splitters (dichroic beam splitters) and/or filters.

As mentioned above, any appropriate sensor may be used, including CMOS or CCD cameras, or any other sensor that is capable of detecting the appropriate wavelength, such as near-IR wavelength detectors.

Although applying a penetrative illumination from nearby the sensor (camera) may result in the strongest illumination in the region nearest to the camera, and therefore an unequal distribution of illumination, this is surprisingly less problematic then was expected. In penetration imaging conditions, the light generating the captured image has traveled though the object, and the longer the path, the longer the scattering that will occur, resulting in a more smoothed-out illumination when compared to direct illumination. In front illumination, as results with small-angle illumination, the strongest amount of light will be present in the region nearest to the illuminator (e.g., LED), which will back scatter; this nearby region (e.g., the first 1-2 mm) is an important region for detecting caries. However, it may still be desirable to compensate for the resulting non-uniform illumination profile distribution, as discussed above.

The use of penetration imaging, and particularly small angle illumination/imaging, which may also be described as reflective imaging, may provide information about internal regions (such as cracks, caries, lesions, etc.) of the teeth that would not otherwise be available. The internal feature (or internal region) information may be incorporated into a 3D model, which may be particularly powerful when combined with surface information (e.g., the 3D surface model or depth information). This may allow the user to capture the diagnostics data seamlessly during the 3D scanning procedure while allowing unconstrained movement around the teeth to capture data from different angles, providing a 3D model of the tooth interior.

Combining Surface Data with Internal Feature Data

As mentioned above, it may be particularly beneficial to combine and/or coordinate 3D surface data with any of the internal feature data (including, but not limited to, penetration imaging data). For example, internal feature data such as penetration imaging data may be combined with surface data (surface imaging data) collected from the same or approximately the same position of an intraoral scanner so that the same coordinate system may be applied to both types of data.

As described above, a color 3D intraoral scanner such as the one shown in FIG. 1A, may be equipped with illumination devices emitting light at two or more different spectral ranges for capturing a variety of surface and internal features. The data (e.g., surface data and internal feature data) collected may be correlated and combined to form a 3D model including information about lesions, decay, and enamel infractions as well as teeth internal structure. The internal feature data may be gathered by any appropriate penetrative imaging technique, including the reflective (e.g., small-angle) illumination and imaging, and trans-illumination imaging techniques described above or by other techniques known in the art, including, but not limited to UV/blue fluorescence and red light fluorescence.

The internal feature data may be collected (and may include lesion and internal teeth structure images) and combined with the surface data including color 3D surface model data for the teeth. The combination of surface and internal data may be expressed as a 3D model or 3D rendering, which may include a full color 3D data (including models and renderings) of the lesions and tooth internal structure as well as the surface of the teeth, gums and any other scanned portion of the intraoral region. Although in some variations the internal and surface data may be coextensive, in some variations the surface data may be more extensive than the internal data; for example, the 3D model may include internal data for only a portion of the 3D model, while other regions may not include (or may include only incomplete) internal features.

In use, a 3D model of a tooth or teeth including both surface and internal elements may be analyzed either automatically or manually, and internal features may be identified and/or marked. For example, lesions, caries and/or cracks may be labeled, including color coding, e.g., according to their type and level of risk they represent in one or more images that may be provided and/or as part of a data file that is generate to show these images. Alternatively or additionally, a written transcript/description of these findings may be provided.

An intraoral scanner for generating a 3D model including both surface and internal structure as described herein may include one or more image sensors. For example, the image sensor may be configured for capturing color 3D (surface) images or data, and may also capture lesion and teeth internal structure images. Optionally or additionally, the system may have multiple sensors. The surface data may be acquired using an intraoral scanner in any appropriate manner. The intraoral scanner is generally configured to scan (via the wand) in both surface and internal imaging modes, including concurrently. For example, surface data may be captured using a color intraoral 3D scanner by confocal, stereo vision or structured light triangulation or any other 3D surface scanning technology capable of intraoral scanning.

Figure 10B:
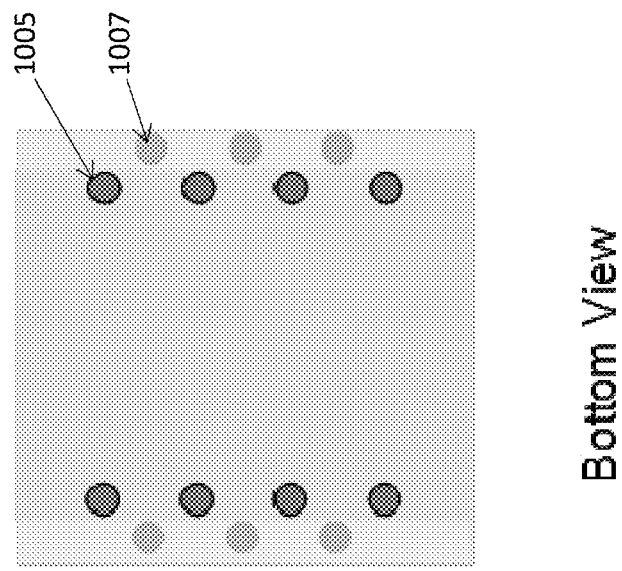
FIG. 10B shows an example of a bottom view of the intraoral scanner, showing the plurality of sensors and light sources.
Figure 10A:
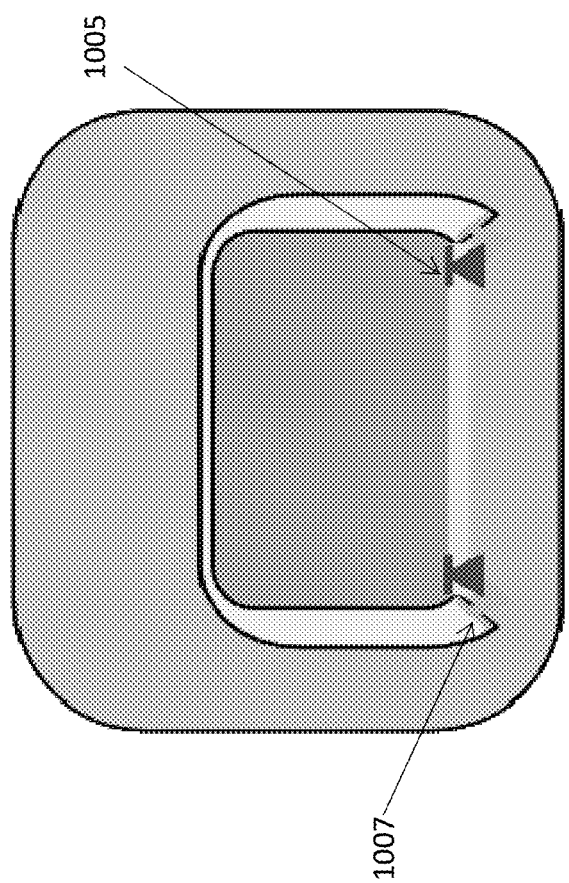
FIG. 10A shows an example of a front view of one example of an intraoral scanner front end.

As illustrated in FIGS. 10A and 10B, the illumination light sources (including the lights sources for the first modality (e.g., surface scanning), for the second modality (e.g., penetrative imaging such as penetration imaging), and/or for the third modality (e.g., color scanning) may be located at the front tip of the intraoral scanner wand, e.g., near the scanned objects or inside the scanner head. The front tip illumination configuration may be configurable according to the application needs with or without any particular light source suitable for the desired diagnostics feature by changing the front tip. The light source(s) and the sensors (e.g., cameras) may be arranged in any appropriate manner, including as shown in FIGS. 10A-10B and 4. For example, the light sources and cameras may be adjacent to each other. In some variations the system or method uses miniature sensors 1005, 1007, e.g., located at the front tip in a wrap-around manner, to capture stereoscopic 3D internal feature data (e.g., images) and/or for facilitating penetration imaging in a more efficient fashion.

As mentioned, in some variations, the lesion/internal tooth structure capture methods may be any combination through-tooth penetration imaging, including one or more of: trans-illumination, red light laser fluorescence and blue/UV laser fluorescence, etc. In general, the internal feature data may be used in combination with the surface data, including the coordinate system of the surface data, to reconstruct a 3D representation of the tooth structure. For example a 3D reconstruction of the tooth data may be reconstructed by an algorithm combining several (e.g., multiple) 2D images using the any of the internal feature imaging techniques described herein, typically taken at several different angles or orientations.

Data captured by the intraoral scanner, including in particular the 3D model of the tooth/teeth having both surface and internal features, may be stored by the device and/or transmitted to a physician, medical record, dentist, or the like. For example, any of the data captured by the intraoral scanner, i.e. a color 3D model combining the topography of the teeth lesions and internal teeth structure, may be maintained in a designated patient database for longitudinal monitoring and preservation of patient's oral health. The data may be annotated (including dating and/or markings referencing internal features) or unannotated.

For example, longitudinal comparison in time may be done using the 3D models described herein at one or more levels, including by comparing across time: surface changes, visual color changes, internal/volumetric changes, or any combination of these. For example, each can be shown as before and after e.g., by manual evaluation, or subtracted and compared automatically. In some embodiments, two or more 3D models may be superimposed with one another on a display to highlight differences between the 3D models. The superimposed models may help highlight changes in enamel thickness, dentin volume, color, opacity, and/or decreases/increases in caries size, for example. Optionally, a 3D model of a patient's dentition from an earlier date may be morphed into a 3D model of the patient's dentition at a later date to help highlight any changes in the patient's dentition over time. In some embodiments, a time series of 3D models may be progressively morphed from one to the next to provide a video or animation of the changes in the patient's dentition. Automatic comparison may be done by applying or converting to a common coordinate system, which may in particular be done using surface information (e.g., based on the 3D surface model data that is included as part of the generated 3D volumetric model). Typically, all three types of data (surface, color, volumetric, etc.) are interconnected by the same coordinate system, as already described above. In general the method and apparatuses described herein, including the 3D models, may be used to predict future dental or orthodontic conditions in a patient as described, for example, in U.S. 2016/0135925, incorporated by reference in its entirety.

When comparing scans, including 3D volumetric scans, the scans may be adjusted or normalized relative to each other for automatic, semi-automatic or manual comparison. For example, a scan of the tooth or teeth (e.g., a full jaw scan, partial scan, etc.), may not be 100% repeatable, particularly to a precision higher than the voxel resolution. To compare voxel-by-voxel, a matching and/or morphing function may be applied to one or both scans to allow more direct comparison. For example, a matching and/or morphing function may be used. A morphing function may bring the external surfaces to match and align, allowing a voxel-to-voxel comparison. This may also allow comparison of full scans to partial scans.

As mentioned above, in general, captured data may be stored and saved in the same coordinate system. Thus, surface data (including 3D surface model data) may use a coordinate system (e.g., x, y, z; so that the 3D surface model is $S(x,y,z)$) and the internal feature data may use or reference the same coordinate system (e.g., so that the internal feature data is $I(x, y, z)$). Thus, common features or structures may have the same address (coordinates) between both data sets.

Figure 6:
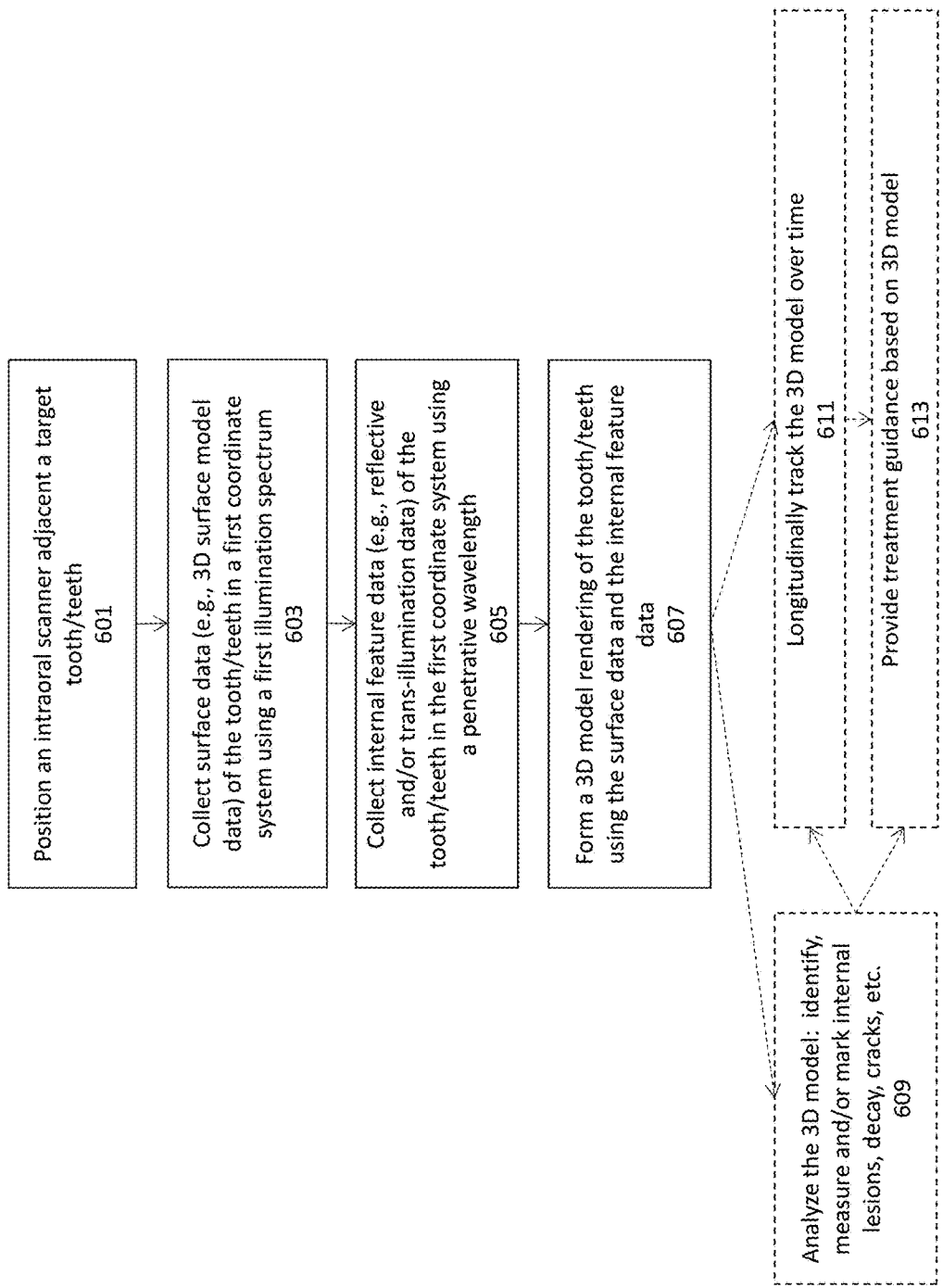
FIG. 6 is a diagram schematically illustrating one method of generating a model of a subject's tooth or teeth having both surface and internal features.

FIG. 6 is a diagram illustrating an example of a method for generating a 3D model or rendering of a tooth or teeth using surface data and internal feature data. In this example, a hand-held intraoral scanning wand (scanner) may first be positioned adjacent to a target intraoral region 601 to being scanning. Once scanning is initiated, the apparatus may collect surface data (e.g., 3D model surface data) including depth information in a first coordinate system 603. The surface data may typically be collected while illuminating the sample using a first illumination spectrum, such as visible light (e.g., monochromatic or broadband light). Internal feature data may also be collected, e.g., using a second illumination spectrum (which may include just a single wavelength or small range of wavelengths) that is/are penetrative into the tooth/teeth 605. This data may use the same coordinate system as the surface data, which may be accomplished as described in greater detail below. Once collected, the data may be analyzed, and/or filtered (including subtracting, smoothing, etc.), and combined to form a 3D model rendering of the intraoral cavity (e.g., tooth, teeth, gums, jaw, etc.) using both the surface data and the internal feature data 607. For example, when building the 3D geometry of the internal feature data (which is typically two-dimensional in nature), the algorithm may use the reference to the known 3D surface scan to improve the accuracy of the internal feature data.

In general, in any of the apparatuses and methods described herein, the internal feature data collected 605 may be used to reconstruct a volumetric model of the tooth or teeth including the internal features. In particular, tomographic reconstruction (e.g., optical tomography) may be used. A fully volumetric modeling may be used. Typically, every penetrating light ray can either be refracted, reflected, scattered and/or absorbed (including combinations of these), depending on the material properties and the light used. In some variation, the methods and/or apparatus may divide the volume of the tooth into small voxels and for each voxel, estimate these four parameters (refraction index, reflection, scattering, absorption) based on the imaging data collected, using the coordinate system corresponding to the coordinate system of the surface data. More complex models (e.g., based on non-isotropic scattering or complex surface scattering) may also be used. Once a set of parameters for each voxel is estimated, the method or apparatus may compare how well the captured images, fit this model. Thus in some variations the apparatus and/or method may seek to minimize the difference between the captured images and the modeled, predicted image. An initial guess may be built from the 3D surface capture, including estimates of enamel parameters and width.

Alternatively or additionally, multi-surface modeling may be used. Multi-surface modeling assumes a set of material (and in some cases uniform) in optical properties, such as properties for air, dentin, and enamel (but may include more than these three). This technique may seek to find the boundaries between the materials. There are multiple ways to accomplish this, including using techniques similar to what is described above for the full volumetric modeling, but without the voxels representation. Alternatively or additionally, a contour line method may be used in which a first (e.g., air-enamel) boundary is given from the 3D surface capture, and then, by finding the edges of regions in the 2D penetrating images, a smooth 3D surface may be approximated that best fits this silhouette. See for example "3D Shape from Silhouette Points in Registered 2D Images Using Conjugate Gradient Method. Andrzej Szymczaka, William Hoffb and Mohamed Mahfouzc," the entire contents of which are incorporated herein by reference. Apart from contours, other features, like points, corners, as known in the art, may be used. These features may be detected from the different viewpoints, and located in 3D by triangulation, and are part of the boundaries.

In practice, recording the surface data and internal feature data in the same coordinate system may be achieved by scanning both the surface and the internal features at the same position and/or time. As mentioned, in a hand-held user controlled intraoral scanning device (e.g., wand) it may be difficult to scan the same region at different times in different wavelengths. Thus, any of the apparatuses and methods described herein may coordinate scanning at the different modalities or modes (e.g., surface data scanning and/or internal features/penetrative data scanning).

Figure 7:
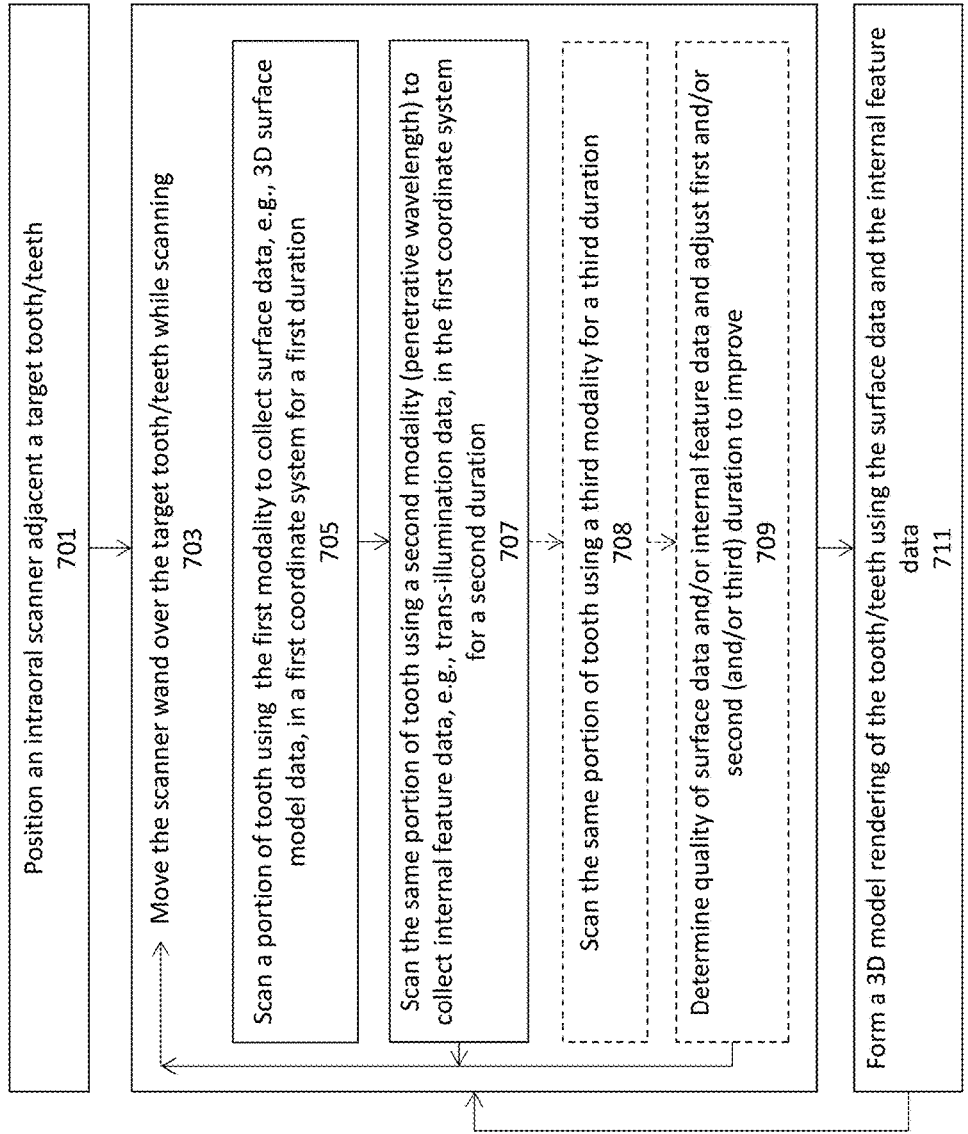
FIG. 7 is a diagram illustrating one variation of a method of generating a model of a subject's teeth when having both surface and internal features by cycling between different scanning modalities (e.g., surface scanning, penetration imaging, etc.).

For example, FIG. 7 illustrates one method in which the intraoral scanner alternates between surface scanning and one or more other scanning modalities (e.g., internal feature scanning, such as penetration imaging scanning). In FIG. 7, after positioning the scanner adjacent to the target intraoral structure to be modeled 701, the wand may be moved over the target while the apparatus automatically scans 703 the target for both surface data and internal data. As part of this method, the system may alternate (switch) between scanning a portion of the tooth using a first modality 705 (e.g., surface scanning, using emitting light in an appropriate wavelength of range of wavelengths) to collect surface data such as 3D surface model data and scanning with a second modality 707 (e.g. a penetrative wavelength). After an appropriate duration in the first modality, the method and apparatus may briefly switch to a second modality (e.g., a penetrative wavelength or range of wavelengths) to collect internal feature data for a brief time period (second duration) 707 over approximately the same region of the object scanned in the surface mode. At the time of the switch, the coordinate system between the two modalities is approximately the same and the wand is in approximately the same position, as long as the second duration is appropriately short (e.g., less than 500 msec, less than 400 msec, less than 300 msec, etc., less than 200 msec, less than 100 msec, less than 50 msec, etc.). Alternatively or additionally, the method and apparatus may extrapolate the position of the wand relative to the surface, based on the surface data information collected immediately before and after collecting the internal data. Thus, in any of the methods described herein, including as shown in step 703 of FIG. 7, the apparatus may interpolate the positions between each scan (e.g., first modality scan, such as a surface scan, a second modality scan, such as a penetrative, e.g., near-IR scan or scan(s) and a third modality scan, such as a color scan, etc.). This interpolation may correct for the small but potentially significant movement of the wand during scanning. In particular, when coordinating between the surface and internal structures, in which the scanning is being manually performed, interpolating (and/or extrapolating) to approximate the more accurate 3D position of the teeth (or of the teeth relative to the scanning wand) for each scanned image. The portion of the teeth scanned using a penetrative wavelength may therefore be interpolated proportionally between the surface scans done before and after the penetrative scan(s). See, e.g., FIG. 8, described below, showing an exemplary relative timing of the scans in each mode. Alternatively or additionally, the position of the teeth and/or wand/scanner during a scan may be extrapolated from the prior surface scan position based on the rate of movement of the scanning wand (e.g., as estimated from the rate of change across the surface from prior surface scans, and/or motion sensor(s) in the wand). Correcting the coordinate system of each scan in this manner (for example, in x, y and z position, and orientations angles) may allow images in different modalities to be tightly registered relative to each other, regardless of how the scanner is manipulated by the user. In penetrative scans, in which multiple scans may be taken from the same relative position and used to reconstruct internal features, the accuracy of the coordinate system may allow higher resolution modeling of the internal features.

In general, when collecting penetrative wavelength images, the light emitted and received may have different polarizations. In the reflective light mode, for example when using small-angle penetration imaging, some of the energy is penetrating, but some is also reflected from the surface. It may be preferable to block this direct surface reflection, which may be done in any appropriate manner, including using polarization. For example, to block the surface reflection the sample (e.g., tooth) may be illuminated with a penetrative wavelength at a specific polarization, and this polarization may be blocked in the imaging path. This polarization may also be helpful to block direct light from the illumination source in trans-illumination (e.g., where there is a direct line of sight to the illuminator as in 180° trans-illumination).

Although many of the methods and apparatuses described herein include switching between modes to distinguish surface and internal structures, in some variations, they may be truly simultaneously detected, for example, using a dichroic beam splitter and/or filter. Thus, by separating out the wavelengths and/or polarization that are penetrative and include internal reflections and/or scattering from those including only (or primarily) surface features, the surface data may be collected and processed separately from the internal features, and these two data sets may be recombined later; this technique may inherently use the same coordinate system.

Figure 2E:
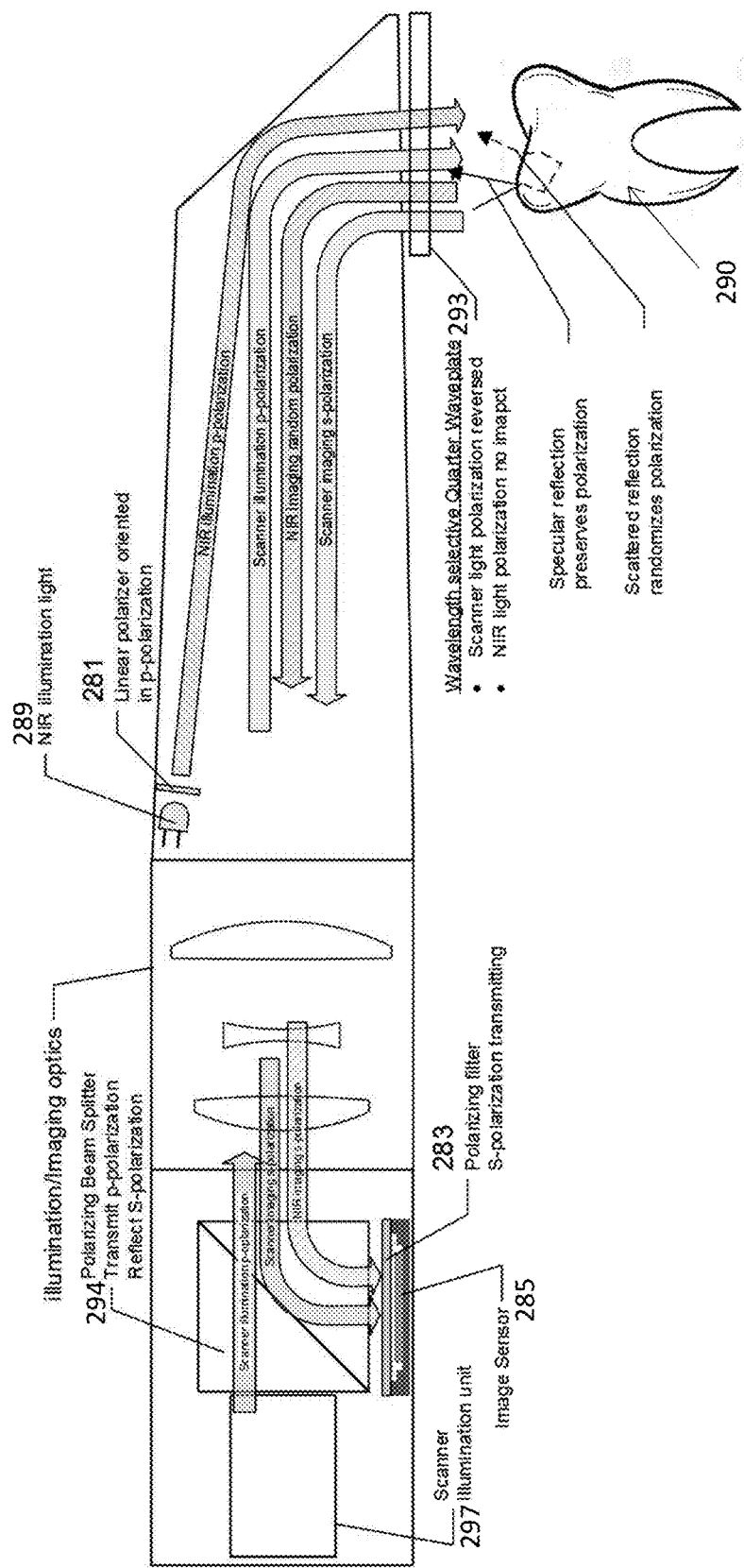
FIG. 2E shows a schematic of an intraoral scanner configured to do both surface scanning (e.g., visible light, non-penetrative) and penetrative scanning using a near infrared (IR) wavelength. The scanner includes a polarizer and filters to block near-IR light reflected off the surface of the tooth while still collecting near-IR light reflected from internal structures.

For example, FIG. 2E shows a schematic of intraoral scanner configured to do both surface scanning (e.g., visible light, non-penetrative) and penetrative scanning using a near infra-red (NIR) wavelength (at 850 nm in this example). In FIG. 2E, the scanner includes a near-IR illumination light 289 and a first polarizer 281 and a second polarizer 283 in front of the image sensor 285 to block near-IR light reflected off the surface of the tooth 290 (P-polarization light) while still collecting near-IR light scattered from internal tooth structures/regions (S-polarization light). The NIR light illuminates the tooth in P-polarization, and specular light reflected from the surface of the tooth, e.g., the enamel, is reflected with specular reflection hence its P-polarization state is conserved. Near-IR light penetrating the internal tooth features, such as the dentin, is scattered resulting in random polarization (S and P). The wavelength selective quarter waveplate 293 does not modify the polarization of the near-IR light (e.g., it leaves the polarization state of the near-IR light being delivered unchanged) but changes the polarization of the returning scan light from P to S such that only surface reflection are captured in the scan wavelength. The returning near-IR light, having a mixture of S and P polarizations, is first filtered through the polarization beam splitter (PBS) 294 and polarizing filer 283 such that only the S-polarization is transmitted to the image sensor. Thus only the near-IR S-polarization light, coming from the tooth internal structures, is captured by the image sensor while specular light, having the original p-polarization, is blocked. Other intraoral scanner configurations with or without polarization filters such as those shown in FIG. 2E may be used as part of the probe.

In FIG. 2E, the surface scan may be performed by illuminating the surface (using the scanner illumination unit 297), illuminating in p-polarization, and the polarization is reversed by the wavelength-selective quarter waveplate 293 (transmitting S-polarization light to the image sensor).

As shown in FIG. 7, the scanning scheme, including the duration of the scanning modalities such as the second scanning modality to determine internal feature data, may be manually or automatically adjusted 709. For example, scanning procedure (time sharing and sequence) may be varied per case and the system may automatically optimize the scanning resources so as to get high-quality scans and/or more complete reconstructions. The method or apparatus may determine the quality of the scanned data 709, such as the quality of the scanned surface data, and may adjust the scanning duration(s) (e.g., the second duration) accordingly. An estimate of quality may be made automatically, for example, based on blurring, over- or under-saturation, etc. For example, the duration of a scanning scheme may be dynamically adjusted (e.g., increased or decreased) based on the quality of the scans in this modality; if the prior x scans in this modality are below a first (e.g., minimum) quality threshold (quantifying one or more of: blurring, over-saturation, under-saturation, etc.) the scan duration for that modality, $d_i$, may be increased. Scan time may be reduced if the duration of the scan is above a minimum duration and the quality is above a second quality threshold (which may be the same as the first quality threshold or greater than the first quality threshold). Reducing the scan duration may allow the duration of other scanning modalities to increase and/or the rate of switching between scanning modalities to increase. Alternatively or additionally, the scan duration for a modality may be adjusted based on the completeness of the 3D model being reconstructed. For example, when scanning a region of the 3D model having a more complete surface model (e.g., regions over which the surface model has already been made), the duration of the surface scan may be decreased, and the duration of the penetrative scan (e.g., a reflective scan using a near-IR wavelength, or a trans-illumination scan using a near-IR wavelength) may be increased to increase the resolution and/or extent of the internal structures. Similarly, the frequency of the scanning in each mode may be adjusted dynamically by the apparatus.

Any of the methods and apparatuses described herein may also be configured to give feedback to the user to slow down or add scans from a specific angle by showing these missing regions or angles in the 3D graphical display.

Figure 8:
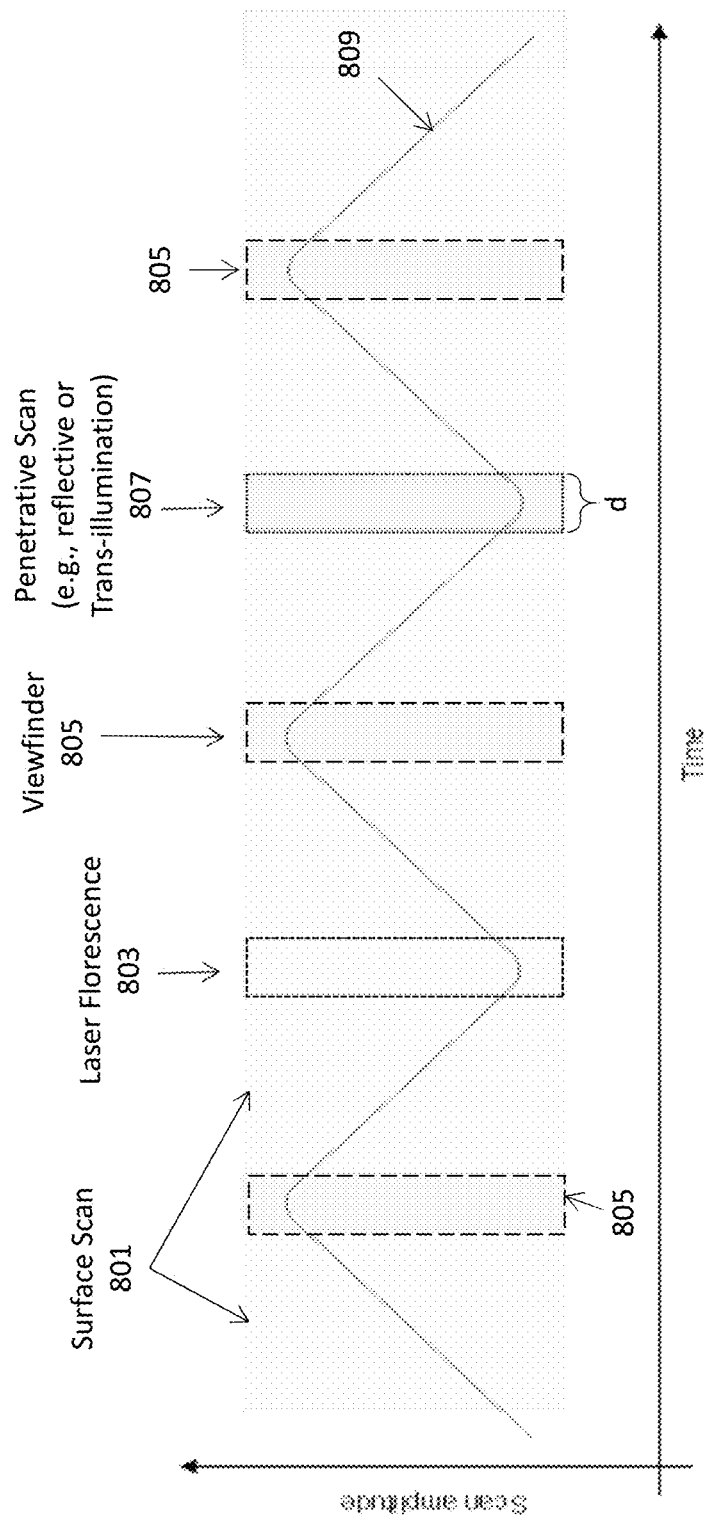
FIG. 8 is a graphical example of one a timing diagram for scanning a sample (e.g., tooth) to generate a model having both surface and internal features cycling between different scanning modalities (showing surface scanning, laser florescence, viewfinder and penetration imaging modalities).

As illustrated in FIG. 7 (e.g., optional step 708) and in FIG. 8, more than two scanning modalities may be used. FIG. 8 illustrates an exemplary method of operating an intraoral scanner so that it switches between different scanning modalities, including surface scanning 801, laser florescence 803, color visible light scan (viewfinder) 805, penetration scanning 807, UV scanning, etc. The system may initially switch between the scanning modalities with a default scanning scheme; as mentioned, the system may then (in real time) analyze the data coming from each of the scanning modalities and may prioritize the scanning modalities that have less complete data, for example, by expanding the frequency and/or duration (d) that they are scanned. In some embodiments, the system may compare the gathered data from the one or more of the scanning modalities to predetermined data resolution thresholds in order to determine which scanning modalities to prioritize. For example, a system may increase the frequency or duration of surface penetrative imaging after determining that sufficient surface data had been gathered with a surface imaging modality and that internal feature data resolution is still insufficient. Alternatively or additionally, in some variations scanning may be done for different modalities simultaneously. Once sufficient scanning area has been completed, the combined 3D model of the intraoral region may be assembled using the scanned data 711; alternatively the 3D model may be continuously assembled as the scanning is ongoing. The frequency of the scanning 809 is shown by the frequency of the scan amplitude in FIG. 8; surface scans are performed at the maximum of the scan amplitude and penetrative scans at the minimum of the scan amplitude as the depth of the confocal scanning increases and decreases. The frequency of the depth scanning 809 may be increased or decreased dynamically during scanning. For example, to allow longer scanning duration scans, or to accommodate for a faster-moving wand/scanner by the user. In some variations the wand may include a motion sensor (e.g., an accelerometer, etc.) to detect movement rates, and the scanning rate(s) and duration(s) may be adjusted based on the detected motion of the scanner.

As shown in FIG. 6, the resulting 3D model including surface and internal structures may be used in a variety of ways to benefit subject (e.g., patient) health care. For example, the 3D model may be used to identify (automatically or manually) and analyze lesions, caries and/or cracks in the teeth. The 3D model may be used, for example, to measure size shape and location of lesion including decay, to assess the type of decay based on translucently, color, shape, and/or to assess the type of surface issues based on surface illumination e.g. cracks, decay, etc. 609.

This 3D data (or data derived from it) may be monitored over time for a particular patient 611. For example, the 3D data may be checked for changes in shape size and type over time either visually or using an algorithm.

In general, the 3D data may be annotated. For example, after a first scan, a clinician may mark areas of interest which may be manually or automatically assessed in following scans. In addition the 3D data may be used to help treat or provide treatment guidance and monitoring 613. For example, if a clinician decides to restore a tooth, the 3D data showing surface and internal regions generated as described herein may be used to provide reduction guidelines for the tooth to ensure the removal of the decayed volume. During the procedure, additional (e.g., intermediate) scans may be made to provide the doctor with further direction and immediate feedback on the reduction.

Figures 9A, 9B:
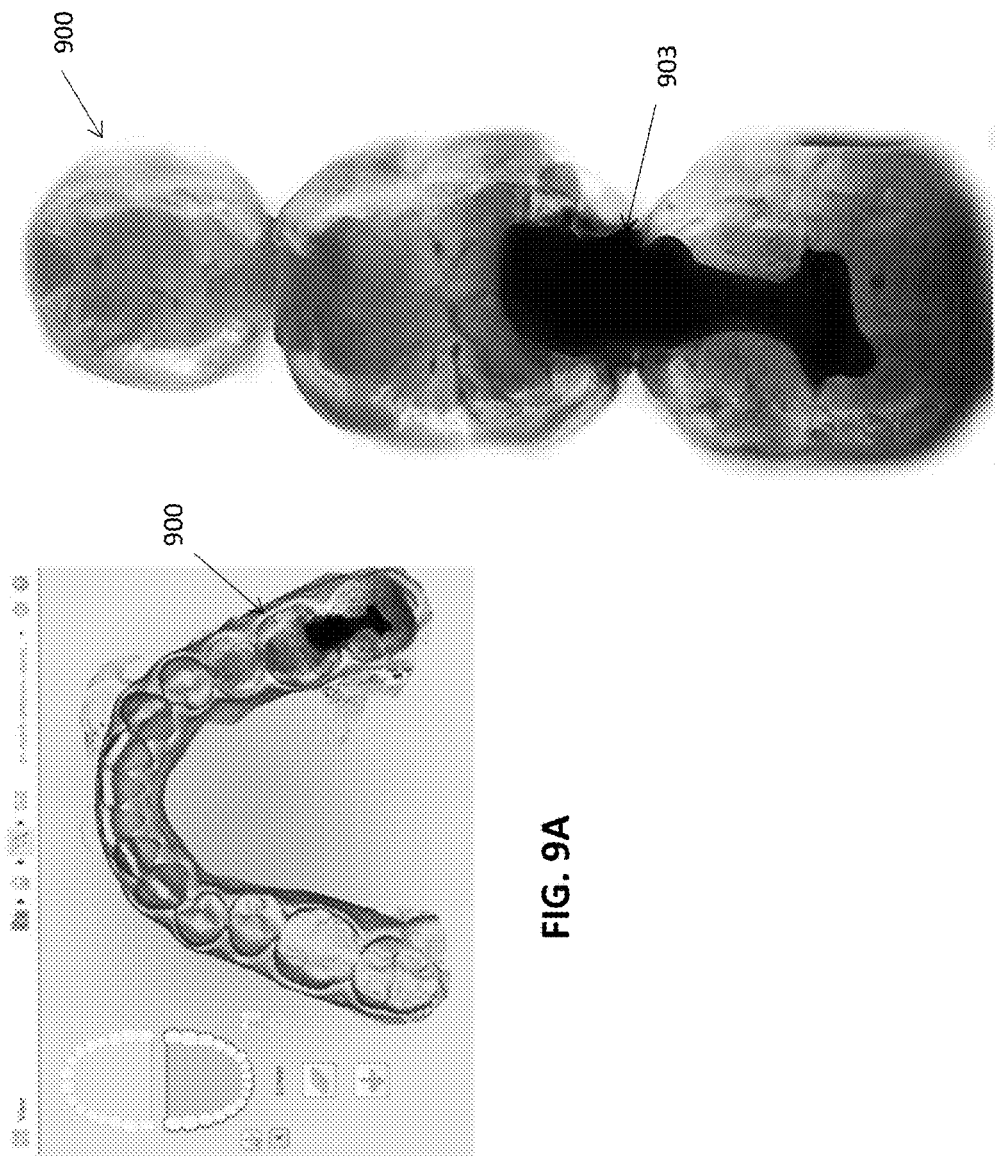
FIG. 9A illustrates one example of an overlay of the penetration images in on a 3D surface model of the teeth, showing the image penetration panorama (in which penetrating images are stitched together to form the panorama)
FIG. 9B illustrates the portion of the model reconstruction of FIG. 9A including the surface and internal features. Note that in FIGS. 9A and 9B, the overlay showing the internal structures is not a volumetric reconstruction.

FIGS. 9A and 9B illustrate one example of a 3D model 900 rendering of an intraoral region of a subject including both surface (total surface is shown in the projection of FIG. 9A) and internal structures, shown in the enlarged region in FIG. 9B. In FIG. 9B, the darker region 903 apparent from the penetration imaging using 850 nm light combined with the 3D surface data, shows a region of interest. The region of interest may be a carious region or a dental filing, or the like. The ability to manipulate images like this to rotate, zoom, section and otherwise view the 3D model or regions of the 3D model may greatly enhance the treatment and understanding of a subject's dental needs.

Depth Scanning

FIGS. 11A-11I illustrates one example of volumetric modeling of internal tooth structure using a penetrative wavelength such as near-IR trans-illumination ("TI"). In this example, a lesion in the tooth may be detected when light is bellow lesion or at the level of the lesion. When the light is below the lesion, the lesion absorbs the light, thus lesion appears as dark spot in the image. In FIG. 11D, a tooth having a lesion is shown with a scanner sensor 1101 above the tooth (positioned above the occlusive surface of the tooth). The scanner includes one or (as illustrated in FIGS. 11D-11F) two light sources (emitters) 1105, 1105', emitting near-IR light, as shown by the arrows. The light penetrates the tooth and the sensor 1101 detects the occlusion of light due to the lesion, as shown in FIG. 11A.

Moving the scanner with the light source upwards (i.e., moving the wand of the scanner higher along the tooth) will produce a change in the lesion image as shown in FIG. 11B. The corresponding position of the light sources relative to the tooth is shown in FIG. 11E schematically, and in the illustration of FIG. 11H. As the scanner is moved further up the tooth, the dark spot representing the lesion 1113 will start shrinking until completely disappearing, turning into light saturation. Finally, when the light source 1105, 1105' is above the lesion, the dark spot is no longer present (e.g., FIG. 11C) and only the central occlusive region (the dentin) is shown. As already discussed above, the outer surface of the tooth and gingiva may be concurrently scanned using a separate light source, providing the 3D outer surface of the tooth, and therefore the distance from the tooth to the scanner. This information, as described above, may be used to map the lesion's depth and/or shape.

Such depth scanning may be manually or automatically performed, and may be useful for providing a backup and/or alternative to volumetric modeling (e.g., 0-degree volumetric modeling) of the tooth/teeth. Indeed this vertical scanning of the teeth (which may be performed in any direction (bottom to top of tooth, top to bottom, etc.) may be used as one type or sub-type of volumetric scanning that may provide information on shape and position of dentin and/or lesions.

For example, the method of vertically (z-axis) scanning of the teeth/tooth with an intraoral scanner, particularly one having both a penetrative (e.g., near-IR) and surface scanning wavelength(s), may provide an alternative method of volumetric scanning. In general, data may be acquired by scanning up or down (in the z-axis) the tooth/teeth.

As discussed above, one configuration for the scanning devices described may optically image the inside region of a tooth/teeth using, e.g., trans-illumination (through the sides) at an angle, such as a 90° angle, between light source and camera. When a dental caries is present in the tooth, viewing the tooth with a penetrative wavelength, e.g., in trans-illumination, from above (occlusion view) may reveal the caries as an occlusive region. Depending on the relative z (depth) position of the light source with respect to the caries, an occluded region corresponding to the caries will be present in the x,y image. Thus scanning through the z-axis (depth) as described above may be used to determine one or both of z-position and shape of the caries. In some variations, a method for scanning using a penetrative wavelength (or a penetrative and surface scanning) may begin with illuminating from the sides and imaging from above and placing light as close as possible to gum line. The method may then proceed to move up along the z axis of tooth, moving away from the tooth's occlusive surface. This may allow the light to hit a lesion from different depths (in the z-axis). As illustrated in FIGS. 11A-11C, a caries will be initially present, and as the scanner is drawn upwards, may shrink in the imaging plane (x,y) until it is no longer blocking the light. Any of these methods may also calculate or determine the z-position along the tooth as the scanner is moved upwards, so that the relative depth on the tooth is known, and therefore the depth of the lesion is from the enamel layer. From this information, the dimensions of the lesion may also be determined (e.g., an estimate of how far along the z-position the lesion extends), as well as the breadth and extent (e.g., how far it extends in x,y) may also be determined. Along with the surface 3D model, showing the outer shape of the tooth, this information may be used to provide a model of the tooth and the overall lesion.

Thus, using both a penetrative wavelength (e.g., near IR) and the non-penetrative (surface scanning) wavelength, a model of both the external and internal structures of the tooth may be determined. Depth scans (even non-contiguous scans) along the z-axis of the tooth may be particularly useful for determining the depths and/or dimensions of internal structures within the tooth/teeth. In any of the methods described herein, as discussed above, a 3D scan of the tooth may be performed concurrently with the penetrative (including depth) scanning.

Thus, in any of the methods of scanning a tooth as described herein, the method may include determining a depth (z) dimension for each scan, showing the relative depth of the light source(s), e.g., the near-IR light source(s) relative to the tooth. This information may be provided by the 3D surface scan corresponding/correlating to the penetrative scan. Depth information (e.g., knowing how much the scanner has been moved in the z-axis) may provide substantial volumetric information.

As mentioned above, the depth (z) scanning described herein may be performed manually or automatically. For example, this scanning may be performed by manually scanning the wand up and along the teeth. During scanning both concurrent 3D surface modeling and internal modeling/imaging may be continuously performed during scanning. Any appropriate scanning rate (e.g., 20 scans per second) may be done. Thus, a user may scan at a reasonable speed, and output may be done in real-time, including displaying a lesion, and/or lesions (and any other internal structures) may be displayed later following analysis by the software. In one example, concurrent scanning may be performed so that the surface scanning (using a laser) may be done for an approximately 35 ms period, followed by a window of 15 ms for other types of imaging, including color, near IR, etc., and repeated during the scanning period. In some examples, the near-IR scanning may be done for 5 ms within the 15 ms window. Shorter sampling may be beneficial (e.g., shorter than 20 ms, shorter than 15 ms, shorter than 12 ms, shorter than 10 ms, shorter than 7 ms, shorter than 5 ms, etc.), as it may reduce smearing of the image. However, shorter scan times may require higher energy, e.g., more power/current to the penetrative light source. Imaging data may be collected throughout. Alternatively, scanning may be done for longer or shorter periods of time (e.g., surface scanning, near IR scanning, color scanning, etc.), and/or at the same time (e.g., laser surface scanning and near-IR concurrently, using different emitters/detectors, for example). In this manner, e.g., concurrent or rapid alternating (within 200 ms, within 150 ms, within 100 ms, within 50 ms, etc.) of surface and penetrative scanning, or any other different types of scanning, may permit coordination between the surface (e.g., 3D) molding and internal structures as described above.

Imaging Internal Structures Using Scattering Coefficients

Also described herein are methods and apparatuses for generating images of internal structures from within a tooth or other semi-transparent, strongly scattering object) based on a plurality of penetrative images (also referred to herein as "penetrating images") through the object in which the position of the camera (relative to the object) is provided. These methods and apparatuses may therefore generate images, including three-dimensional models, of internal structures without requiring a model of the external surface.

For example, described herein are methods and apparatuses, including computing device readable media, for reconstructing a volumetric structure from an object including semi-transparent strongly scattering regions, such as a tooth. More specifically, these apparatuses (e.g., systems) and methods may provide techniques for reconstructing an inner structure of an object, such as the dentin in the teeth.

Generally, objects that are semi-transparent and strongly scattering to a specific wavelength can be imaged according to the methods (and using any of the apparatuses) described herein. If the location and orientation of the camera with respect to the object is known, the inner structure of the object can be reconstructed with a low computational complexity proportional to the volume being reconstructed and the number of images.

Any of the intraoral scanners that take images through a subject's intraoral region (e.g., tooth or teeth, gums, jaw, etc.) described herein and also provide information on the relative position of the scanner (e.g., the camera of the scanner taking the image), may be used. For example, returning to FIGS. 1A and 1B, FIG. 1A illustrates one example of an intraoral scanner 101 that may be configured or adapted as described herein to generate 3D models having both surface and internal features. As shown schematically in FIG. 1B, an exemplary intraoral scanner may include a wand 103 that can be hand-held by an operator (e.g., dentist, dental hygienist, technician, etc.) and moved over a subject's tooth or teeth to scan both surface and internal structures. The wand may include one or more sensors 105 (e.g., cameras such as CMOS, CCDs, detectors, etc.) and one or more light sources 109, 110, 111.

In FIG. 1B, two separate light sources are shown: a first light source 109 configured to emit light in a first spectral range for detection of surface features (e.g., visible light, monochromatic visible light, etc.) and a second light source 111 configured to emit light in a second spectral range for detection of internal features within the tooth (e.g., by trans-illumination, small-angle penetration imaging, laser florescence, etc., which may generically be referred to as penetration imaging). Although separate illumination sources are shown in FIG. 1B, in some variations a selectable light source may be used. The light source may be any appropriate light source, including LED, fiber optic, etc. The wand 103 may include one or more controls (buttons, switching, dials, touchscreens, etc.) to aid in control (e.g., turning the wand on/of, etc.); alternatively or additionally, one or more controls, not shown, may be present on other parts of the intraoral scanner, such as a foot petal, keyboard, console, touchscreen, etc.

In addition, the wand 103 may also include one or more position and/or orientation sensors 123, such as an accelerometer, magnetic field sensor, gyroscope sensors, GPS etc. Alternatively or additionally, the wand may include an optical sensor, magnetic sensor, or other some combination thereof, for detecting the relative position of the wand, and particularly of the camera(s) with respect to the object being imaged (e.g., a tooth or teeth). Alternatively or additionally, the apparatus may detect the relative position of the wand based on the surface images (e.g., surface scanning) and/or viewfinding scan taken as described above.

In general, any appropriate light source may be used, in particular, light sources matched to the mode being detected. For example, any of these apparatuses may include a visible light source or other light source for surface detection (e.g., at or around 680 nm or other appropriate wavelengths), a visible light source (e.g., white light source of light) for traditional imaging, including color imaging, and/or a penetrating light source for penetration imaging (e.g., infrared and/or near infrared light source).

The relative positions of the light source(s) and cameras(s) are typically known, and one or more penetration images may be taken at each position of the wand. The positions of the light source(s) and camera(s) can include three numerical coordinates (e.g., x, y, z) in a three-dimensional space, and pitch, yaw, and roll of the camera.

The intraoral scanner 101 may also include one or more processors, including linked processors or remote processors, for both controlling the wand 103 operation, including coordinating the scanning and in reviewing and processing the scanning and generation of the 3D model including surface and internal features. As shown in FIG. 1B the one or more processors 113 may include or may be coupled with a memory 115 for storing scanned data (surface data, internal feature data, etc.). Communications circuitry 117, including wireless or wired communications circuitry may also be included for communicating with components of the system (including the wand) or external components, including external processors. For example the system may be configured to send and receive scans or 3D models. One or more additional outputs 119 may also be included for outputting or presenting information, including display screens, printers, etc. As mentioned, inputs 121 (buttons, touchscreens, etc.) may be included and the apparatus may allow or request user input for controlling scanning and other operations.

Any of the apparatuses and methods described herein may be used to scan for and identify internal structures such as cracks, caries (decay) and lesions in the enamel and/or dentin. Thus, any of the apparatuses described herein may be configured to perform scans to detect internal structures using a penetrative wavelength or spectral range of penetrative wavelengths. Although a variety of penetrative scanning techniques (penetration imaging) may be used or incorporated into the apparatus, trans-illumination and small-angle penetration imaging, both of which detect the passage of penetrative wavelengths of light through the tissue (e.g., through a tooth or teeth), may be of particular interest.

The methods and apparatuses for visualization of the enamel-dentin area using a penetrative wavelength (such as, for example, 850 nm) described herein may acquire a plurality of projections or orientations from a single position of the scanner relative to the tooth/teeth; in particular three or more orientations or projections may be taken at each position. Taking multiple (e.g., 3 or more) projections may provide better imaging, as it may produce multiple (e.g., 3 or more) images through the tooth from a particular location of the wand relative to the tooth/teeth.

FIG. 12 illustrates an example of a portion of a scanner configured to include penetration light sources 1202, 1202' (e.g., penetrative spectral range light) and cameras that may be used as part of an intraoral scanner wand. In FIG. 12, a camera 1200 is shown that is flanked by a pair of LEDs 1202, 1202' for emitting light in the penetrative spectral range in substantially the same direction as the camera towards a target T (such as a tooth 1201). A single light source 1202 (e.g., LED) may be used instead of a pair. In general according to this disclosure, the light sources of the wand are projected in substantially the same direction as the camera, but in some embodiments the light sources can vary +/−15 degrees from the direction of the camera, as described above.

FIG. 13 shows a flowchart 1300 that describes one method for reconstructing a volumetric structure from an object having semi-transparent strongly scattering regions for a range of radiation wavelengths. The object having semi-transparent strongly scattering regions can be, for example, a tooth comprising an exterior enamel surface and an interior dentin surface.

At step 302 of flowchart 1300, the method comprises taking a plurality of images of the object with a camera in the range of radiation wavelengths, wherein lighting for the plurality of images is projected substantially from a direction of the camera. In some embodiments, the range of radiation wavelengths is an infrared or near infrared wavelength. The infrared or near infrared wavelength can be used, for example, to penetrate the semi-transparent object. In one embodiment, the lighting for the plurality of images can vary +/−15 degrees from the direction of the camera. The plurality of images can be stored in computer memory coupled to the camera.

Any of these methods may also include receiving location data representing a location of the camera relative to the object for each of the plurality of images. Generally, the location data includes the position and orientation of the camera with respect to the object. This location data can be determined from the plurality of images, or alternatively or additionally, the position and orientation can be measured with sensors 123 on the wand (e.g., gyroscope sensors, accelerometers, GPS, etc.). Alternatively or additionally, the position and orientation can be computed by registration of scanned surface data. In some embodiments, the location data comprises three numerical coordinates in a three-dimensional space (e.g., x, y, and z in a Cartesian coordinate system), and pitch, yaw, and roll of the camera. The location data can also be quantified as vector metrics (e.g., rotation metrics and vector position).

At step 306 of flowchart 1300, the method further comprises generating for each point in a volume an upper bound on a scattering coefficient from the plurality of images and the location data. Each of the plurality of images may be a projection from the real world (a 3D environment) onto a 2D plane (the image), during which process the depth is lost. Each 3D point corresponding to a specific image point may be constrained to be on the line of sight of the camera. The real world position of each 3D point can be found as the intersection of two or more projection rays through the process of triangulation.

In step 306, an upper bound on a scattering coefficient is determined for each point in a volume that represents the object being scanned. The upper bound is selected from the plurality of images for each point using the location data from the camera to triangulate the position of each point. The plurality of images produces an intensity for each point that is a result of the amount of light reflected by the object. This intensity for each point is used to generate the scattering coefficient for each point. The upper bound on the scattering coefficient for each point can be stored in memory coupled to the camera.

Generating, for each point in the volume an upper bound on the scattering coefficients may include projecting each point of a 3D grid of points corresponding to the volume of the object onto each of the plurality images using a first calibration, producing a list of scattering coefficient values for each projected point, correcting each scattering coefficient value on the list of scattering coefficient values according to a volume response, and storing a minimum scattering coefficient value for each grid point from the list of scattering coefficient values.

A number of calibrations can be performed to facilitate projecting each point of the 3D grid of points onto each of the plurality of images. For example, in one embodiment, the first calibration may comprise a fixed pattern noise calibration to calibrate for sensor issues and image ghosts of the camera. In another embodiment, the first calibration comprises a camera calibration that determines a transformation for the camera that projects known points in space to points on an image. In some embodiments, all of the calibrations described above can be performed prior to projecting the points onto the images.

When generating an upper bound on a scattering coefficient from the penetrative images and location data, the upper bound on the scattering coefficient(s) may only be determined for points within an exterior surface of the object being imaged. For example, the methods described herein can further include receiving surface data representing an exterior surface of the object (e.g., scan data representing an exterior or enamel surface of a tooth). With the exterior surface data, only points within this exterior surface (e.g., internal points) can be used to generate scattering coefficients. This may allow the imaging to focus only on, for example, a dentin surface within an enamel surface of teeth.

Finally, any of these methods may comprise generating an image of the object from the upper bound of scattering coefficients for each point 308. Example of generating these images are provided herein, and may include forming a line and/or surface based on threshold values of the scattering coefficients or values based on the scattering coefficients.

Figure 14:
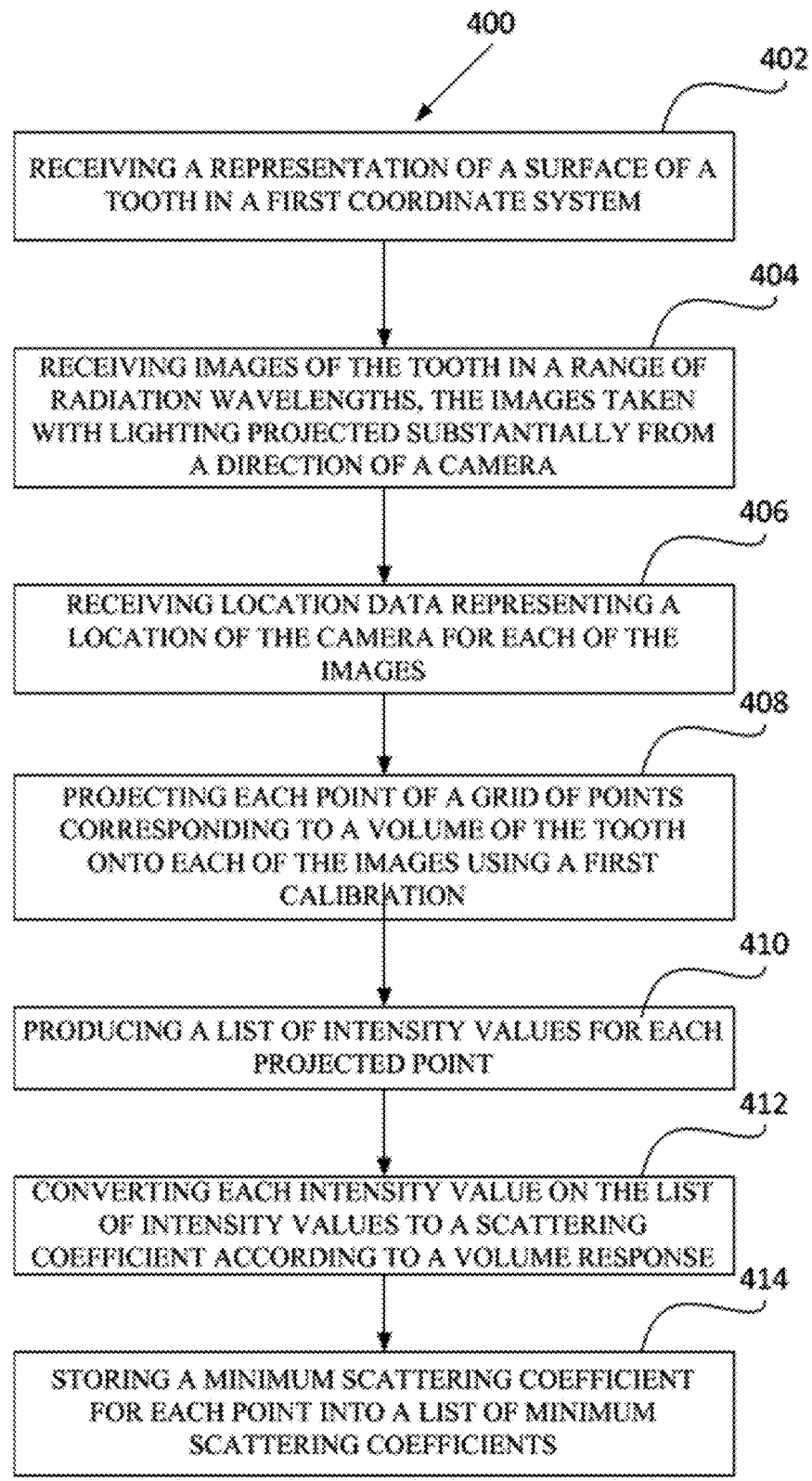
FIG. 14 illustrates another flowchart that provides method steps for reconstructing a volumetric structure from a tooth.

FIG. 14 is a flowchart 400 that illustrates a method for reconstructing a volumetric structure from a tooth. The tooth can be semi-transparent in a range of radiation wavelengths. At step 402, which is optional, the method comprises receiving, in a processor, a representation of a surface of the tooth in a first coordinate system. The representation of the surface of the tooth can be, for example, a 3D model of the tooth that is produced either by scanning the teeth or by taking a mold of the teeth.

The method may also include receiving, in the processor, a plurality of images of the tooth in the range of radiation wavelengths, the plurality of images taken with lighting projected substantially from a direction of a camera 404. In some embodiments, the wavelength is a penetrative wavelength of the infrared or near infrared region or a range within the IR/near IR. The infrared (IR) or near infrared wavelength can be used, for example, to penetrate the tooth. The lighting for the plurality of images can vary +/−15 degrees from the direction of the camera. The plurality of images can be stored in computer memory coupled to the camera.

At step 406 the method further comprises receiving, in the processor, location data representing a location of the camera for each of the plurality of images. Generally, the location data includes the position and orientation of the camera with respect to the object. This location data can be determined from the plurality of images, or alternatively, the position and orientation can be measured with sensors on the camera (e.g., gyroscope sensors, accelerometers, GPS, etc.). Alternatively or additionally, the position and orientation can be computed by registration of scanned surface data. In some embodiments, the location data comprises three numerical coordinates in a three-dimensional space (e.g., x, y, and z in a Cartesian coordinate system), and pitch, yaw, and roll of the camera. The location data can also be quantified as vector metrics (e.g., rotation metrics and vector position).

The method may also include projecting each point of a grid of points corresponding to a volume within the surface of the tooth onto each of the plurality images using a first calibration 408. The grid of points that is produced may be inside of the exterior surface of the tooth. The grid can sit on a cubic grid, for example. Each grid point can be projected onto each of the plurality of images using a calibration. A number of calibrations can be performed to facilitate projecting each point of the grid onto each of the plurality of images. For example, the calibration may comprise a fixed pattern noise calibration to calibrate for sensor issues and image ghosts of the camera. In another embodiment, the calibration may comprise a camera calibration that determines a transformation for the camera that projects known points in space to points on an image. In some embodiments, all of the calibrations described above can be performed prior to projecting the points onto the images.

The method may further include producing a list of intensity values for each projected point 410. The plurality of images produces an intensity for each point that is a result of the amount of light reflected by the object. This intensity value for each point may be stored.

At step 412 the method may further comprise converting each intensity value on the list of intensity values to a scattering coefficient according to a volume response. This step may be performed to calibrate the intensity value for each pixel. The process calculates a scattering coefficient that would produce such an intensity value for each point relative to the position of the camera. The output is a scattering coefficient which normalizes the intensity according to a volume response.

Finally, in FIG. 14, the method may further include storing a minimum scattering coefficient for each point into a list of minimum scattering coefficients 414. The method may further comprise producing an image from the list of minimum scattering coefficient for each point.

Figure 15A:
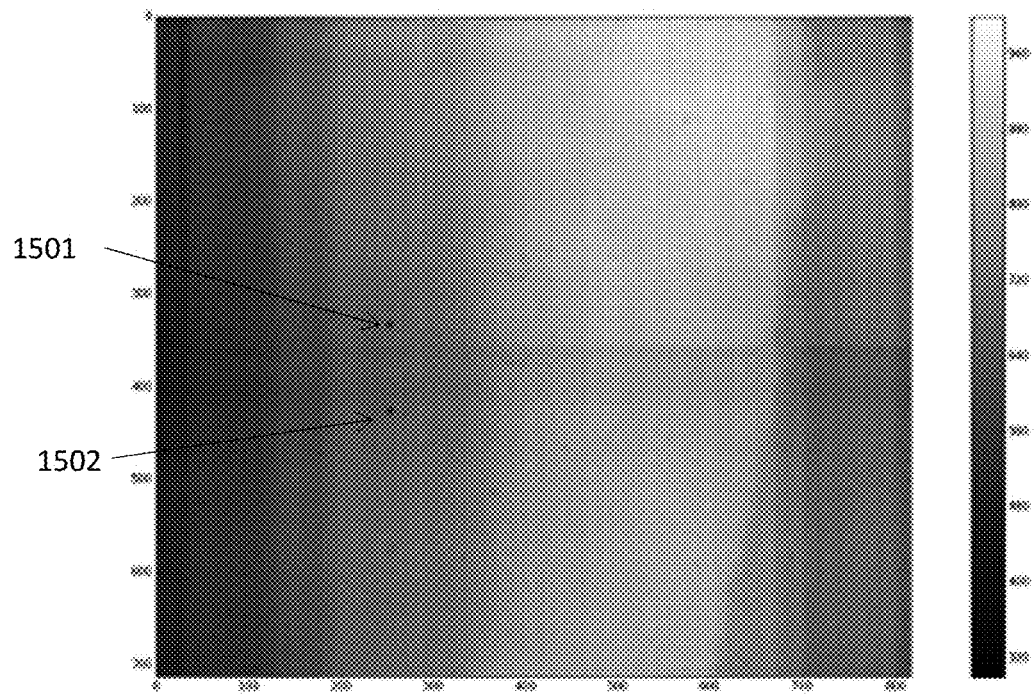
FIGS. 15A-15E show one example of an image fixed pattern noise calibration and illumination non-uniformity calibration, which gives a constant response for a uniform plane target.
Figure 15B:
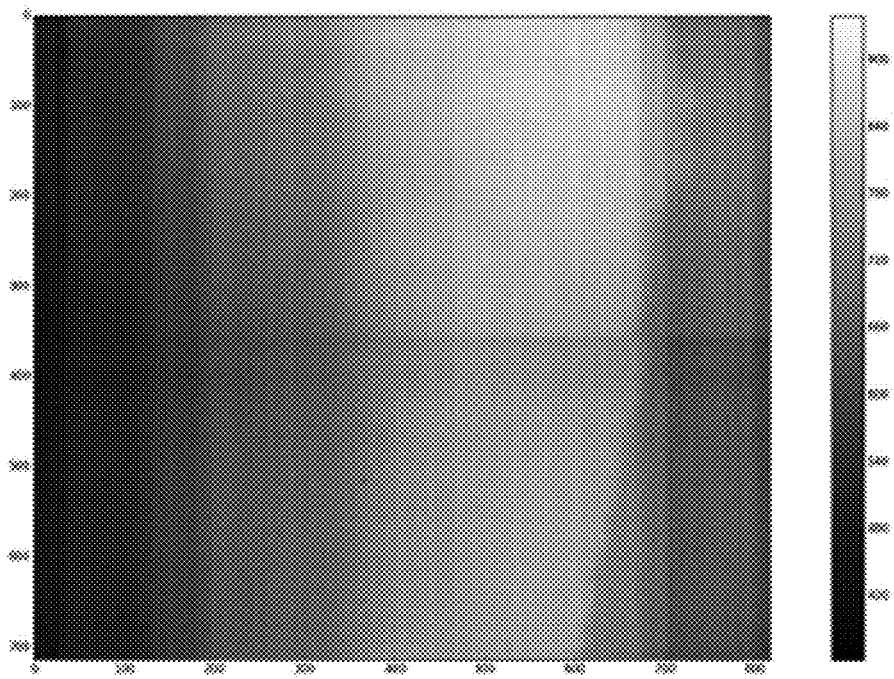
Figure 15C:
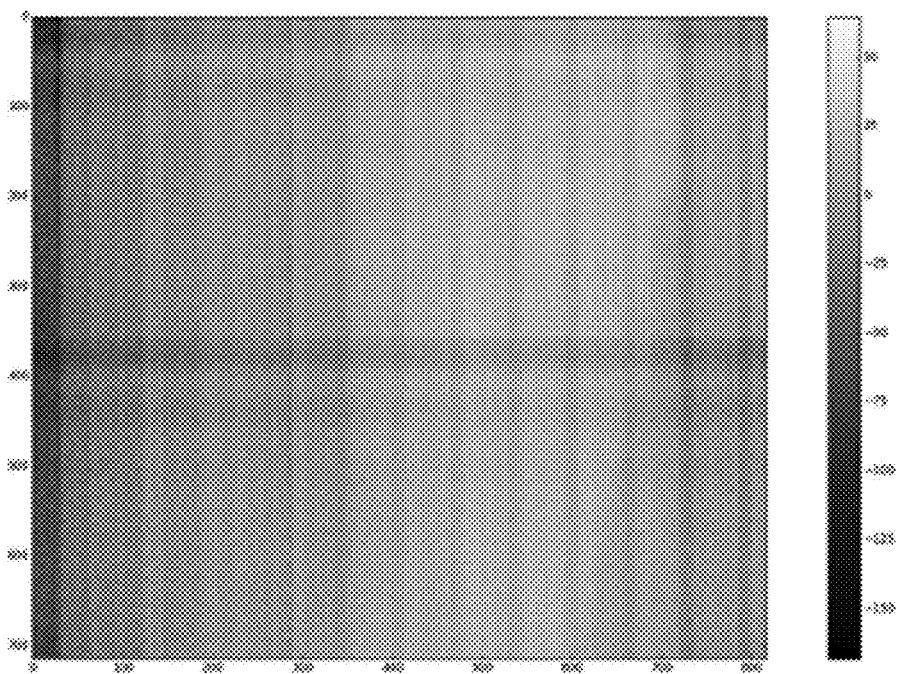
Figure 15D:
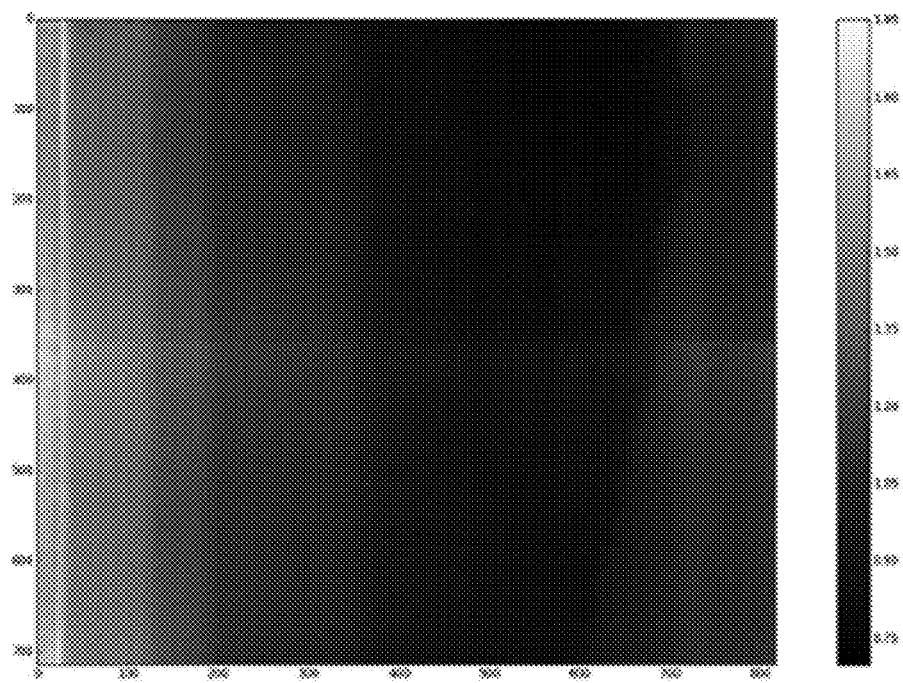
Figure 15E:
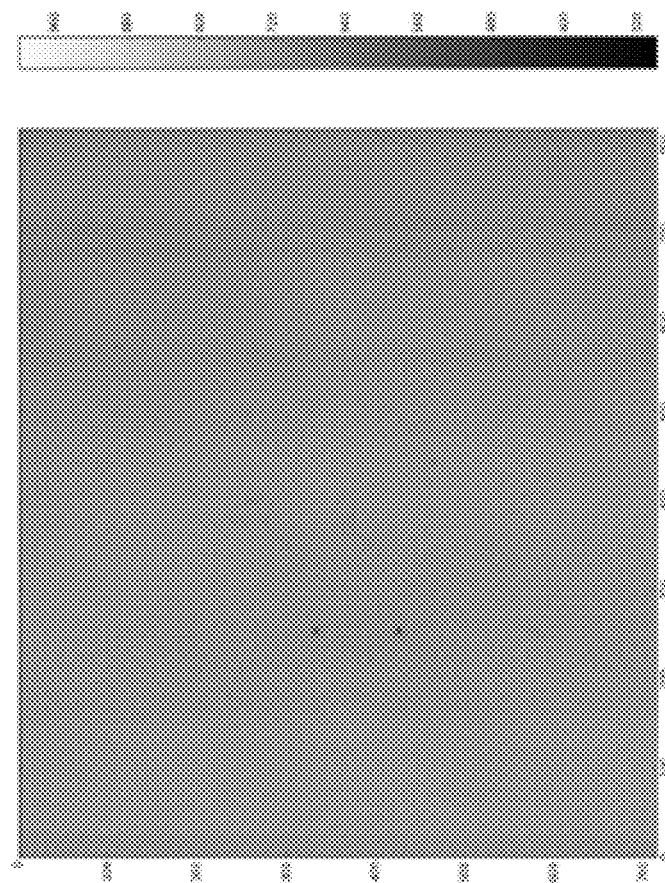

As described above, the methods and techniques can include a plurality of calibrations to project points from the real world into the plurality of images. One such calibration is an image fixed pattern noise calibration (PRNU) which addresses sensor issues and system ghosts that do not depend on the object being scanned. FIGS. 15A-E show one example of an image fixed pattern noise calibration, which gives a constant response for a uniform plane target. FIG. 15A shows an original image of a plane uniform target, including two particles 1501, 1502 in the middle of the image. FIG. 15B shows the median image after moving the target parallel to the plane. This causes the two particles to "disappear" from the image. FIG. 15C shows the image after applying a bias coefficient figure for each pixel, which creates strong electronic noise in the image. In FIG. 15D, a slope has been applied to each pixel, resulting in a smooth pattern given by the optics. Finally, FIG. 15E shows the final image after response equalization.

Another calibration that may be applied is called a camera calibration, which allows the projection of real world (3D) points to 2D image pixels. The camera calibration determines a transformation for the camera that projects known points in space to points on an image.

A volumetric response calibration that gives a scattering coefficient for all points in the world given an intensity in the image within a field of view of the camera may also be applied. This calibration brings a standard scattering coefficient to constant response anywhere in the field of view.

Finally, a scan to world camera calibration may be applied that is a rigid body transformation that converts from the scan coordinate system (of the 3D scan of the object) to the camera calibration coordinate system (of the 2D images of the object).

Other techniques may be used to determine the volumetric scattering coefficients from the penetrative images and camera positions. For example in some variations, back propagation may be used. Back propagation may include estimating (e.g., tracing) rays going through the tooth volume and entering the camera. The actual intensities reaching the sensor for each ray may be taken from the penetrative images and camera positions and orientations. For each ray the damping of the intensity due to scattering in the volume it passes may be estimated. For example, the transmission of light through a strongly scattering and weakly absorbing material may be modeled using a hybrid calculation scheme of scattering by the Monte Carlo method to obtain the temporal variation of transmittance of the light through the material. A set of projection data may be estimated by temporally extrapolating the difference in the optical density between the absorbing object and a non-absorbing reference to the shortest time of flight. This technique may therefore give a difference in absorption coefficients. For example, see Yamada et al., "Simulation of fan-beam-type optical computed-tomography imaging of strongly scattering and weakly absorbing media," Appl. Opt. 32, 4808-4814 (1993). The volumetric scattering may then be estimated by solving for the actual intensities reaching the sensor.

Figure 16:
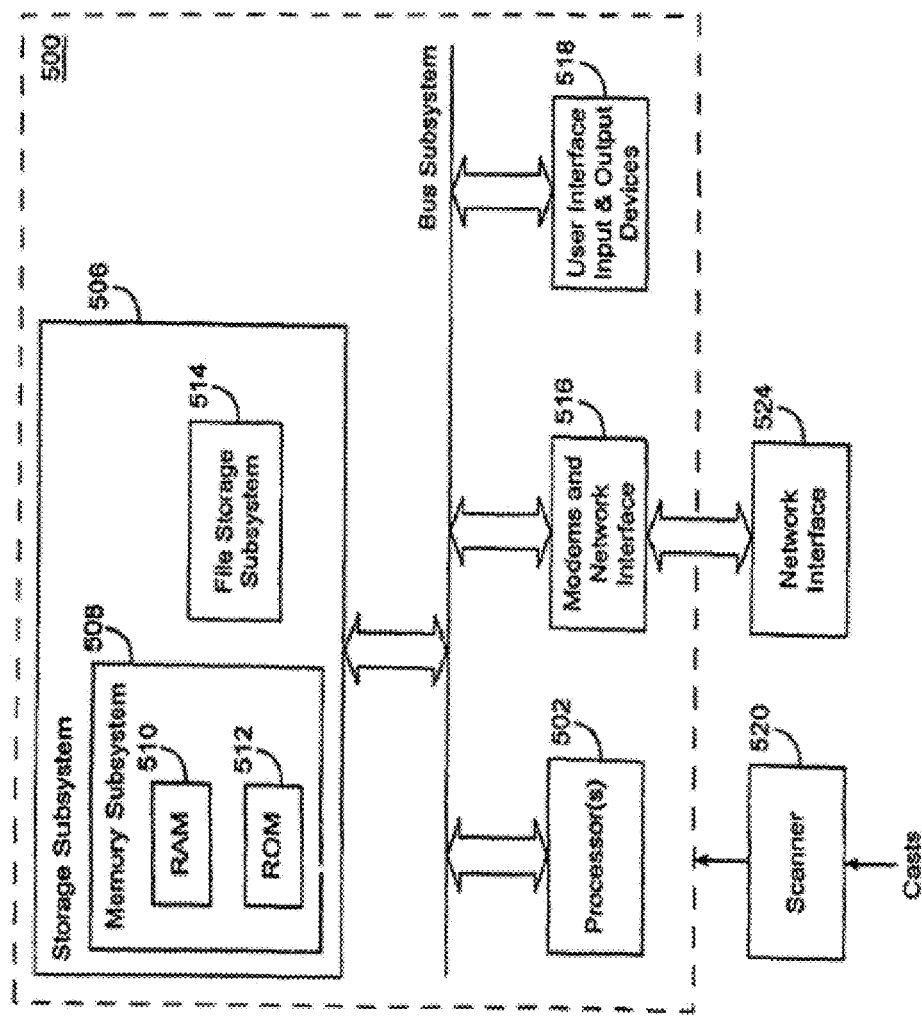
FIG. 16 is a simplified block diagram of a data processing system which can be used to perform the methods and techniques described herein.

Any of the methods described herein may be performed by an apparatus including a data processing system (or subsystem), which may include hardware, software, and/or firmware for performing many of these steps described above, including as part of a processor of an intraoral scanner (see, e.g., FIG. 1B). For example, FIG. 16 is a simplified block diagram of a data processing sub-system 500. Data processing system 500 typically includes at least one processor 502 which communicates with a number of peripheral devices over bus subsystem 504. These peripheral devices typically include a storage subsystem 506 (memory subsystem 508 and file storage subsystem 514), a set of user interface input and output devices 518, and an interface to outside networks 516, including the public switched telephone network. This interface is shown schematically as "Modems and Network Interface" block 516, and is coupled to corresponding interface devices in other data processing systems over communication network interface 524. Data processing system 500 may include a terminal or a low-end personal computer or a high-end personal computer, workstation or mainframe.

The user interface input devices may include a keyboard and may further include a pointing device and a scanner. The pointing device may be an indirect pointing device such as a mouse, trackball, touchpad, or graphics tablet, or a direct pointing device such as a touchscreen incorporated into the display. Other types of user interface input devices, such as voice recognition systems, may be used.

User interface output devices may include a printer and a display subsystem, which includes a display controller and a display device coupled to the controller. The display device may be a cathode ray tube (CRT), a flat-panel device such as a liquid crystal display (LCD), or a projection device. The display subsystem may also provide nonvisual display such as audio output.

Storage subsystem 506 may maintain the basic programming and data constructs that provide the functionality of the present invention. The methods described herein may be configured as software, firmware and/or hardware, and (of software/firmware) may be stored in storage subsystem 506. Storage subsystem 506 typically comprises memory subsystem 508 and file storage subsystem 514.

Memory subsystem 508 typically includes a number of memories including a main random access memory (RAM) 510 for storage of instructions and data during program execution and a read only memory (ROM) 512 in which fixed instructions are stored. In the case of Macintosh-compatible personal computers the ROM would include portions of the operating system; in the case of IBM-compatible personal computers, this would include the BIOS (basic input/output system).

File storage subsystem 514 may provide persistent (non-volatile) storage for program and data files, and may include at least one hard disk drive and at least one floppy disk drive (with associated removable media). There may also be other devices such as a CD-ROM drive and optical drives (all with their associated removable media). Additionally, the system may include drives of the type with removable media cartridges. One or more of the drives may be located at a remote location, such as in a server on a local area network or at a site on the Internet's World Wide Web.

In this context, the term "bus subsystem" may be used generically so as to include any mechanism for letting the various components and subsystems communicate with each other as intended. With the exception of the input devices and the display, the other components need not be at the same physical location. Thus, for example, portions of the file storage system could be connected over various local-area or wide-area network media, including telephone lines. Similarly, the input devices and display need not be at the same location as the processor, although it is anticipated that the present invention will most often be implemented in the context of PCS and workstations.

Bus subsystem 504 is shown schematically as a single bus, but a typical system has a number of buses such as a local bus and one or more expansion buses (e.g., ADB, SCSI, ISA, EISA, MCA, NuBus, or PCI), as well as serial and parallel ports. Network connections are usually established through a device such as a network adapter on one of these expansion buses or a modem on a serial port. The client computer may be a desktop system or a portable system.

Scanner 520 may correspond to the wand and other components responsible for scanning casts of the patient's teeth obtained either from the patient or from an orthodontist and providing the scanned digital data set information to data processing system 500 for further processing. In a distributed environment, scanner 520 may be located at a remote location and communicate scanned digital data set information to data processing system 500 over network interface 524.

Various alternatives, modifications, and equivalents may be used in lieu of the above components. Additionally, the techniques described here may be implemented in hardware or software, or a combination of the two. The techniques may be implemented in computer programs executing on programmable computers that each includes a processor, a storage medium readable by the processor (including volatile and nonvolatile memory and/or storage elements), and suitable input and output devices. Program code is applied to data entered using an input device to perform the functions described and to generate output information. The output information is applied to one or more output devices. Each program can be implemented in a high level procedural or object-oriented programming language to operate in conjunction with a computer system. However, the programs can be implemented in assembly or machine language, if desired. In any case, the language may be a compiled or interpreted language. Each such computer program can be stored on a storage medium or device (e.g., CD-ROM, hard disk or magnetic diskette) that is readable by a general or special purpose programmable computer for configuring and operating the computer when the storage medium or device is read by the computer to perform the procedures described. The system also may be implemented as a computer-readable storage medium, configured with a computer program, where the storage medium so configured causes a computer to operate in a specific and predefined manner.

Figure 26A:
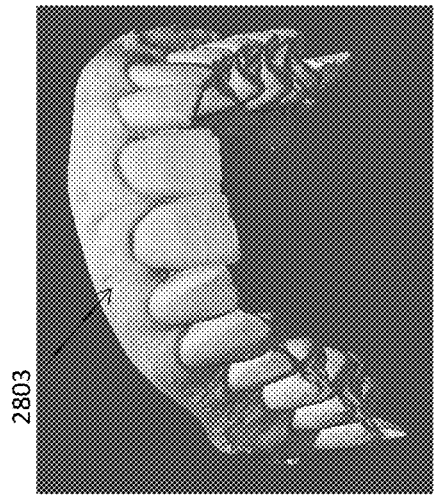
FIGS. 26A-26C illustrate a method of forming a 3D surface that may be used to generate a volumetric model (showing both surface and internal structures) of a patient's teeth.
Figure 26B:
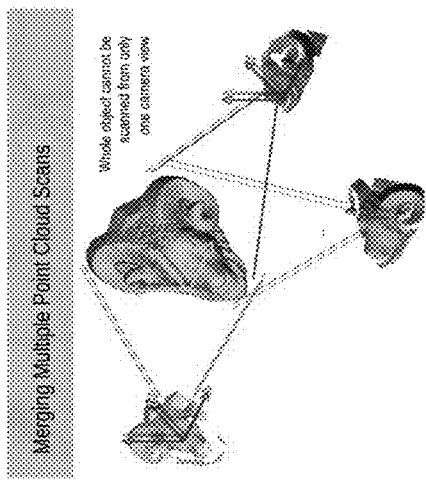
Figure 26C:
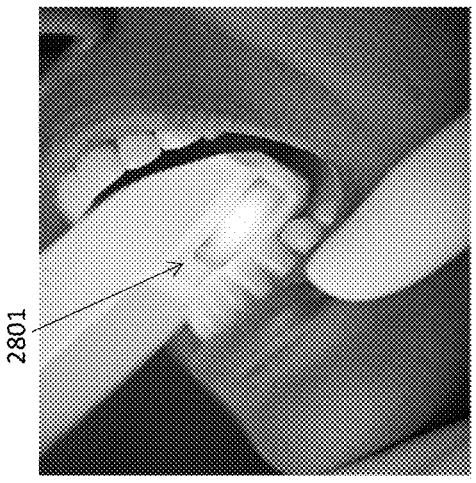

FIGS. 26A-26C and 27A-27G illustrate steps that may form part of a method of forming a 3D volumetric model of a patient's teeth and may be used for one or more treatments using the methods and apparatuses described above. In any of these methods, an intraoral scanner 2801 capable of measuring both surface (including, in some variations color, e.g., R-G-B color) and internal structures may be used to scan the patient's teeth (e.g., taking images and scans of the jaw, including the teeth). The apparatus may scan in different modalities, including surface (non-penetrative or not substantially penetrating, e.g., visible light, white light) and penetrative (e.g., near IR/IR) wavelengths. Scanning typically includes scanning from multiple positions around the oral cavity and assembling the resulting images into a three-dimensional model of the teeth, e.g., by solving the relative position of the scans relative to the jaw (FIG. 26C). The surface scanning may be used to construct a model (e.g., a 3D digital model, and/or renderings) of the outer surface of the jaw/teeth 2803, as shown in FIG. 26C.

Figure 27A:
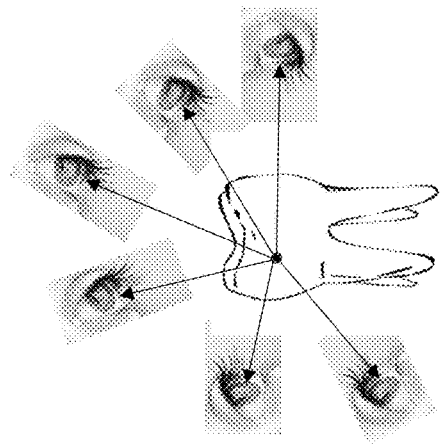
FIGS. 27A-27G illustrate a method of generating a volumetric model of a patient's teeth using near-IR scanning in addition to surface scanning.
Figure 27B:
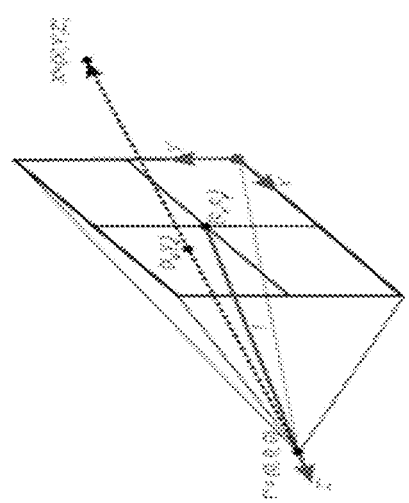
Figure 27C:
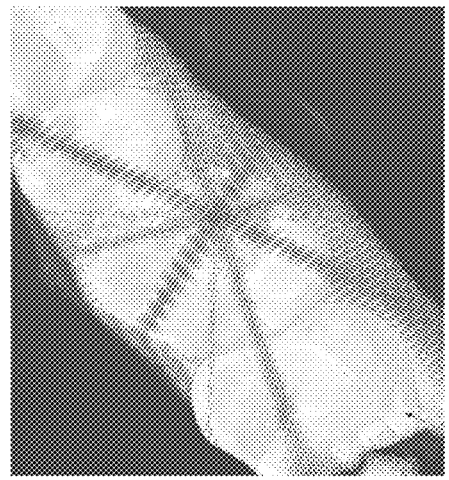
Figure 27E:
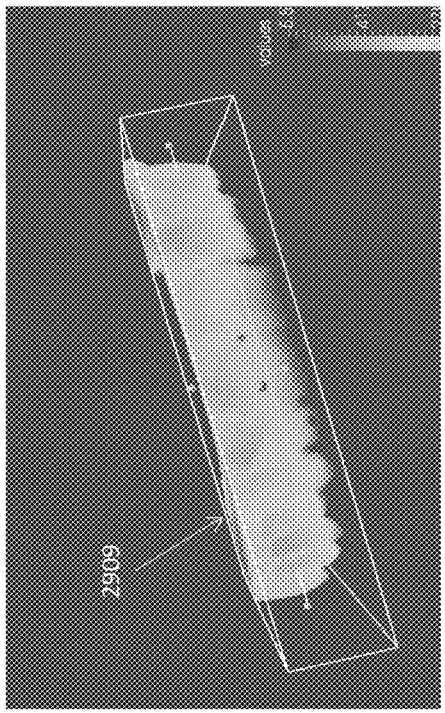
Figure 27F:
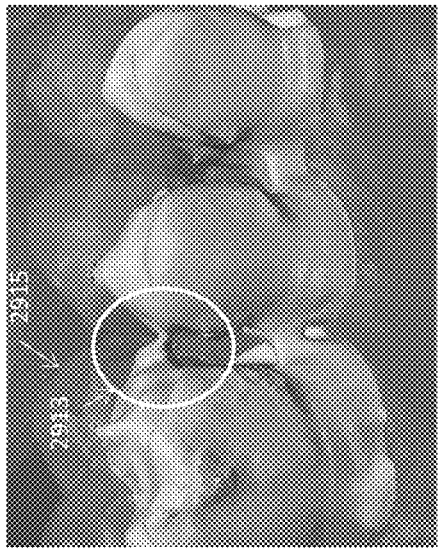
Figure 27D:
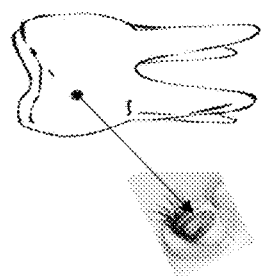
Figure 27G:
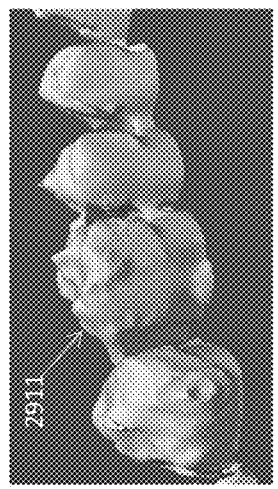

In any of these methods and apparatuses described herein, internal structures within the teeth may be formed or modeled to form a volumetric model of the teeth including the internal structures that are extracted from the penetrative scans (e.g., near-IR and/or IR scans), as illustrated in FIGS. 27A-27G. FIGS. 26A-27G describe one method of reconstructing internal structures by using scattering coefficients (other methods may be used alternatively or additionally). In FIG. 27A, a grid is constructed of points representing the inner volume of the jaw/teeth. All of the grid points are projected onto the penetrative (e.g., near-IR) images taken, and all pixel positions may be saved for each of the grid points, as shown in FIG. 27B. For each pixel position and grid position, the apparatus may calculate the scattering coefficient which would result in the gray level of pixel observed, as graphically illustrated in FIG. 27C. In the figures (e.g., FIG. 27C), the eye may represent the viewing angle of the sensor (e.g., camera). For each grid point, the apparatus may take the minimal scattering coefficient that is calculated (FIG. 27D). The grid of points with corresponding minimal scattering coefficients may then provide a volume 2909 that may be sampled at the grid points based on thresholds or correlations (e.g., iso-surfaces) of minimal scattering values, as shown in FIG. 27E. FIG. 27G shows an iso-surface 2911 created by identifying a constant value of the density function sampled. FIG. 27F is an enlarged view of the same region of the teeth, showing both the iso-surface from FIG. 27G as well as a ghosted image (partially transparent) of the enamel 2915 around the iso-surface. This iso-surface may represent dentin and (as described below) dental caries extending from the outer surface of the tooth toward the dentin.

In the example shown in FIG. 27F, the iso-surface shows the dentin-enamel transition 2911 visible beneath the enamel 2915. The example in FIG. 27F also indicates a dental caries shown in circled region 2913. In this example, the dental caries (similar to the dentin) appears as an iso-surface within or surrounded by the enamel. The dental caries may be distinguished because it extends from the inner, dentin region to an outer surface of the tooth. Since the methods and apparatuses described herein may accurately reconstruct both the outer surface and the inner structures, this characteristic configuration (showing an arm or extension extending from the outer surface through the IR/near-IR transparent enamel) may be used to identify dental caries. In FIG. 27F a likely dental caries region is circled 2913, showing an extension or bridge between two teeth in a region where the surface scan shows that the teeth are actually separate. Thus, combining the surface scan with the internal scanning (e.g., from the IR/near-IR images) may allow for corrections in the internal data due to errors that may occur because of the limited view angles or the like. Any of the apparatuses and methods described herein may be configured to automatically or semi-automatically identify these regions or irregularities corresponding to dental caries and the like. They may be highlighted in the model, image or representation of the teeth, and/or a flag, alert or other notification, along with a putative location, may be presented, transmitted and/or stored. Alternatively or additionally, the threshold(s) used to determine the iso-surfaces may be chosen to distinguish between the one or more internal features such as the dentin, caries, fillings, cracks, etc.

Alternatively or additionally, the apparatus may automatically (or semi-automatically) determine and distinguish internal structures within the teeth based on the shape of the iso-surfaces and/or their relative position(s) within the teeth. As mentioned above, caries may have a similar densities (e.g., scattering coefficients) compared to dentin. However, the morphology of the caries may distinguish them from dentin. The apparatus may detect 'arms' or appendages of material having a density (e.g., scattering coefficients) similar to that for dentin, but extending from the out surface of the enamel. Since the outer surface of the teeth may be well characterized in addition to the internal structures, the extent of a caries may be determined by mapping the outer surface of the iso-density map for regions extending from the outer surface toward a larger, defined internal dentin pattern. The border between the dentin and the internal extent of the caries may be determined by approximating the continuous surface of the dentin, including the region around the "projecting" region and/or looking at the rate of change of direction of the surface of the dentin. Other internal structures, such as fillings, cracks and the like may be distinguished based on their scattering coefficient value ranges, and/or based on their position or morphology. The apparatus may display them in different colors, annotations, etc.

Thus, in any of these methods and apparatuses, the scanner may see inside the enamel and reconstruct the margin line. In addition, the use of additional wavelengths (e.g., green light) or even different radiation modalities (e.g., ultrasound) imaging through the flesh may be possible, allowing construction of margin lines and even teeth roots, and/or helping to distinguish structures such as dental caries from the dentin or other internal structures.

The resulting volumetric 3D model of the teeth may be used to reconstruct teeth base on the histological teeth. As described, the volumetric model may be used to create dental prosthetics (implants, etc.) that have a more realistic appearance and/or a better fit.

Figure 28B:
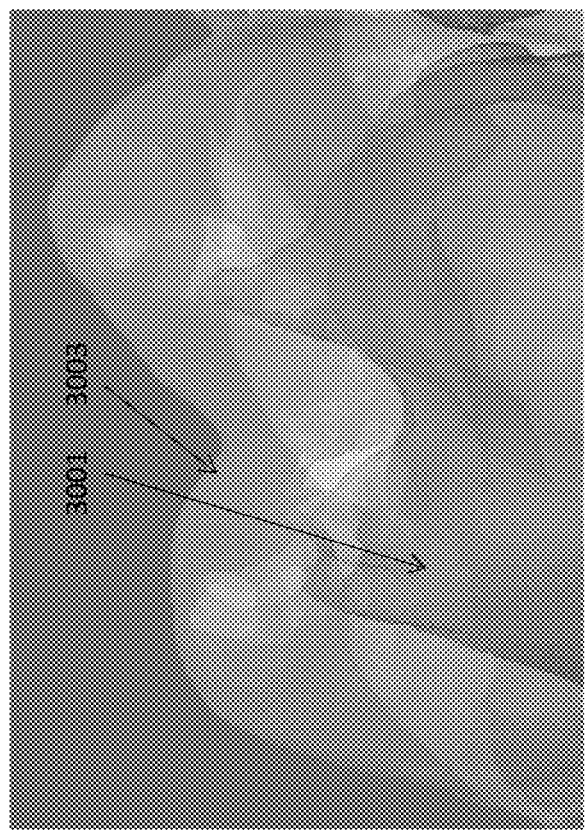
FIGS. 28A and 28B illustrate volumetric models of a patient's teeth formed using an intraoral scanner, showing both surface features, e.g., enamel, and internal (segmented) features, e.g., dentin.
Figure 28A:
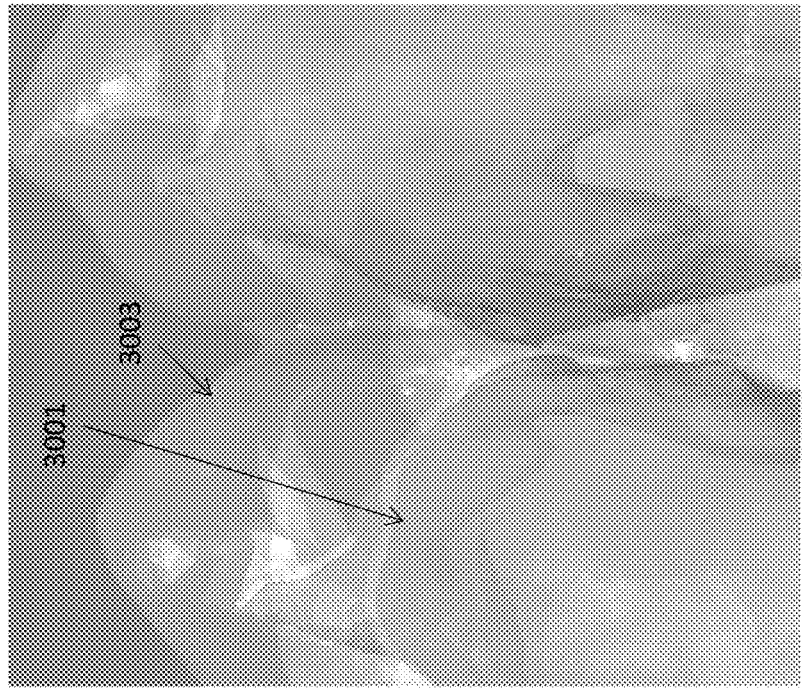

Further, the methods and apparatuses described herein may permit a user (e.g., dentist, physician, dental technician, etc.) to follow the teeth over time, including tracking dentin, caries, etc., and general dental health by comparing models taken over time. For example, time-lapse videos (images) may be constructed. FIG. 28A shows an example of a volumetric reconstruction taken at a first time, showing the dentin 3001 (solid) and enamel 3003 (made slightly transparent). FIG. 28B show another example of a volumetric model of teeth showing the dentin 3001 and enamel 3003.

The volumetric model may include width information may provide estimates of wear over time as well. For example, changes in the enamel width over time and over different regions of the teeth may be easily tracked. By knowing the enamel width we can estimate the tooth wear and provide a snap shot of the severity of wear.

Segmentation and Classification

Any appropriate method and/or apparatus (e.g., systems, devices, software, etc.) for generating images of internal structures from within a tooth (or other semi-transparent, strongly scattering object) may be used. For example, alternatively or additionally to the use of scattering coefficients as discussed above, any of the apparatuses and methods described herein may use the two-dimensional penetrative images along with position and/or orientation information about the intraoral scanner relative to the object being imaged (e.g., the teeth) to segment the two-dimensional penetrative images and form a three-dimensional model of the teeth including one or more internal structures within the object. A penetrative image may refer to images taken with a near-IR and/or IR wavelength, revealing internal structures within the object (e.g., tooth). The position and/or orientation of the scanner may be a proxy for the position and/or orientation of the camera taking the images which is on the scanner (e.g., on a handheld wand).

The apparatuses and methods described herein may construct a three-dimensional (3D) volumetric model of the teeth from segmented two-dimensional (2D) images. These methods and apparatuses may also segment the 3D model of the teeth.

In general, the methods and apparatuses described herein allow for the direct segmentation of the penetrative images. This may allow for the identification of dentin within the teeth, including the location and morphology of the dentin, as well as the identification and location of cracks, lesions, and/or caries in the teeth, including in the dentin. The use of segmentation may allow for reconstruction of a volumetric model based on the penetrative images and the knowledge of the camera position corresponding to the penetrative images. A volumetric model of teeth can be segmented and these segments (relating to different internal structures of the tooth) may be projected back to the images and/or combined with a surface model of the teeth (e.g., the outer tooth surface), allowing projections onto the surface images and better segmentation of the inner structures of teeth.

Thus, penetrative images taken through the teeth with a penetrative wavelength (e.g., near IR and/or IR), may include inner teeth structures and/or 3D data. These images may be taken using any of the dental scanners described herein, and the teeth volume may be segmented into different regions according to opacity, color, and other properties of the images and 3D data. These regions can be for example: healthy enamel, dentin, lesion, dental filling(s), etc. The segmentation can be done on 2D images or on volumetric models. The segmentation can be used to classify the images and/or the 3D models according to the presence of different segments. A user may be able to detect by this segmentation manually or automatically (or semi-automatically) to classify different internal structures, such as: dental caries, enamel erosion, and other dental issues. Further, the images or models may be used to measure internal regions of a tooth or multiple teeth segments for better dental treatments, including aligning teeth or other treatment planning. For example, a user may be able to locate dental lesion in an accurate fashion to plan accurate filling with minimal enamel extraction. Thus, the use of segmentation as described herein may permit the capture of inner teeth structure without ionizing radiation, as is currently used with X-rays. Dental issues may be presented on 3D volumetric model. Further, as will be described in detail below, segmentation and classification of internal structures may be automatized. Finally, exact measurements of internal structures may be taken for better treatment planning.

Figure 17:
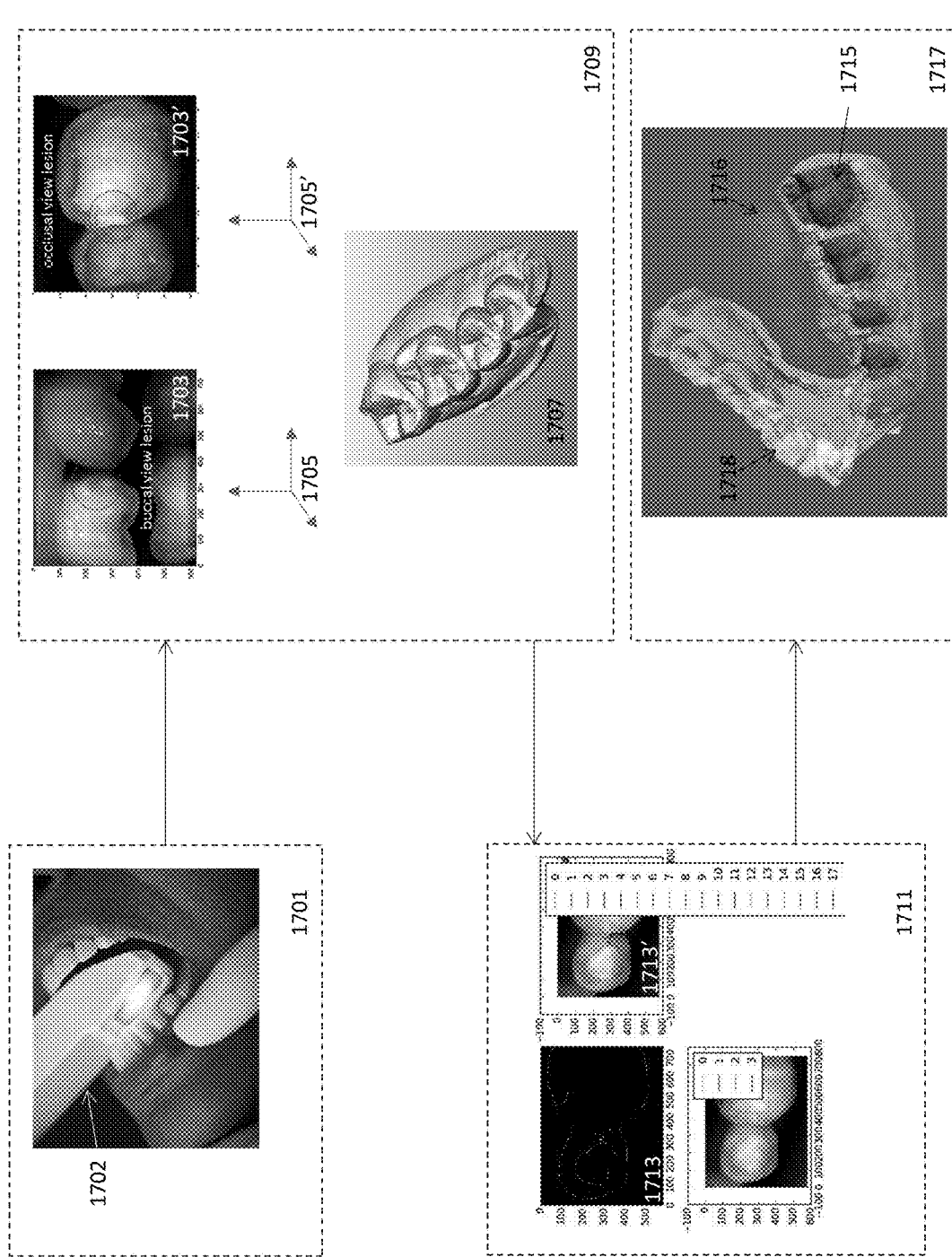
FIG. 17 is an example of a method of scanning teeth with an intraoral scanner to identify internal structures using a penetrative wavelength (e.g., IR and/or near-IR).

FIG. 17 illustrates an example of a data flow for scanning teeth with an intraoral scanner to identify internal structures. In FIG. 17, the method shown includes three parts. First, the teeth may be scanned with an intraoral scanner 1701 (or any other scanner) configured to provide penetrative scans into the teeth using an optical (e.g., IR, near IR, etc.) wavelength or range of wavelengths. Any of these scanners may also concurrently scan to determine a surface features (e.g., via one or more non-penetrative wavelengths), color, etc., as described above. During scanning, a plurality of penetrative scans 1703, 1703' are taken, and the position of the camera 1705, 1705' (e.g., x,y,z position and/or pitch, roll, yaw angles) may be determined and/or recorded for each penetrative image. In some variations, the surface of the teeth may also and concurrently be imaged, and a 3D surface model of the teeth 1707 determined, as described above. In this example, the patient's teeth may be scanned, for example, with an intraoral 3D scanner 1702 that is capable of imaging the inner teeth structure using, for example, near infra-red imaging. The location and orientation of the camera may be determined, in part, from the 3D scanning data and/or the 3D teeth surface model 1707.

Thereafter, the penetrative images may be segmented 1711. In this example, segmentation may be done in one of two ways. On the inner teeth structure images, the images may be segmented using contour finding 1713, 1713'. Machine learning methods may be applied to further automate this process. Alternatively or additionally, near images (where their camera position is close) may be used to decide on close features, and also project features from the 3D model back to the images in order to locate correctly segments like enamel. The method may also include projecting pixels from the inner teeth images back to the teeth and calculating a density map of inner teeth reflection coefficient. Enclosing surfaces of different segments may be found or estimated by using iso-surfaces or thresholds of the density map and/or by machine learning methods. In addition, segmenting the images and projecting the segments back to a model (such as the 3D surface model, e.g., projecting back to the world), may be used to find a segment by the intersection of the segment projections and the teeth surface.

The results may be displayed 1717, transmitted and/or stored. For example, the results may be displayed by the scanning system during the intraoral scanning procedure. The results may be shown by images with enclosing contours for different segments, a 3D density map, etc. In the example shown in FIG. 17 a density map 1715, representing the dentin beneath the enamel on the outer surface, is shown. This image may be color coded to show different segments. In this example, internal segments (structures) are shown within the 3D surface model (which is shown transparent); not all teeth have been scanned with penetrative images, thus, only some are shown. Alternative views, sections, slices, projections or the like may be provided. In FIG. 17, the example image includes artifacts that are present outside of the teeth 1716; these may be removed or trimmed, based on the surface model 1718.

A segment may mark each pixel on the image. Internal structures, such as dentin, enamel, cracks, lesions, etc. may be automatically determined by segmentation, and may be identified manually or automatically (e.g., based on machine learning of the 3D structure, etc.). Segments may be displayed separately or together (e.g., in different colors, densities, etc.) with or without the surface model (e.g., the 3D surface model).

Thus, in FIG. 17, the patient is initially scanned with a 3D scanner capable of both surface scanning and penetrative scanning (e.g., near IR imaging), and the orientation and/or position of the camera is known (based on the position and/or orientation of the wand and/or the surface scans). This position and orientation may be relative to the tooth surface. The method and apparatus may therefore have an estimate of the camera position (where it is located, e.g., x,y,z position of the camera, and its rotational position).

Figures 22A, 22B, 22C:
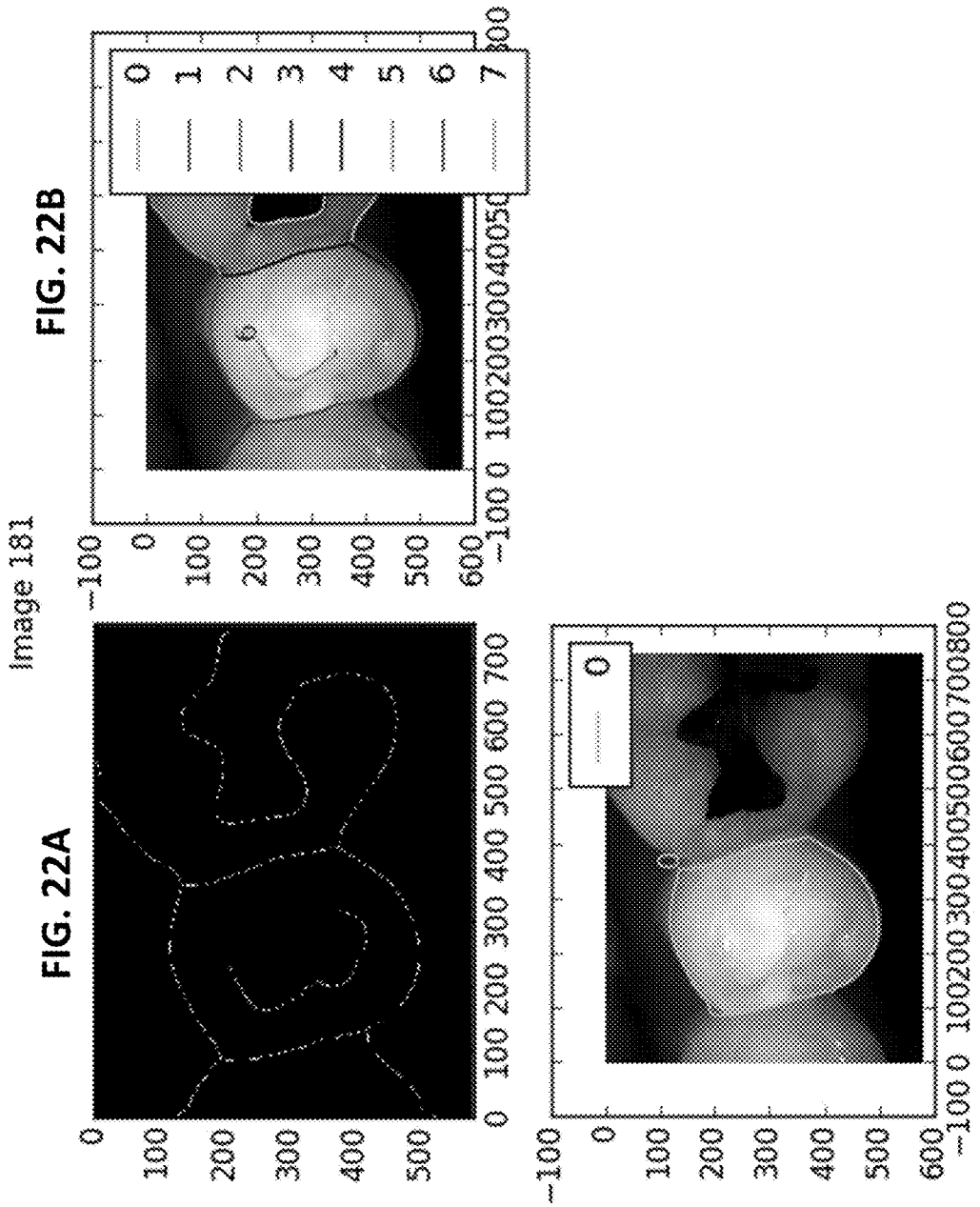
FIGS. 22A-22C illustrate segmentation of a near-IR image of a patient's teeth.
Figure 23B:
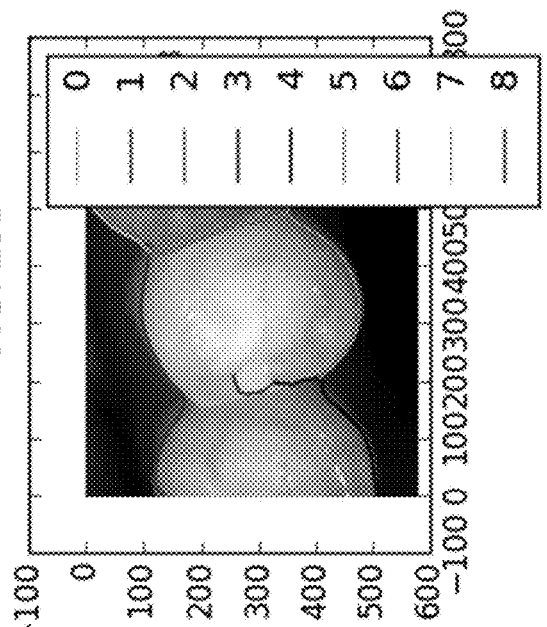
FIGS. 23A-23C illustrate segmentation of a near-IR image of a patient's teeth.
Figure 23A:
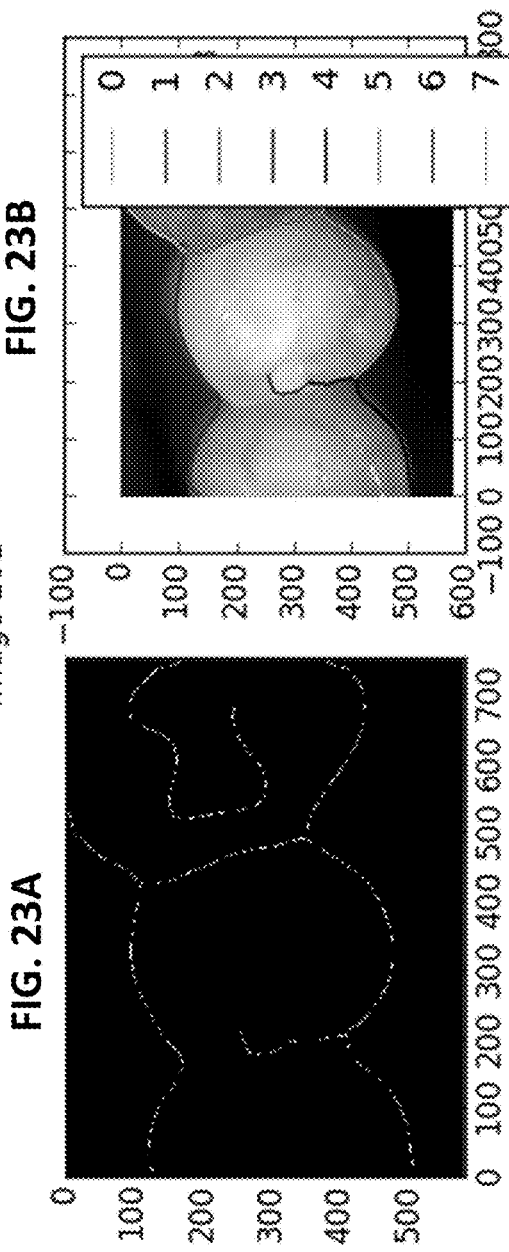
Figure 23C:
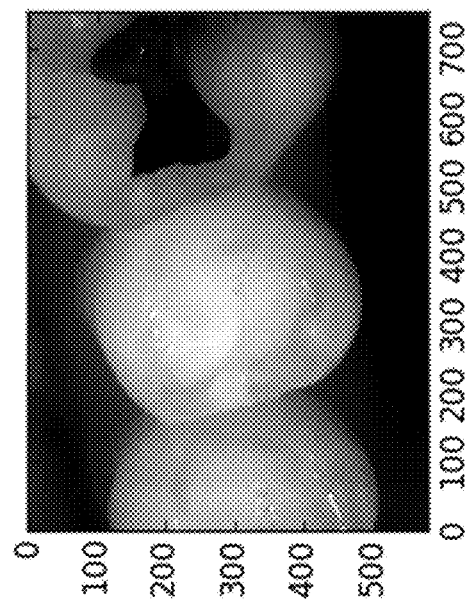

In general, penetrative images (e.g., near IR or IR images) may be segmented automatically. FIGS. 18A-18C illustrate a first example of automatic segmentation of a near-IR image. FIG. 18A, shows a first automatic segmentation of the outer surface of the teeth, determined by, e.g., edge detection. In FIG. 18A, the edges 1803 of the outer perimeter are shown. In this example, only a first level of edge detection was performed, looking for the outer perimeter. In FIGS. 18B and 18C, a continuous edge region 1805 is shown, derived from the edge detection, and mapped onto the near-IR image (original image). FIGS. 19A-19C show the identification and mapping of other edges from the same image. FIG. 19A shows just the edges detected using a threshold setting value from the near-IR image (e.g., FIG. 19C). In FIG. 19B five (overlapping 1905) segments, 0-4, are traced from the detected edges by forming continuous lines. The different segments are shown color coded, and a color key identifying the segments is shown on the right. From the near-IR images the apparatus can automatically segment the images. In FIGS. 18A-18C and 19A-19C, the different segments are marked and may correspond to different regions (or different internal structures) on image. When multiple images are analyzed, these putative segments may be re-projected back to a 3D model and/or shown in the images. FIGS. 20A-20C and 21A-21C illustrate other examples of near-IR images from the same patient shown in FIGS. 18A-19C, illustrating segmentation based on edge detection and identification of presumptive continuous line regions from the detected edges. In FIG. 21A-21C, another region of the teeth from the same patient are shown; eight segments (0-7) have been identified in this image, as shown in FIG. 21B. FIG. 21A shows the edge detection of the original image, shown in FIG. 21C. FIGS. 22A-22C illustrate segmentation of another region of the patient's teeth. FIG. 22A shows the detected edges from the original near-IR image. FIGS. 22B and 22C show eight segments (0-7) identified on the near-IR image. Similarly, FIGS. 23A-23C illustrate segmentation of another region of the patient's teeth; FIG. 23A shows the detection of edges, FIG. 23B shows segments identified from these edges, and FIG. 23C shows the original near-IR image.

Figure 24A:
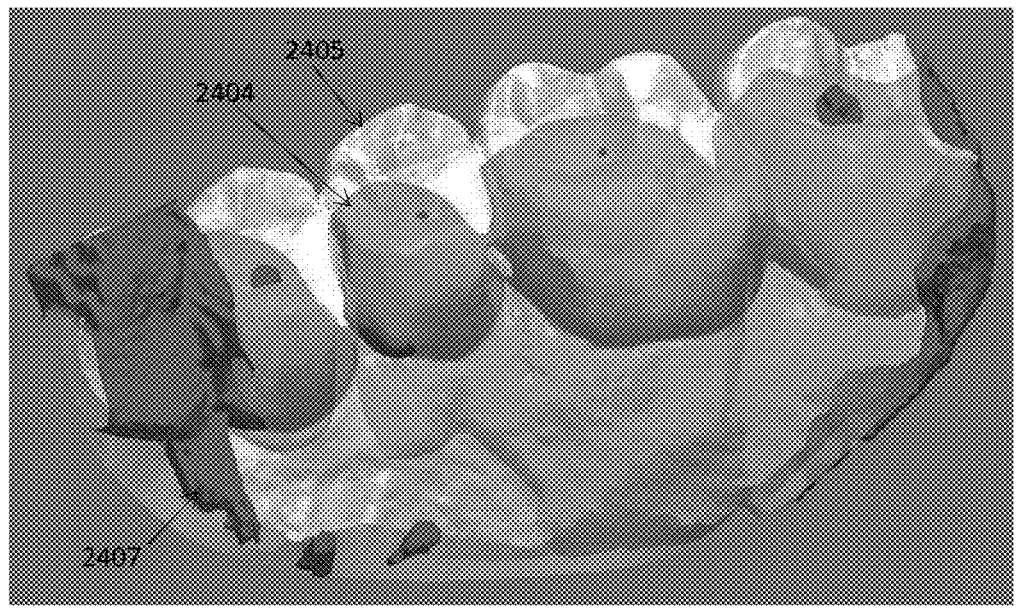
FIG. 24A is a partial three-dimensional model of a patient's teeth formed by segmented images, including those shown in FIGS. 18A-23C.
Figure 24B:
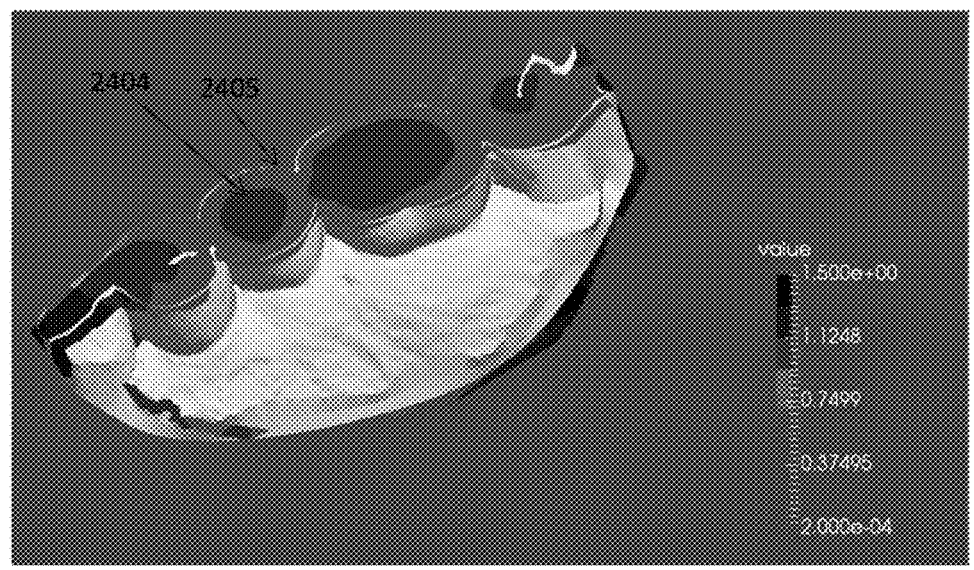
FIG. 24B shows a sectional view through the 3D model of FIG. 24A, showing internal structures, including the dentin.

The segmented images, such as those shown in FIGS. 18A-23C may be used to form a model of the internal structures of the scanned object (e.g., teeth). The surface 3D model may also be used. For example, FIGS. 24A-24B show a three-dimensional model of a region of the patient's teeth formed by segmented images, including those shown in FIGS. 18A-23C. In FIG. 24A, the 3D reconstruction includes the outer surface of the teeth (shown as partially transparent), and different internal segments may be shown in different colors and/or transparencies. For example, In FIG. 24A, the dentin (inner part of teeth) 2404 is shown within the teeth 2405 boundary. In FIG. 24A the segment showing the dentin is a surface (volume in FIG. 24B), but it may also be shown as a density map, as will be illustrated in FIGS. 25A and 25B, below. The resulting 3D volume including the segmented images may be iteratively used to take images through the resulting volume, which may be 'projections' that can be compared directly to the original near-IR images, and this comparison may be used to modify the model. This process may be repeated (iterated) to refine the model, which may provide better segmentation of images.

As described above, segmentation may include edge detection. Any appropriate edge detection method may be used, including machine learning. Segmentation of the plurality of near-IR images may be used in conjunction with the positional information of the camera to reconstruct the volume. Since a plurality of different sections (different conics) are known, and segmented, the resulting segments inside of all of the projections of the conics, from different positions are known and intersections of these segments may therefore be determined. This process may be made easier by using the outer surface boundary of the teeth, which may be provided by the surface imaging and/or the 3D model. As described above, this process may be iterative; the method may use the 3D data to project simulated penetrative (e.g., near-IR) images that may be compared to the original to improve segmentation and derive a second, evolved, model of the internal structures. Similarly, segments or segment regions outside of the teeth surface 2407 may be removed.

The model of the tooth, including internal structures, may be displayed in a variety of ways, as mentioned above. FIG. 24B shows a section through the teeth, showing the internal structures, including the dentin 2404 and the enamel thickness between the outer surface 2405 and the dentin 2404.

Figure 25A:
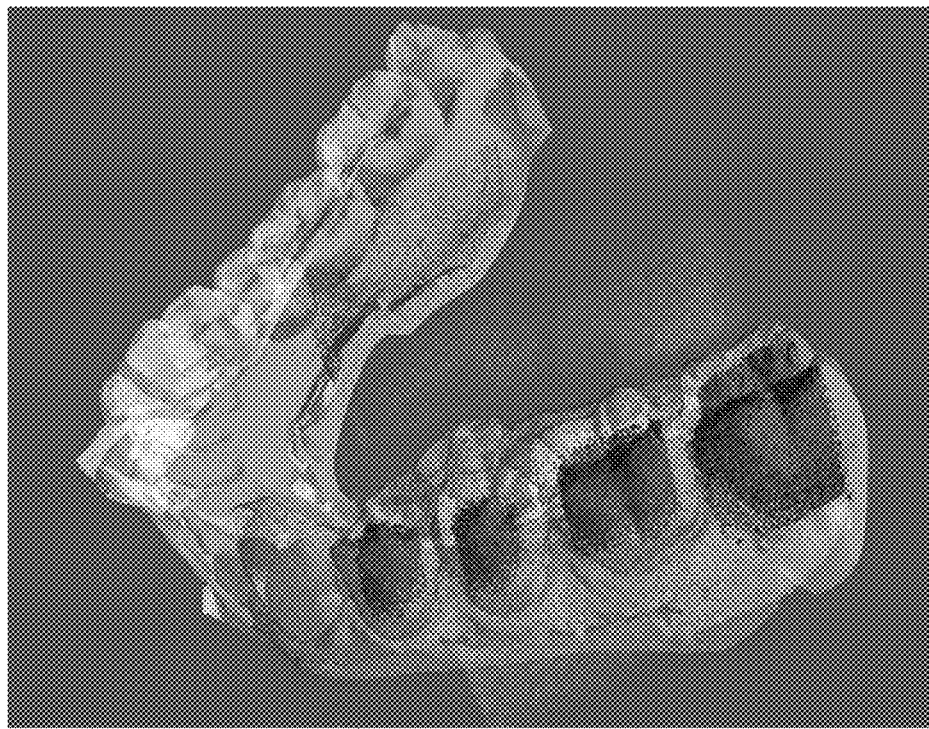
FIG. 25A is an example of a volumetric (or "voxel") model of a patient's jaw and teeth, including internal structures. The internal structures are shown as a density map within the 3D surface model.
Figure 25B:
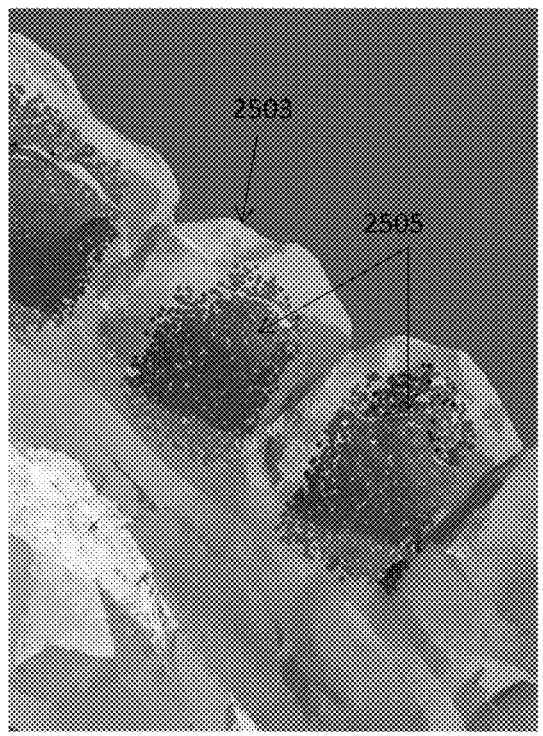
FIG. 25B is an enlarged view of the volumetric model of FIG. 25A.

FIGS. 25A and 25B show an reconstruction of the teeth including internal structures (also shown in FIG. 17, above). In this example, the internal structures are shown by a density mapping (e.g., segments). For example, the dentin 2505 is shown in more detail within a portion of the surface model 2503 in FIG. 25B. The outer surface of the teeth may also be identified as a segment (as shown in FIGS. 25A and 25B), and there is near-perfect agreement between the segmented outer surface and the outer surface as determined from surface imaging in this example.

Sleeves for Intraoral Scanners having Trans-Illumination

Any of the devices described herein may also include a sleeve or sleeves that is configured to protect the intraoral scanner wand, but may also be configured to extend the functionality and/or adapt the scanner for use with a penetrative wavelength, including trans-illumination. The sleeve illustrated in FIGS. 29A-31B is an example of a sleeve that may be used as a barrier (e.g., sanitary barrier) to prevent contamination of the wand portion of the intraoral scanner, as the scanner may be used with different patients, and also as an adapter for providing trans-illumination by IR/near-IR wavelength imaging. The sleeve in these figures is configured as a trans-illumination sleeve with electrical couplings. For example, the sleeves described herein may include both penetrative wavelength illumination (e.g., near-IR and/or IR LEDs) and one or more sensors (e.g., CCDs) or may use the same cameras already on the wand.

In FIG. 29A, the wand of an intra-oral scanner is shown with a sleeve 3101 disposed around the end of the wand 3105; the sleeve is shown as semi-transparent, so that the internal structures (connectors) are visible. FIG. 29B shows just the sleeve 3105 for the intraoral scanner (wand) shown as solid. In general, the sleeve 3105 slips over the end of the wand so that the light sources and cameras (sensors) already on the wand are able to visualize through the sleeve, and so that the electrical contacts 3123, which may provide control, power and/or data transmission to the LEDs and/or sensors 3125 integrated into or on the sleeve. The sleeve includes a pair of wing regions 3103 on opposite sides, facing each other and extending from the distal end of the wand when the sleeve is placed over the wand.

The sleeve 3101 may be held on the end of the wand by friction or by an attachment (not shown). Consequently, the sleeve may be readily removed from the wand and a new sleeve can be placed on the wand each time the scanner is used on a different patient. In this example, the sleeve may be configured to transmit IR (e.g., near IR), and thus may include one or more projections 3103 (e.g., for trans-illumination, etc.) as shown in FIG. 29B. The electrical contacts and connector integrated into the sleeve may adapt the scanner for IR/near-IR trans-illumination.

Thus, the sleeve may include circuitry (e.g., flex circuitry) connecting to an LED illumination (IR/near-IR) source and/or one or more sensors, particularly for trans-illumination. FOR example, FIGS. 30A-30C. FIG. 30A shows an example of the frame 3201 of the sleeve, which may be rigid or semi-rigid. The frame may support the flex circuitry 3203 (shown in FIG. 30B) and/or connectors 3205 and may also provide shielding (e.g., blocking light). The frame and circuitry may be covered by a flexible outer sleeve 3207 as shown in FIG. 30C.

The sleeve may be assembled by injection molding of the component parts, including the overall sleeve, windows for illumination and image capture, connectors for the circuitry and one or more LED holding regions (e.g., injection of an IR and visible-light transparent material forming windows through the sleeve, then injection of the rigid sleeve material). The flex circuitry may then be positioned, and LED encapsulation may be placed, using mold locators. The flexible outer sleeve may then be injected.

Figure 31B:
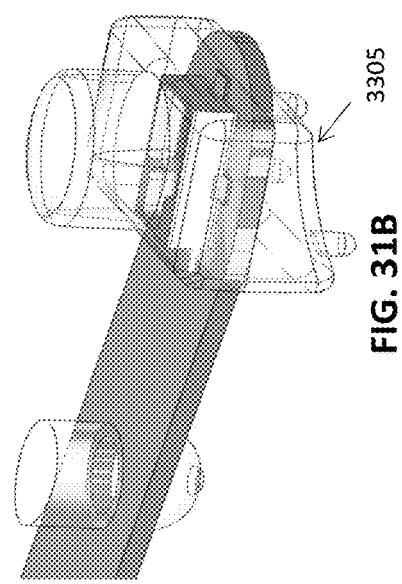
FIG. 31B is an example of a distal end portion of the flex circuit shown in FIG. 31A, including an LED housing.
Figure 31C:
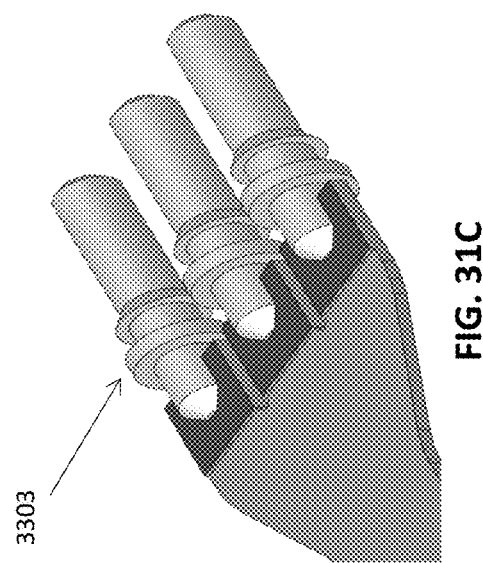
FIG. 31C is an example of a connector portion of a sleeve.
Figure 31A:
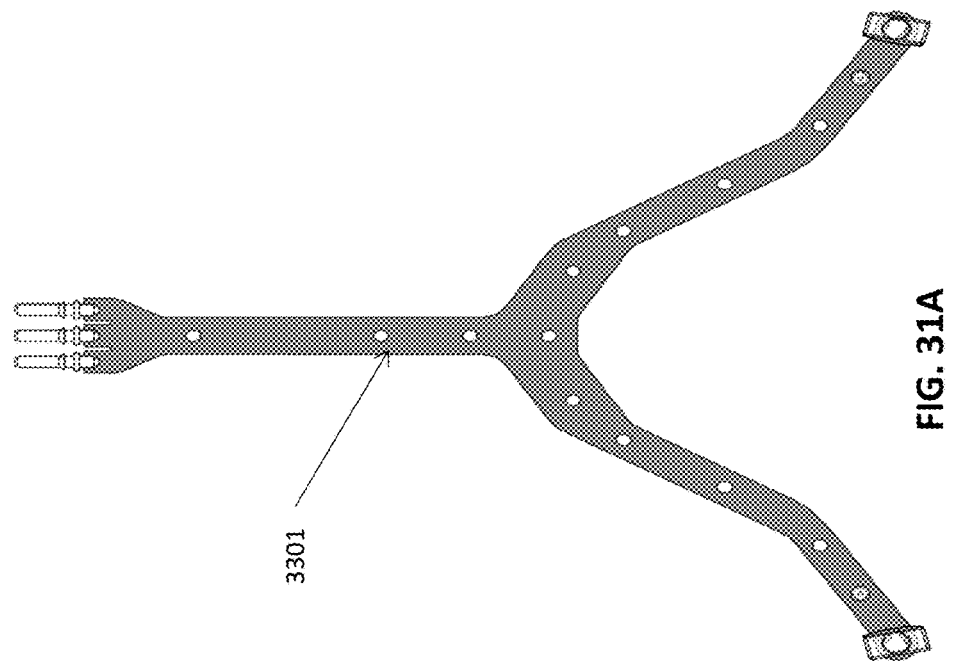
FIG. 31A shows an example of a flex circuit and connectors for use as part of the sleeve shown in FIGS. 29A-30B.
Figure 32B:
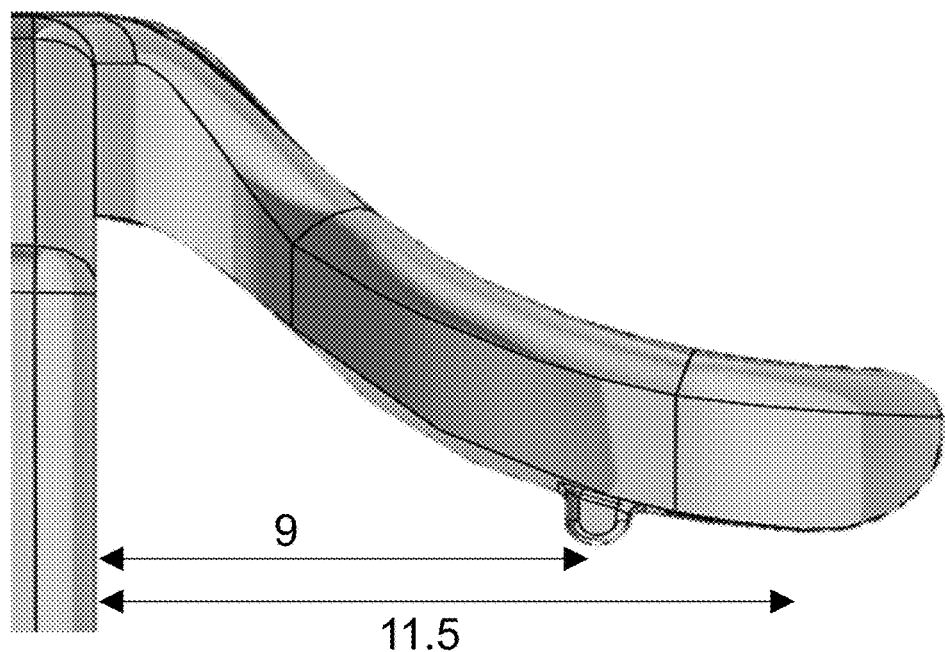
FIGS. 32A and 32B illustrate examples of an LED positioner and light blocker portion of the distal end of a sleeve such as the ones shown in FIGS. 29A-30B.
Figure 32A:
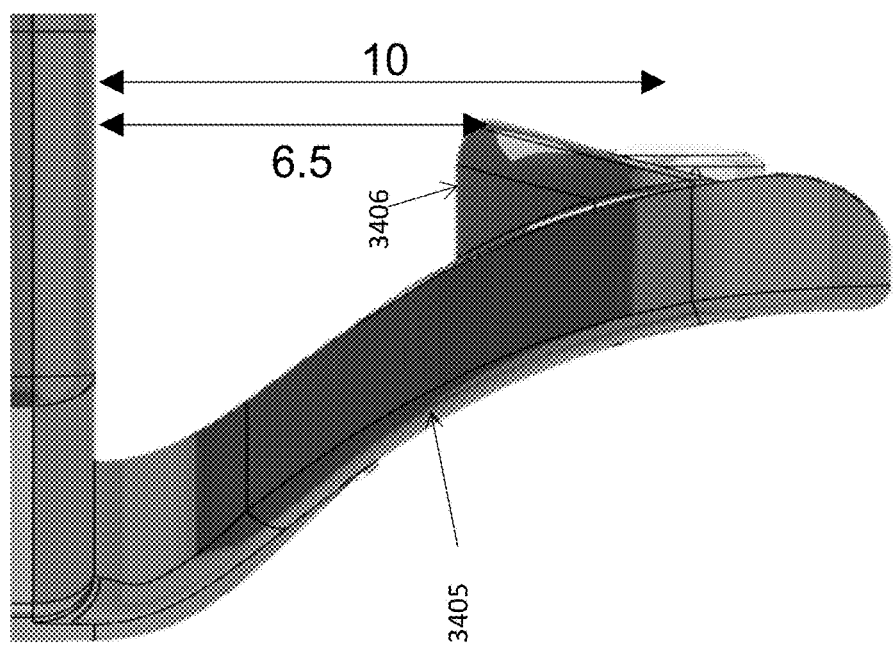

FIGS. 31A-31C illustrate more detailed views of the flex circuitry 3301, connectors 3303 and LED holders/shields 3305. FIGS. 32A-32B illustrate examples of the LED positioner and light blocker portion of the distal end of the sleeve. The example shown in FIG. 32A includes a support frame or arm 3404 that extends down and includes a light shroud or blocker region 3406 encapsulating a portion of the LED. Exemplary dimensions are shown.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method comprising:
   receiving data associated with an intraoral scan of a subject, wherein the data comprises a plurality of sets of both tooth surface and infrared (IR) images, each set corresponding to a position relative to the subject's teeth;
   determining, from the received data, a first plurality of voxels describing at least a portion of a first internal feature of a tooth of the subject;
   determining, from the received data, a second plurality of voxels describing at least a portion of a second internal feature of the tooth of the subject, the first internal feature differing from the second internal feature; and
   outputting a three-dimensional (3D) volumetric model in which the first and second plurality of voxels are aligned and merged, the 3D volumetric model including the first internal feature and the second internal feature.

2. The method of claim 1, further comprising mapping at least some of the first plurality of voxels with at least some of the second plurality of voxels.

3. The method of claim 1, wherein the IR images of the received data comprises tooth surface penetrating intraoral near-IR images.

4. The method of claim 1, wherein the tooth surface images of the received data comprise visible light images of tooth surface intraoral scans of the subject.

5. The method of claim 1, further comprising determining, from the received data, a surface of the tooth of the subject; mapping the surface of the tooth with the first plurality of voxels and the second plurality of voxels; and outputting the 3D volumetric model with the surface of the tooth with a combined volumetric model comprising the first and second plurality of voxels and including the at least a portion of the first internal feature and the at least a portion of the second internal feature.

6. The method of claim 5, wherein the received data further comprises data from a tooth surface color intraoral scan of the subject.

7. The method of claim 5, further comprising, determining, from the received data, a color of the surface of the tooth of the subject; mapping the color of the surface of the tooth to the surface of the tooth; and outputting the 3D volumetric model with the surface of the tooth and the color of the surface of the tooth.

8. The method of claim 1, wherein the first internal feature of the tooth comprises a dentin of the tooth and the second internal feature of the tooth comprises an enamel of the tooth.

9. The method of claim 8, wherein receiving data associated with the intraoral scan comprises receiving data associated with a first intraoral scan; further comprising receiving data associated with a second intraoral scan of the subject; and determining from the received data associated with the first intraoral scan of the subject, the first plurality of voxels describing at least a portion of the enamel or the dentin; and determining a volume change of the enamel or the dentin by comparing the first plurality of voxels to the second plurality of voxels; and outputting the determined volume change.

10. The method of claim 1, further comprising detecting a dental caries of the tooth from the 3D volumetric model.

11. The method of claim 10, wherein detecting the dental caries of the tooth comprises analyzing whether the second internal feature extends from a surface of the volume of the first internal feature.

12. The method of claim 11, wherein analyzing comprises determining whether the second internal feature extends from the surface of the volume of the first internal feature and to a portion of the second internal feature associated with the dentin.

13. The method of claim 11, further comprising calculating a volume of the second internal feature that extends from the surface of the volume of the first internal feature and outputting a signal associated with the calculated volume.

14. A method comprising:
receiving data associated with an intraoral scan of a patient, wherein the data comprises a plurality of sets of both tooth surface and infrared (IR) images, each set corresponding to a position relative to the subject's teeth;
determining, from the received data, a first plurality of voxels describing a first internal feature of a tooth of the patient;
determining, from the received data, a second plurality of voxels describing a second internal feature of the tooth of the patient, the first internal feature differing from the second internal feature;
mapping the first plurality of voxels to the second plurality of voxels to generate a three-dimensional (3D) volumetric model including the first internal feature and the second internal feature;
outputting, on a monitor connected to the intraoral scanner, the 3D volumetric model including the first internal feature and the second internal feature.

15. A method comprising:
receiving data associated with an intraoral scan of a subject, wherein the data comprises a plurality of sets of tooth surface and infrared (IR) images, each set corresponding to a position relative to the subject's teeth;
generating a three-dimensional (3D) volumetric model from the data by determining a plurality of sets of voxels for internal features of the subject's teeth and matching the plurality of sets of voxel volumes to from the 3D volume;
determining, from the 3D volumetric model, a volume of a dental caries of a tooth of the subject;
outputting an output associated with the volume of the dental caries of the tooth of the subject.

16. The method of claim 15, further comprising determining, from the 3D volumetric model, a volumetric model of an enamel of the tooth of the subject; mapping the volumetric model of the enamel to the volumetric model of the dental caries; and outputting an output associated with the enamel and the dental caries to a user.

17. The method of claim 16, further comprising detecting, from the 3D volumetric model, a dentin of the tooth of the subject; and outputting a 3D volumetric model including the enamel and the dental caries with a volume of the dentin.

18. The method of claim 15, wherein the intraoral scan of the subject comprises a second intraoral scan of the subject and wherein the method further comprises receiving data associated with a prior intraoral scan of the subject; determining, from the received data associated with the prior intraoral scan of the subject, a prior volume of the dental caries of the tooth of the subject; outputting a signal associated with a difference in volume between the volume of the dental caries and the prior volume of the dental caries.

19. The method of claim 15, further comprising outputting the three-dimensional (3D) volumetric model including the volume of the dental caries of the tooth of the subject.

20. A method comprising:
receiving data associated with an intraoral scan of a subject, wherein the data comprises a plurality of sets of tooth surface and infrared (IR) images, each set corresponding to a position relative to the subject's teeth;
generating a three-dimensional (3D) volumetric model from the data by determining a plurality of sets of voxels for internal features of the subject's teeth and matching the plurality of sets of voxel volumes to from the 3D volume;
determining, from the 3D volumetric model, a volume of dentin and a volume of enamel of a tooth of the subject;
determining, from the 3D volumetric model, a volume of dental caries of a tooth of the subject;
outputting a, user-manipulatable 3D volumetric model of the tooth of the subject, indicating the volume of enamel, the volume of dentin, and the volume of dental caries of the tooth of the subject.

* * * * *